US009893297B2

(12) United States Patent
Martynova et al.

(10) Patent No.: US 9,893,297 B2
(45) Date of Patent: Feb. 13, 2018

(54) MATERIALS FOR ELECTRONIC DEVICES

(75) Inventors: Irina Martynova, Griesheim (DE); Adam W. Franz, Kelkheim (DE); Christof Pflumm, Darmstadt (DE); Amir Hossain Parham, Frankfurt am Main (DE); Arne Buesing, Frankfurt am Main (DE); Rémi Manouk Anémian, Seoul (KR); Anja Gerhard, Egelsbach (DE)

(73) Assignee: Merck Patent GmbH, Darmstadt (DE)

( * ) Notice: Subject to any disclaimer, the term of this patent is extended or adjusted under 35 U.S.C. 154(b) by 881 days.

(21) Appl. No.: 13/813,162

(22) PCT Filed: Jul. 12, 2011

(86) PCT No.: PCT/EP2011/003484
§ 371 (c)(1),
(2), (4) Date: Jan. 30, 2013

(87) PCT Pub. No.: WO2012/016630
PCT Pub. Date: Feb. 9, 2012

(65) Prior Publication Data
US 2013/0126792 A1    May 23, 2013

(30) Foreign Application Priority Data

Aug. 5, 2010   (DE) .................. 10 2010 033 548

(51) Int. Cl.
| | |
|---|---|
| *H01L 51/00* | (2006.01) |
| *C07D 491/04* | (2006.01) |
| *C07D 491/14* | (2006.01) |
| *C07D 495/04* | (2006.01) |
| *C07D 495/14* | (2006.01) |
| *C07F 9/6568* | (2006.01) |
| *C07F 15/00* | (2006.01) |
| *H01L 51/50* | (2006.01) |

(52) U.S. Cl.
CPC ........ *H01L 51/0071* (2013.01); *C07D 491/04* (2013.01); *C07D 491/14* (2013.01); *C07D 495/04* (2013.01); *C07D 495/14* (2013.01); *C07F 9/65683* (2013.01); *C07F 9/65685* (2013.01); *C07F 15/0033* (2013.01); *C07F 15/0086* (2013.01); *H01L 51/0036* (2013.01); *H01L 51/0067* (2013.01); *H01L 51/0072* (2013.01); *H01L 51/0074* (2013.01); *H01L 51/0094* (2013.01); *B32B 2457/202* (2013.01); *H01L 51/006* (2013.01); *H01L 51/0056* (2013.01); *H01L 51/0058* (2013.01); *H01L 51/5012* (2013.01); *H01L 51/5056* (2013.01); *H01L 51/5072* (2013.01); *Y02E 10/549* (2013.01)

(58) Field of Classification Search
None
See application file for complete search history.

(56) References Cited

U.S. PATENT DOCUMENTS 6,193,912 B1 * 2/2001 Thieste .................. C09K 9/02
                                                              252/583
6,451,724 B1 * 9/2002 Nifant'ev et al. ............ 502/103
6,710,906 B2 * 3/2004 Guarr ....................... C09K 9/00
                                                              359/265
2008/0220285 A1  9/2008 Vestweber et al.
2009/0236978 A1 * 9/2009 Lemaitre ............. C07F 9/65685
                                                              313/504

FOREIGN PATENT DOCUMENTS

| JP | 2001-508083 A | 6/2001 | |
|---|---|---|---|
| JP | 2005-199633 A | 7/2005 | |
| JP | 2006-081987 A | 3/2006 | |
| JP | 2006219393 A † | 8/2006 | |
| JP | 4319958 B2 | 8/2009 | |
| JP | 4329547 B2 | 9/2009 | |
| JP | 2010-040829 A | 2/2010 | |
| WO | WO-99/45081 A1 | 9/1999 | |
| WO | WO-2006122630 A1 | 11/2006 | |
| WO | WO-2009/063780 A1 | 5/2009 | |
| WO | WO 2010046259 A1 * | 4/2010 | ........... C07D 487/04 |

OTHER PUBLICATIONS

Poriel et al. (Oxidative Rearrangement of Indoles: A New Approach to the EFHG-Tetracyclic Core of Diazonamide A, J. Org. Chem. 2007, 72, 2978-2987).*
Beyts et al., "Action of Nitric Acid on Polycyclic Indole Derivatives. Part XIII Indeno(2':3':2:3)Indole", *Journal of the Chemical Society*, pp. 1534-1536 (Jan. 1, 1939).
Brown et al., "The Fischer Indolisation Reaction and the Synthesis of Dihydroindenoindoles", *Tetrahedron*, vol. 49, No. 39, pp. 8919-8932 (1993).
Shimizu et al., "Modular Approach to Silicon-Bridged Biaryls: Palladium-Catalyzed Intramolecular Coupling of 2-(Arylsilyl)aryl Triflates", *Angew. Chem. Int. Ed.*, vol. 47, No. 50, pp. 9760-9764 (2008).
Giacometti et al., "Synthesis of Polycyclic Indolone and Pyrroloindolone Heterocycles via the Annulation of Indole- and Pyrrole-2-Carboxylate Esters with Arynes", *Synlett*, No. 12, pp. 2010-2016 (2009).
Kienle et al., "Synthesis of Dibenzothiophenes and Related Classes of Heterocycles by Using Functionalized Dithiocarbamates", *Angew. Chem. Int. Ed.*, vol. 49, pp. 4751-4754 (2010).
Kothandaraman et al., "Gold-Catalyzed Cycloisomerization Reactions of 2-Tosylaminophenylprop-1-yn-3-ols as a Versatile Approach for Indole Synthesis", *Angew. Chem. Int. Ed.*, vol. 49, pp. 4619-4623 (2010).
Kienle et al., "Preparation of Heterocyclic Amines by an Oxidative Amination of Zinc Organometallics Mediated by CuI: A New Oxidative Cycloamination for the Preparation of Annulated Indole Derivatives", *Chem. Asian J.*, vol. 6, No. 2 pp. 517-523 (2011).
International Search Report for PCT/EP2011/003484 dated Nov. 14, 2011.

* cited by examiner
† cited by third party

*Primary Examiner* — Anthony J Frost

(57) ABSTRACT

The present invention relates to compounds of the formula (I), to the use of compounds of the formula (I) in electronic devices and electronic devices comprising one or more compounds of the formula (I). The invention furthermore relates to the preparation of the compounds of the formula (I) and to formulations comprising one or more compounds of the formula (I).

16 Claims, No Drawings

MATERIALS FOR ELECTRONIC DEVICES

CROSS-REFERENCE TO RELATED APPLICATIONS

This application is a national stage application (under 35 U.S.C. § 371) of PCT/EP2011/003484, filed Jul. 12, 2011, which claims benefit of German application 10 2010 033 548.7, filed Aug. 5, 2010 which are both incorporated by reference.

The present invention relates to compounds of the formula (I) and to the use of compounds of the formula (I) in electronic devices. The invention furthermore relates to electronic devices, preferably organic electroluminescent devices (OLEDs), comprising one or more compounds of the formula (I). The invention again furthermore relates to the preparation of compounds of the formula (I) and to formulations comprising one or more compounds of the formula (I).

The structure of organic electroluminescent devices (OLEDs) in which organic semiconductors, such as the compounds according to the invention, are employed as functional materials is described, for example, in U.S. Pat. No. 4,539,507, U.S. Pat. No. 5,151,629, EP 0676461 and WO 98/27136.

The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescence emitters.

In general, there is still a need for improvement, for example with respect to efficiency, operating voltage and, in particular, lifetime, in OLEDs, in particular also in OLEDs which exhibit triplet emission (phosphorescence). This applies, in particular, to OLEDs which emit in the relatively short-wave region, for example green.

The properties of phosphorescent OLEDs are determined not only by the phosphorescent dopants employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. There is also still a need for improvement in these materials for fluorescent OLEDs.

Matrix materials for phosphorescent dopants which are known in the prior art are, inter alia, carbazole derivatives, for example bis(carbazolyl)biphenyl. The use of ketones (WO 2004/093207), phosphine oxides and sulfones (WO 2005/003253) is furthermore known as matrix materials for phosphorescent dopants. Metal complexes, for example BAlq or bis[2-(2-benzothiazole)phenolate]zinc(II), are also used as matrix materials for phosphorescent dopants.

However, there continues to be a demand for alternative matrix materials for phosphorescent dopants, in particular those which effect an improvement in the performance data of the electronic devices.

Furthermore, the provision of novel hole-transport and hole-injection materials is of interest. Hole-transport and injection materials which are known in the prior art are, inter alia, arylamine compounds. Materials of this type based on indenofluorenes are disclosed, for example, in the applications WO 2006/100896 and WO 2006/122630.

However, the known hole-transporting materials frequently have low electron stability, which reduces the lifetime of electronic devices comprising these compounds.

Furthermore, improvements are desirable with respect to the efficiency of fluorescent organic electroluminescent devices and the lifetime, especially in the case of blue-fluorescent devices.

The provision of novel electron-transport materials is likewise desirable since the properties of the electron-transport material exert a significant influence on the above-mentioned properties of the organic electroluminescent device. In particular, there is a demand for electron-transport materials which simultaneously result in good efficiency, a long lifetime and a low operating voltage.

It would be desirable here to have available electron-transport materials which result in better electron injection into the emitting layer, since an electron-richer emission layer is accompanied by better efficiency. In addition, better injection enables the operating voltage to be reduced.

The object of the present invention is thus in summary the provision of compounds which are suitable for use in a fluorescent or phosphorescent OLED, in particular a phosphorescent OLED, in particular as matrix material or as electron-transport or hole-blocking material.

Levy et al., Bull. Soc. Chim. Fr. 1987, 1, 193-198, describe the synthesis of certain unsubstituted indolobenzo-thiophene derivatives. However, the electroluminescence properties of the compounds or a use of the compounds as functional materials in electronic devices are not disclosed.

It has now been found that compounds of the formula (I) which were hitherto not known in the prior art are eminently suitable for use as functional materials in electronic devices, in particular as matrix materials for phosphorescent dopants. On use of the compounds according to the invention, higher efficiencies and longer lifetimes can preferably be achieved than with materials in accordance with the prior art.

The present invention thus relates to a compound of the following formula (I)

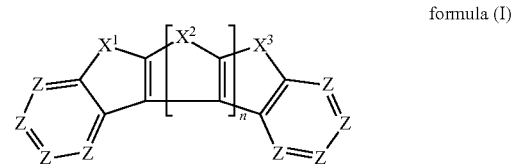

formula (I)

where the following applies to the symbols and indices occurring:

$X^1$, $X^2$, $X^3$ are on each occurrence, identically or differently, $C(R^2)_2$, C=O, C=$NR^2$, $Si(R^2)_2$, $NR^1$, $PR^1$, P(=O)$R^1$, O, S, S=O or S(=O)$_2$;

Z is on each occurrence, identically or differently, $CR^2$ or N, where not more than two adjacent groups Z may simultaneously be equal to N;

$R^1$ is on each occurrence, identically or differently, C(=O)$R^3$, $CR^3$=$C(R^3)_2$, C(=O)$OR^3$, C(=O)$NR^3_2$, P(=O)($R^3)_2$, $OR^3$, S(=O)$R^3$, S(=O)$_2R^3$, or an aromatic or heteroaromatic ring system having 5 to 60 aromatic ring atoms, which may in each case be substituted by one or more radicals $R^3$, or a combination of these systems, where two or more radicals $R^1$ may be linked to one another and may form an aliphatic or aromatic ring;

$R^2$ is on each occurrence, identically or differently, H, D, F, Cl, Br, I, B(OR$^3)_2$, CHO, C(=O)$R^3$, $CR^3$=$C(R^3)_2$, CN, C(=O)$OR^3$, C(=O)$NR^3_2$, $Si(R^3)_3$, $N(R^3)_2$, $NO_2$, P(=O)($R^3)_2$, OS(=O)$_2R^3$, OH, S(=O)$R^3$, S(=O)$_2R^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals R³ and where one or more non-adjacent CH₂ groups in the above-mentioned groups may be replaced by —R³C=CR³—, —C≡C—, Si(R³)₂, Ge(R³)₂, Sn(R³)₂, C=O, C=S, C=Se, C=NR³, —C(=O)O—, —C(=O)NR³—, NR³, P(=O)(R³), —O—, —S—, S=O or S(=O)₂ and where one or more H atoms in the above-mentioned groups may be replaced by D, F, Cl, Br, I, CN or NO₂, or an aromatic or heteroaromatic ring system having 5 to 60 aromatic ring atoms, which may in each case be substituted by one or more radicals R³, or an aryloxy or heteroaryloxy group having 5 to 60 aromatic ring atoms, which may be substituted by one or more radicals R³, or a combination of these systems, where two or more radicals R² may be linked to one another and may form an aliphatic or aromatic ring;

R³ is on each occurrence, identically or differently, H, D, F, Cl, Br, I, B(OR⁴)₂, CHO, C(=O)R⁴, CR⁴=C(R⁴)₂, CN, C(=O)OR⁴, C(=O)NR⁴₂, Si(R⁴)₃, N(R⁴)₂, NO₂, P(=O)(R⁴)₂, OS(=O)₂R⁴, OH, S(=O) R⁴, S(=O)₂R⁴, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals R⁴ and where one or more non-adjacent CH₂ groups in the above-mentioned groups may be replaced by —R⁴C=CR⁴—, —C≡C—, Si(R⁴)₂, Ge(R⁴)₂, Sn(R⁴)₂, C=O, C=S, C=Se, C=NR⁴, —C(=O)O—, —C(=O)NR⁴—, NR⁴, P(=O)(R⁴), —O—, —S—, S=O or S(=O)₂ and where one or more H atoms in the above-mentioned groups may be replaced by D, F, Cl, Br, I, CN or NO₂, or an aromatic or heteroaromatic ring system having 5 to 60 aromatic ring atoms, which may in each case be substituted by one or more radicals R⁴, or an aryloxy or heteroaryloxy group having 5 to 60 aromatic ring atoms, which may be substituted by one or more radicals R⁴, or a combination of these systems, where two or more radicals R³ may be linked to one another and may form an aliphatic or aromatic ring;

R⁴ is, identically or differently on each occurrence, H, D, F or an aliphatic, aromatic and/or heteroaromatic organic radical having 1 to 20 C atoms, in which, in addition, one or more H atoms may be replaced by D or F; two or more substituents R⁴ here may also be linked to one another and form an aliphatic or aromatic ring; and n has a value of 0, 1 or 2; and where the case where all groups X¹, X² and X³ are identical is excluded.

For clarity, it should be noted that the compounds of the formula (I) conform to the following formula (Ia) for n=0, to the following formula (Ib) for n=1 and to the following formula (Ic) for n=2:

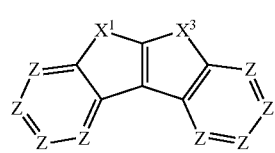

formula (Ia)

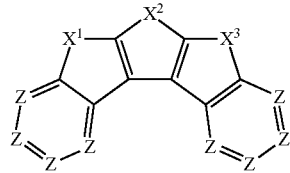

formula (Ib)

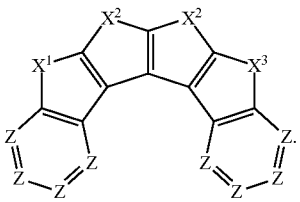

formula (Ic)

In the case of compounds of the formula (Ic), the groups X² occurring may furthermore be identical or different.

An aryl group in the sense of this invention contains 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

An aryl or heteroaryl group, which may in each case be substituted by the above-mentioned radicals R² or R³ and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp³-hybridised C, Si, N or O atom, an sp²-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via one or more single bonds are also taken to be aromatic or heteroaromatic ring systems in the sense of this invention.

An aromatic or heteroaromatic ring system having 5-60 aromatic ring atoms, which may also in each case be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals $R^2$ and $R^3$, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, tbutoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

In a preferred embodiment of the invention, 0, 1 or 2 groups Z per aromatic or heteroaromatic six-membered ring are equal to N. In a particularly preferred embodiment of the invention, no or precisely one group Z per aromatic or heteroaromatic six-membered ring is equal to N. In an even more preferred embodiment of the invention, no group Z is equal to N and all groups Z are equal to $CR^2$.

In a further preferred embodiment of the invention, n is equal to 0 or 1. In these cases, the compounds according to the invention conform to the formulae (Ia) and (Ib) shown above.

It is furthermore preferred for $X^1$ to be selected from $C(R^2)_2$, C=O, $Si(R^2)_2$, $NR^1$, $PR^1$, $P(=O)R^1$, O or S. $X^1$ is very particularly preferably selected from $NR^1$, $PR^1$, $P(=O)R^1$, O or S.

It is furthermore preferred for $X^2$ to be selected on each occurrence, identically or differently, from $C(R^2)_2$, C=O, $Si(R^2)_2$, $NR^1$, $PR^1$, $P(=O)R^1$, O or S. $X^2$ is very particularly preferably selected on each occurrence, identically or differently, from $NR^1$, $PR^1$, $P(=O)R^1$, O or S.

It is furthermore preferred for $X^3$ to be selected from $C(R^2)_2$, C=O, $Si(R^2)_2$, $NR^1$, $PR^1$, $P(=O)R^1$, O or S. $X^3$ is very particularly preferably selected from $NR^1$, $PR^1$, $P(=O)R^1$, O or S.

Preferred combinations of the groups $X^1$ and $X^3$ for compounds of the formula (I) where n=0 (formula (Ia)) are indicated in the following table.

| | $X^1$ | $X^3$ |
|---|---|---|
| 1 | $C(R^2)_2$ | C=O |
| 2 | $C(R^2)_2$ | $NR^1$ |
| 3 | $C(R^2)_2$ | $PR^1$ |
| 4 | $C(R^2)_2$ | $P(=O)R^1$ |
| 5 | $C(R^2)_2$ | O |
| 6 | $C(R^2)_2$ | S |
| 7 | C=O | $C(R^2)_2$ |
| 8 | C=O | $NR^1$ |
| 9 | C=O | $PR^1$ |
| 10 | C=O | $P(=O)R^1$ |
| 11 | C=O | O |
| 12 | C=O | S |
| 13 | $NR^1$ | $C(R^2)_2$ |
| 14 | $NR^1$ | C=O |
| 15 | $NR^1$ | $PR^1$ |
| 16 | $NR^1$ | $P(=O)R^1$ |
| 17 | $NR^1$ | O |
| 18 | $NR^1$ | S |
| 19 | $PR^1$ | $C(R^2)_2$ |
| 20 | $PR^1$ | C=O |
| 21 | $PR^1$ | $NR^1$ |
| 22 | $PR^1$ | $P(=O)R^1$ |
| 23 | $PR^1$ | O |
| 24 | $PR^1$ | S |
| 25 | $P(=O)R^1$ | $C(R^2)_2$ |
| 26 | $P(=O)R^1$ | C=O |
| 27 | $P(=O)R^1$ | $NR^1$ |
| 28 | $P(=O)R^1$ | $PR^1$ |

| | $X^1$ | $X^3$ |
|---|---|---|
| 29 | $P(=O)R^1$ | O |
| 30 | $P(=O)R^1$ | S |
| 31 | O | $C(R^2)_2$ |
| 32 | O | C=O |
| 33 | O | $NR^1$ |
| 34 | O | $PR^1$ |
| 35 | O | $P(=O)R^1$ |
| 36 | O | S |
| 37 | S | $C(R^2)_2$ |
| 38 | S | C=O |
| 39 | S | $NR^1$ |
| 40 | S | $PR^1$ |
| 41 | S | $P(=O)R^1$ |
| 42 | S | O |

Preferred combinations of the groups $X^1$, $X^2$ and $X^3$ for compounds of the formula (I) where n=1 (formula (Ib)) are indicated in the following table.

| | $X^1$ | $X^2$ | $X^3$ |
|---|---|---|---|
| 44 | $C(R^2)_2$ | $C(R^2)_2$ | C=O |
| 45 | $C(R^2)_2$ | $C(R^2)_2$ | $NR^1$ |
| 46 | $C(R^2)_2$ | $C(R^2)_2$ | $PR^1$ |
| 47 | $C(R^2)_2$ | $C(R^2)_2$ | $P(=O)R^1$ |
| 48 | $C(R^2)_2$ | $C(R^2)_2$ | O |
| 49 | $C(R^2)_2$ | $C(R^2)_2$ | S |
| 50 | $C(R^2)_2$ | C=O | $C(R^2)_2$ |
| 51 | $C(R^2)_2$ | C=O | C=O |
| 52 | $C(R^2)_2$ | C=O | $NR^1$ |
| 53 | $C(R^2)_2$ | C=O | $PR^1$ |
| 54 | $C(R^2)_2$ | C=O | $P(=O)R^1$ |
| 55 | $C(R^2)_2$ | C=O | O |
| 56 | $C(R^2)_2$ | C=O | S |
| 57 | $C(R^2)_2$ | $NR^1$ | $C(R^2)_2$ |
| 58 | $C(R^2)_2$ | $NR^1$ | C=O |
| 59 | $C(R^2)_2$ | $NR^1$ | $NR^1$ |
| 60 | $C(R^2)_2$ | $NR^1$ | $PR^1$ |
| 61 | $C(R^2)_2$ | $NR^1$ | $P(=O)R^1$ |
| 62 | $C(R^2)_2$ | $NR^1$ | O |
| 63 | $C(R^2)_2$ | $NR^1$ | S |
| 64 | $C(R^2)_2$ | $PR^1$ | $C(R^2)_2$ |
| 65 | $C(R^2)_2$ | $PR^1$ | C=O |
| 66 | $C(R^2)_2$ | $PR^1$ | $NR^1$ |
| 67 | $C(R^2)_2$ | $PR^1$ | $PR^1$ |
| 68 | $C(R^2)_2$ | $PR^1$ | $P(=O)R^1$ |
| 69 | $C(R^2)_2$ | $PR^1$ | O |
| 70 | $C(R^2)_2$ | $PR^1$ | S |
| 71 | $C(R^2)_2$ | $P(=O)R^1$ | $C(R^2)_2$ |
| 72 | $C(R^2)_2$ | $P(=O)R^1$ | C=O |
| 73 | $C(R^2)_2$ | $P(=O)R^1$ | $NR^1$ |
| 74 | $C(R^2)_2$ | $P(=O)R^1$ | $PR^1$ |
| 75 | $C(R^2)_2$ | $P(=O)R^1$ | $P(=O)R^1$ |
| 76 | $C(R^2)_2$ | $P(=O)R^1$ | O |
| 77 | $C(R^2)_2$ | $P(=O)R^1$ | S |
| 78 | $C(R^2)_2$ | O | $C(R^2)_2$ |
| 79 | $C(R^2)_2$ | O | C=O |
| 80 | $C(R^2)_2$ | O | $NR^1$ |
| 81 | $C(R^2)_2$ | O | $PR^1$ |
| 82 | $C(R^2)_2$ | O | $P(=O)R^1$ |
| 83 | $C(R^2)_2$ | O | O |
| 84 | $C(R^2)_2$ | O | S |
| 85 | $C(R^2)_2$ | S | $C(R^2)_2$ |
| 86 | $C(R^2)_2$ | S | C=O |
| 87 | $C(R^2)_2$ | S | $NR^1$ |
| 88 | $C(R^2)_2$ | S | $PR^1$ |
| 89 | $C(R^2)_2$ | S | $P(=O)R^1$ |
| 90 | $C(R^2)_2$ | S | O |
| 91 | $C(R^2)_2$ | S | S |
| 92 | C=O | $C(R^2)_2$ | $C(R^2)_2$ |
| 93 | C=O | $C(R^2)_2$ | C=O |
| 94 | C=O | $C(R^2)_2$ | $NR^1$ |
| 95 | C=O | $C(R^2)_2$ | $PR^1$ |
| 96 | C=O | $C(R^2)_2$ | $P(=O)R^1$ |
| 97 | C=O | $C(R^2)_2$ | O |
| 98 | C=O | $C(R^2)_2$ | S |
| 99 | C=O | C=O | $C(R^2)_2$ |
| 100 | C=O | C=O | $NR^1$ |
| 101 | C=O | C=O | $PR^1$ |
| 102 | C=O | C=O | $P(=O)R^1$ |
| 103 | C=O | C=O | O |
| 104 | C=O | C=O | S |
| 105 | C=O | $NR^1$ | $C(R^2)_2$ |
| 106 | C=O | $NR^1$ | C=O |
| 107 | C=O | $NR^1$ | $NR^1$ |
| 108 | C=O | $NR^1$ | $PR^1$ |
| 109 | C=O | $NR^1$ | $P(=O)R^1$ |
| 110 | C=O | $NR^1$ | O |
| 111 | C=O | $NR^1$ | S |
| 112 | C=O | $PR^1$ | $C(R^2)_2$ |
| 113 | C=O | $PR^1$ | C=O |
| 114 | C=O | $PR^1$ | $NR^1$ |
| 115 | C=O | $PR^1$ | $PR^1$ |
| 116 | C=O | $PR^1$ | $P(=O)R^1$ |
| 117 | C=O | $PR^1$ | O |
| 118 | C=O | $PR^1$ | S |
| 119 | C=O | $P(=O)R^1$ | $C(R^2)_2$ |
| 120 | C=O | $P(=O)R^1$ | C=O |
| 121 | C=O | $P(=O)R^1$ | $NR^1$ |
| 122 | C=O | $P(=O)R^1$ | $PR^1$ |
| 123 | C=O | $P(=O)R^1$ | $P(=O)R^1$ |
| 124 | C=O | $P(=O)R^1$ | O |
| 125 | C=O | $P(=O)R^1$ | S |
| 126 | C=O | O | $C(R^2)_2$ |
| 127 | C=O | O | C=O |
| 128 | C=O | O | $NR^1$ |
| 129 | C=O | O | $PR^1$ |
| 130 | C=O | O | $P(=O)R^1$ |
| 131 | C=O | O | O |
| 132 | C=O | O | S |
| 133 | C=O | S | $C(R^2)_2$ |
| 134 | C=O | S | C=O |
| 135 | C=O | S | $NR^1$ |
| 136 | C=O | S | $PR^1$ |
| 137 | C=O | S | $P(=O)R^1$ |
| 138 | C=O | S | O |
| 139 | C=O | S | S |
| 140 | $NR^1$ | $C(R^2)_2$ | $C(R^2)_2$ |
| 141 | $NR^1$ | $C(R^2)_2$ | C=O |
| 142 | $NR^1$ | $C(R^2)_2$ | $NR^1$ |
| 143 | $NR^1$ | $C(R^2)_2$ | $PR^1$ |
| 144 | $NR^1$ | $C(R^2)_2$ | $P(=O)R^1$ |
| 145 | $NR^1$ | $C(R^2)_2$ | O |
| 146 | $NR^1$ | $C(R^2)_2$ | S |
| 147 | $NR^1$ | C=O | $C(R^2)_2$ |
| 148 | $NR^1$ | C=O | C=O |
| 149 | $NR^1$ | C=O | $NR^1$ |
| 150 | $NR^1$ | C=O | $PR^1$ |
| 151 | $NR^1$ | C=O | $P(=O)R^1$ |
| 152 | $NR^1$ | C=O | O |
| 153 | $NR^1$ | C=O | S |
| 154 | $NR^1$ | $NR^1$ | $C(R^2)_2$ |
| 155 | $NR^1$ | $NR^1$ | C=O |
| 156 | $NR^1$ | $NR^1$ | $PR^1$ |
| 157 | $NR^1$ | $NR^1$ | $P(=O)R^1$ |
| 158 | $NR^1$ | $NR^1$ | O |
| 159 | $NR^1$ | $NR^1$ | S |
| 160 | $NR^1$ | $PR^1$ | $C(R^2)_2$ |
| 161 | $NR^1$ | $PR^1$ | C=O |
| 162 | $NR^1$ | $PR^1$ | $NR^1$ |
| 163 | $NR^1$ | $PR^1$ | $PR^1$ |
| 164 | $NR^1$ | $PR^1$ | $P(=O)R^1$ |
| 165 | $NR^1$ | $PR^1$ | O |
| 166 | $NR^1$ | $PR^1$ | S |
| 167 | $NR^1$ | $P(=O)R^1$ | $C(R^2)_2$ |
| 168 | $NR^1$ | $P(=O)R^1$ | C=O |
| 169 | $NR^1$ | $P(=O)R^1$ | $NR^1$ |
| 170 | $NR^1$ | $P(=O)R^1$ | $PR^1$ |
| 171 | $NR^1$ | $P(=O)R^1$ | $P(=O)R^1$ |
| 172 | $NR^1$ | $P(=O)R^1$ | O |
| 173 | $NR^1$ | $P(=O)R^1$ | S |
| 174 | $NR^1$ | O | $C(R^2)_2$ |

-continued

| | X¹ | X² | X³ |
|---|---|---|---|
| 175 | NR¹ | O | C=O |
| 176 | NR¹ | O | NR¹ |
| 177 | NR¹ | O | PR¹ |
| 178 | NR¹ | O | P(=O)R¹ |
| 179 | NR¹ | O | O |
| 180 | NR¹ | O | S |
| 181 | NR¹ | S | C(R²)₂ |
| 182 | NR¹ | S | C=O |
| 183 | NR¹ | S | NR¹ |
| 184 | NR¹ | S | PR¹ |
| 185 | NR¹ | S | P(=O)R¹ |
| 186 | NR¹ | S | O |
| 187 | NR¹ | S | S |
| 188 | PR¹ | C(R²)₂ | C(R²)₂ |
| 189 | PR¹ | C(R²)₂ | C=O |
| 190 | PR¹ | C(R²)₂ | NR¹ |
| 191 | PR¹ | C(R²)₂ | PR¹ |
| 192 | PR¹ | C(R²)₂ | P(=O)R¹ |
| 193 | PR¹ | C(R²)₂ | O |
| 194 | PR¹ | C(R²)₂ | S |
| 195 | PR¹ | C=O | C(R²)₂ |
| 196 | PR¹ | C=O | C=O |
| 197 | PR¹ | C=O | NR¹ |
| 198 | PR¹ | C=O | PR¹ |
| 199 | PR¹ | C=O | P(=O)R¹ |
| 200 | PR¹ | C=O | O |
| 201 | PR¹ | C=O | S |
| 202 | PR¹ | NR¹ | C(R²)₂ |
| 203 | PR¹ | NR¹ | C=O |
| 204 | PR¹ | NR¹ | NR¹ |
| 205 | PR¹ | NR¹ | PR¹ |
| 206 | PR¹ | NR¹ | P(=O)R¹ |
| 207 | PR¹ | NR¹ | O |
| 208 | PR¹ | NR¹ | S |
| 209 | PR¹ | PR¹ | C(R²)₂ |
| 210 | PR¹ | PR¹ | C=O |
| 211 | PR¹ | PR¹ | NR¹ |
| 212 | PR¹ | PR¹ | P(=O)R¹ |
| 213 | PR¹ | PR¹ | O |
| 214 | PR¹ | PR¹ | S |
| 215 | PR¹ | P(=O)R¹ | C(R²)₂ |
| 216 | PR¹ | P(=O)R¹ | C=O |
| 217 | PR¹ | P(=O)R¹ | NR¹ |
| 218 | PR¹ | P(=O)R¹ | PR¹ |
| 219 | PR¹ | P(=O)R¹ | P(=O)R¹ |
| 220 | PR¹ | P(=O)R¹ | O |
| 221 | PR¹ | P(=O)R¹ | S |
| 222 | PR¹ | O | C(R²)₂ |
| 223 | PR¹ | O | C=O |
| 224 | PR¹ | O | NR¹ |
| 225 | PR¹ | O | PR¹ |
| 226 | PR¹ | O | P(=O)R¹ |
| 227 | PR¹ | O | O |
| 228 | PR¹ | O | S |
| 229 | PR¹ | S | C(R²)₂ |
| 230 | PR¹ | S | C=O |
| 231 | PR¹ | S | NR¹ |
| 232 | PR¹ | S | PR¹ |
| 233 | PR¹ | S | P(=O)R¹ |
| 234 | PR¹ | S | O |
| 235 | PR¹ | S | S |
| 236 | P(=O)R¹ | C(R²)₂ | C(R²)₂ |
| 237 | P(=O)R¹ | C(R²)₂ | C=O |
| 238 | P(=O)R¹ | C(R²)₂ | NR¹ |
| 239 | P(=O)R¹ | C(R²)₂ | PR¹ |
| 240 | P(=O)R¹ | C(R²)₂ | P(=O)R¹ |
| 241 | P(=O)R¹ | C(R²)₂ | O |
| 242 | P(=O)R¹ | C(R²)₂ | S |
| 243 | P(=O)R¹ | C=O | C(R²)₂ |
| 244 | P(=O)R¹ | C=O | C=O |
| 245 | P(=O)R¹ | C=O | NR¹ |
| 246 | P(=O)R¹ | C=O | PR¹ |
| 247 | P(=O)R¹ | C=O | P(=O)R¹ |
| 248 | P(=O)R¹ | C=O | O |
| 249 | P(=O)R¹ | C=O | S |
| 250 | P(=O)R¹ | NR¹ | C(R²)₂ |
| 251 | P(=O)R¹ | NR¹ | C=O |
| 252 | P(=O)R¹ | NR¹ | NR¹ |
| 253 | P(=O)R¹ | NR¹ | PR¹ |
| 254 | P(=O)R¹ | NR¹ | P(=O)R¹ |
| 255 | P(=O)R¹ | NR¹ | O |
| 256 | P(=O)R¹ | NR¹ | S |
| 257 | P(=O)R¹ | PR¹ | C(R²)₂ |
| 258 | P(=O)R¹ | PR¹ | C=O |
| 259 | P(=O)R¹ | PR¹ | NR¹ |
| 260 | P(=O)R¹ | PR¹ | PR¹ |
| 261 | P(=O)R¹ | PR¹ | P(=O)R¹ |
| 262 | P(=O)R¹ | PR¹ | O |
| 263 | P(=O)R¹ | PR¹ | S |
| 264 | P(=O)R¹ | P(=O)R¹ | C(R²)₂ |
| 265 | P(=O)R¹ | P(=O)R¹ | C=O |
| 266 | P(=O)R¹ | P(=O)R¹ | NR¹ |
| 267 | P(=O)R¹ | P(=O)R¹ | PR¹ |
| 268 | P(=O)R¹ | P(=O)R¹ | O |
| 269 | P(=O)R¹ | P(=O)R¹ | S |
| 270 | P(=O)R¹ | O | C(R²)₂ |
| 271 | P(=O)R¹ | O | C=O |
| 272 | P(=O)R¹ | O | NR¹ |
| 273 | P(=O)R¹ | O | PR¹ |
| 274 | P(=O)R¹ | O | P(=O)R¹ |
| 275 | P(=O)R¹ | O | O |
| 276 | P(=O)R¹ | O | S |
| 277 | P(=O)R¹ | S | C(R²)₂ |
| 278 | P(=O)R¹ | S | C=O |
| 279 | P(=O)R¹ | S | NR¹ |
| 280 | P(=O)R¹ | S | PR¹ |
| 281 | P(=O)R¹ | S | P(=O)R¹ |
| 282 | P(=O)R¹ | S | O |
| 283 | P(=O)R¹ | S | S |
| 284 | O | C(R²)₂ | C(R²)₂ |
| 285 | O | C(R²)₂ | C=O |
| 286 | O | C(R²)₂ | NR¹ |
| 287 | O | C(R²)₂ | PR¹ |
| 288 | O | C(R²)₂ | P(=O)R¹ |
| 289 | O | C(R²)₂ | O |
| 290 | O | C(R²)₂ | S |
| 291 | O | C=O | C(R²)₂ |
| 292 | O | C=O | C=O |
| 293 | O | C=O | NR¹ |
| 294 | O | C=O | PR¹ |
| 295 | O | C=O | P(=O)R¹ |
| 296 | O | C=O | O |
| 297 | O | C=O | S |
| 298 | O | NR¹ | C(R²)₂ |
| 299 | O | NR¹ | C=O |
| 300 | O | NR¹ | NR¹ |
| 301 | O | NR¹ | PR¹ |
| 302 | O | NR¹ | P(=O)R¹ |
| 303 | O | NR¹ | O |
| 304 | O | NR¹ | S |
| 305 | O | PR¹ | C(R²)₂ |
| 306 | O | PR¹ | C=O |
| 307 | O | PR¹ | NR¹ |
| 308 | O | PR¹ | PR¹ |
| 309 | O | PR¹ | P(=O)R¹ |
| 310 | O | PR¹ | O |
| 311 | O | PR¹ | S |
| 312 | O | P(=O)R¹ | C(R²)₂ |
| 313 | O | P(=O)R¹ | C=O |
| 314 | O | P(=O)R¹ | NR¹ |
| 315 | O | P(=O)R¹ | PR¹ |
| 316 | O | P(=O)R¹ | P(=O)R¹ |
| 317 | O | P(=O)R¹ | O |
| 318 | O | P(=O)R¹ | S |
| 319 | O | O | C(R²)₂ |
| 320 | O | O | C=O |
| 321 | O | O | NR¹ |
| 322 | O | O | PR¹ |
| 323 | O | O | P(=O)R¹ |
| 324 | O | O | S |
| 325 | O | S | C(R²)₂ |
| 326 | O | S | C=O |
| 327 | O | S | NR¹ |
| 328 | O | S | PR¹ |

| | X¹ | X² | X³ |
|---|---|---|---|
| 329 | O | S | P(=O)R¹ |
| 330 | O | S | O |
| 331 | O | S | S |
| 332 | S | C(R²)₂ | C(R²)₂ |
| 333 | S | C(R²)₂ | C=O |
| 334 | S | C(R²)₂ | NR¹ |
| 335 | S | C(R²)₂ | PR¹ |
| 336 | S | C(R²)₂ | P(=O)R¹ |
| 337 | S | C(R²)₂ | O |
| 338 | S | C(R²)₂ | S |
| 339 | S | C=O | C(R²)₂ |
| 340 | S | C=O | C=O |
| 341 | S | C=O | NR¹ |
| 342 | S | C=O | PR¹ |
| 343 | S | C=O | P(=O)R¹ |
| 344 | S | C=O | O |
| 345 | S | C=O | S |
| 346 | S | NR¹ | C(R²)₂ |
| 347 | S | NR¹ | C=O |
| 348 | S | NR¹ | NR¹ |
| 349 | S | NR¹ | PR¹ |
| 350 | S | NR¹ | P(=O)R¹ |
| 351 | S | NR¹ | O |
| 352 | S | NR¹ | S |
| 353 | S | PR¹ | C(R²)₂ |
| 354 | S | PR¹ | C=O |
| 355 | S | PR¹ | NR¹ |
| 356 | S | PR¹ | PR¹ |
| 357 | S | PR¹ | P(=O)R¹ |
| 358 | S | PR¹ | O |
| 359 | S | PR¹ | S |
| 360 | S | P(=O)R¹ | C(R²)₂ |
| 361 | S | P(=O)R¹ | C=O |
| 362 | S | P(=O)R¹ | NR¹ |
| 363 | S | P(=O)R¹ | PR¹ |
| 364 | S | P(=O)R¹ | P(=O)R¹ |
| 365 | S | P(=O)R¹ | O |
| 366 | S | P(=O)R¹ | S |
| 367 | S | O | C(R²)₂ |
| 368 | S | O | C=O |
| 369 | S | O | NR¹ |
| 370 | S | O | PR¹ |
| 371 | S | O | P(=O)R¹ |
| 372 | S | O | O |
| 373 | S | O | S |
| 374 | S | S | C(R²)₂ |
| 375 | S | S | C=O |
| 376 | S | S | NR¹ |
| 377 | S | S | PR¹ |
| 378 | S | S | P(=O)R¹ |
| 379 | S | S | O |

Preferred embodiments of the compounds of the formula (Ia) according to the invention furthermore conform to the following formulae (Ia-1) to (Ia-10)

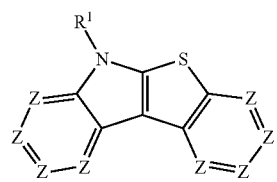

formula (Ia-1)

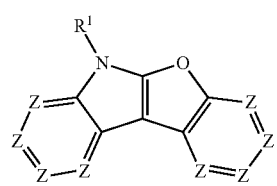

formula (Ia-2)

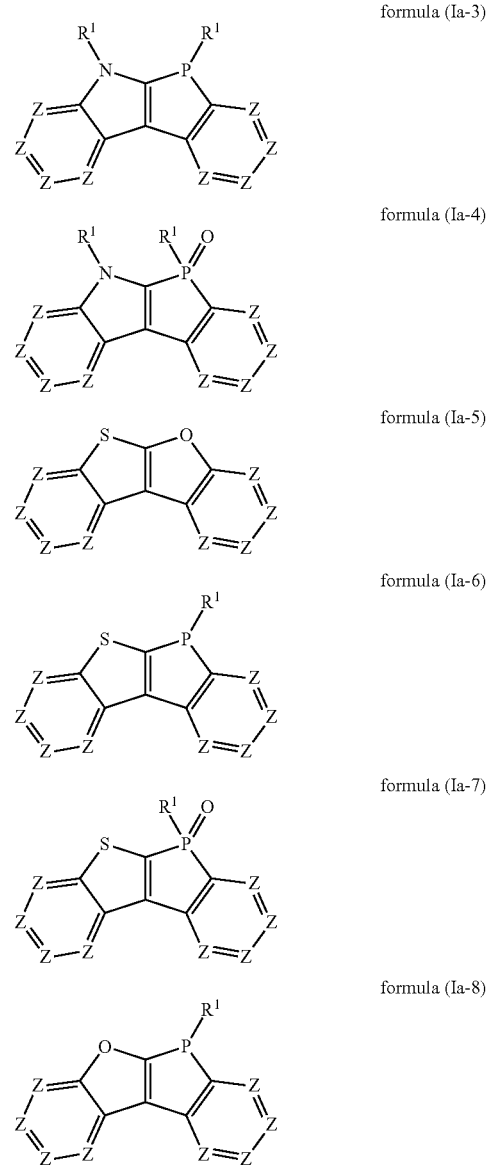

where the groups Z and R¹ are as defined above.

Preferred embodiments of the compounds of the formula (Ib) according to the invention furthermore conform to the following formulae (Ib-1) to (Ib-20)

formula (Ib-1)
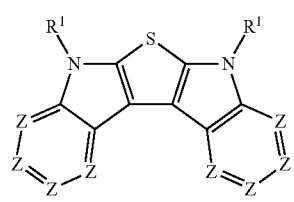
formula (Ib-2)
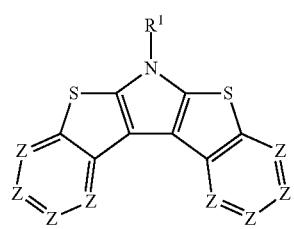
formula (Ib-3)
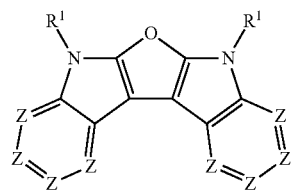
formula (Ib-4)
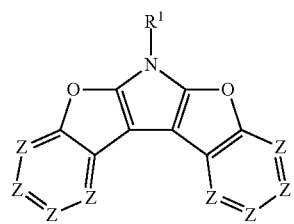
formula (Ib-5)
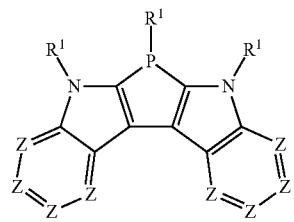
formula (Ib-6)
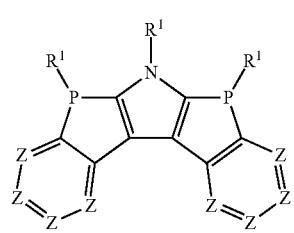
formula (Ib-7)
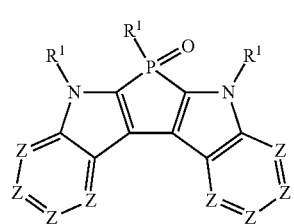
-continued
formula (Ib-8)
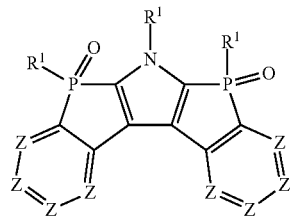
formula (Ib-9)
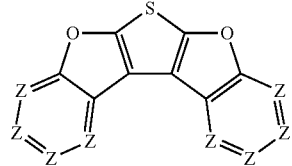
formula (Ib-10)
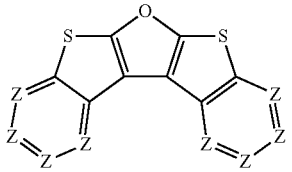
formula (Ib-11)
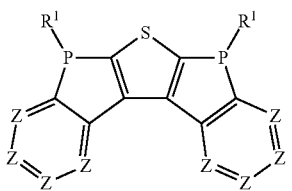
formula (Ib-12)
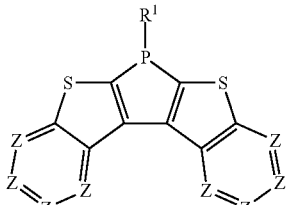
formula (Ib-13)
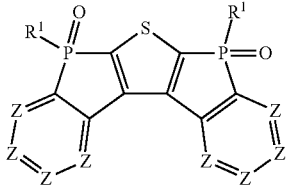
formula (Ib-14)
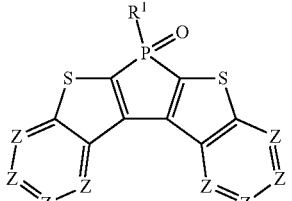
formula (Ib-15)
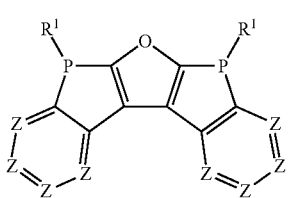

formula (Ib-16)

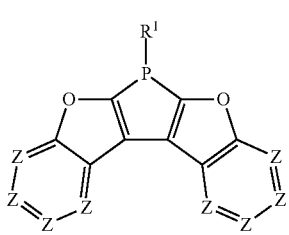

formula (Ib-17)

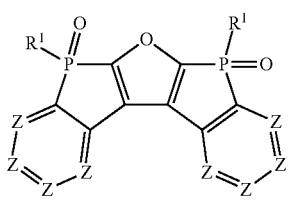

formula (Ib-18)

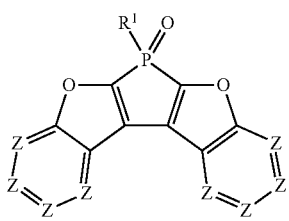

formula (Ib-19)

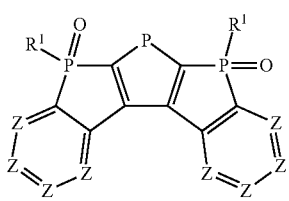

formula (Ib-20)

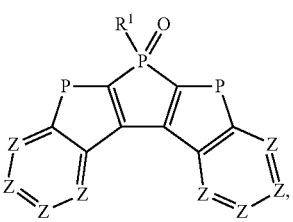

where the groups Z and $R^1$ are as defined above.

It is furthermore preferred in accordance with the invention for at least one of the groups $X^1$, $X^2$ and $X^3$ to represent a group $NR^1$.

It is furthermore preferred for compounds of the formula (I) where n=1 for the groups $X^1$ and $X^3$ to be identical.

It is again furthermore preferred for the compounds of the formulae (Ia-1) to (Ia-10) and (Ib-1) to (Ib-20) for Z to be equal to $CR^2$.

In a further preferred embodiment of the invention, $R^1$ is on each occurrence, identically or differently, an aromatic or heteroaromatic ring system having 5 to 30 aromatic ring atoms, which may in each case be substituted by one or more radicals $R^3$.

In a particularly preferred embodiment of the invention, $R^1$ is an aromatic or heteroaromatic ring system having 5 to 30 aromatic ring atoms, which may in each case be substituted by one or more radicals $R^3$.

It is furthermore preferred for the compounds for use in the electroluminescent devices according to the invention to carry, as substituent $R^1$ or $R^2$, at least one group which is selected from electron-deficient heteroaryl groups, aromatic or heteroaromatic ring systems having 10 to 30 aromatic ring atoms and from arylamine groups, where the above-mentioned group may be substituted by one or more of the above-mentioned radicals.

The above-mentioned electron-deficient heteroaryl groups here are preferably selected from pyridine, pyrimidine, pyridazine, pyrazine, triazine and benzimidazole, each of which may be substituted by one or more of the radicals defined above.

The above-mentioned aromatic or heteroaromatic ring systems having 10 to 30 aromatic ring atoms are preferably selected from naphthyl, anthracenyl, phenanthrenyl, benzanthracenyl, pyrenyl, biphenyl, terphenyl and quaterphenyl, each of which may be substituted by one or more of the radicals defined above.

The above-mentioned arylamine groups are preferably groups of the following formula (A)

formula (A)

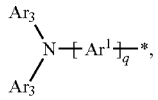

where the symbol * marks the bond to the remainder of the compound and furthermore $Ar^1$, $Ar^2$, $Ar^3$ represent, identically or differently on each occurrence, an aryl or heteroaryl group having 5 to 20 aromatic ring atoms, which may in each case be substituted by one or more radicals $R^3$ or $R^4$, $Ar^2$ and $Ar^3$ may be linked to one another by a single bond, and q is equal to 0, 1, 2, 3, 4 or 5.

In a further preferred embodiment of the invention, $R^2$ is on each occurrence, identically or differently, H, D, F, $C(=O)R^3$, CN, $Si(R^3)_3$, $N(R^3)_2$, a straight-chain alkyl or alkoxy group having 1 to 10 C atoms or a branched or cyclic alkyl or alkoxy group having 3 to 10 C atoms or an alkenyl or alkynyl group having 2 to 10 C atoms, where the above-mentioned groups may each be substituted by one or more radicals $R^3$ and where one or more non-adjacent $CH_2$ groups in the above-mentioned groups may be replaced by $-R^3C=CR^3-$, $-C\equiv C-$, $Si(R^3)_2$, $C=O$, $-C(=O)O-$, $-C(=O)NR^3-$, $NR^3$, $-O-$ or $-S-$ and where one or more H atoms in the above-mentioned groups may be replaced by D, F or CN, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$, where two or more radicals $R^2$ may be linked to one another and may form an aliphatic or aromatic ring.

In the above-mentioned case where two or more radicals $R^2$ are connected to one another, it is preferred for the two radicals to be a constituent of a moiety

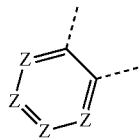

from formula (I) where Z is equal to $CR^2$. It is furthermore explicitly preferred for two radicals $R^2$ which are bonded to two adjacent C atoms on the aromatic or heteroaromatic six-membered ring to be connected to one another, for example in the following manner:

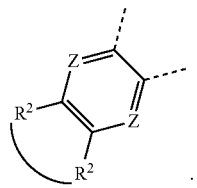

It is furthermore preferred in this case for the connection of the two groups to form a condensed aryl or heteroaryl group which has 4 to 8 aromatic ring atoms more than the original aryl or heteroaryl group.

In a further preferred embodiment of the invention, the two radicals $R^2$ of a group $X^1$, $X^2$ or $X^3$, which corresponds to $C(R^2)_2$, are connected to one another and form an aliphatic or aromatic ring. Preferred embodiments thereof are, inter alia, an aliphatic three-membered ring, four-membered ring, five-membered ring or six-membered ring, as depicted in the following formula. In the formula, the group X optionally stands for $X^1$, $X^2$ or $X^3$. The said rings may be substituted by one or more of the above-mentioned radicats and/or condensed onto further rings.

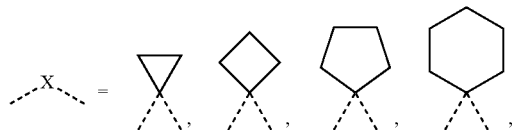

In a further preferred embodiment of the invention, $R^3$ is on each occurrence, identically or differently, H, D, F, $C(=O)R^4$, CN, $Si(R^4)_3$, $N(R^4)_2$, a straight-chain alkyl or alkoxy group having 1 to 10 C atoms or a branched or cyclic alkyl or alkoxy group having 3 to 10 C atoms or an alkenyl or alkynyl group having 2 to 10 C atoms, where the above-mentioned groups may each be substituted by one or more radicals $R^4$ and where one or more non-adjacent $CH_2$ groups in the above-mentioned groups may be replaced by $-R^4C=CR^4-$, $-C\equiv C-$, $Si(R^4)_2$, $C=O$, $-C(=O)O-$, $-C(=O)NR^4-$, $NR^4$, $-O-$ or $-S-$ and where one or more H atoms in the above-mentioned groups may be replaced by D, F or CN, or an aromatic or heteroaromatic ring system having 5 to 30 aromatic ring atoms, which may in each case be substituted by one or more radicals $R^4$, or an aryloxy or heteroaryloxy group having 5 to 30 aromatic ring atoms, which may be substituted by one or more radicals $R^4$, where two or more radicals $R^3$ may be linked to one another and may form an aliphatic or aromatic ring.

Examples of compounds according to the invention are shown below.

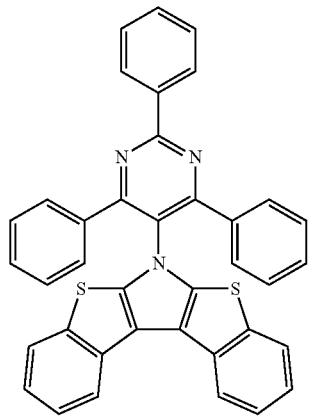

1

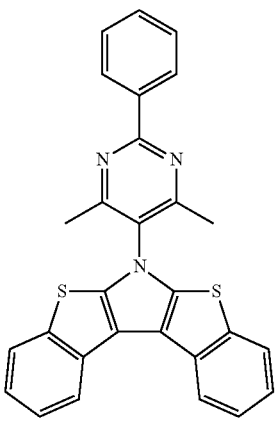

2

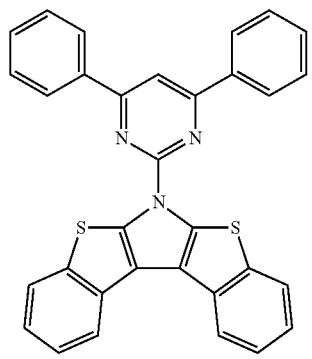

3

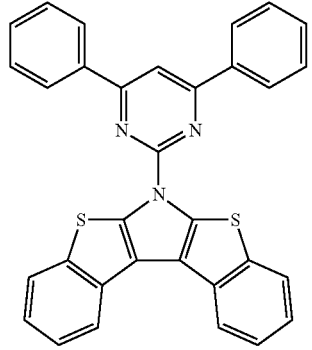

4

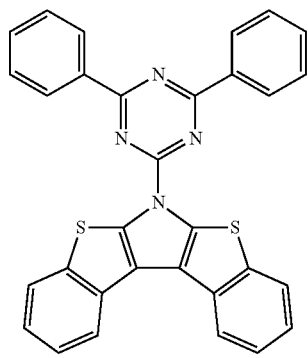
5
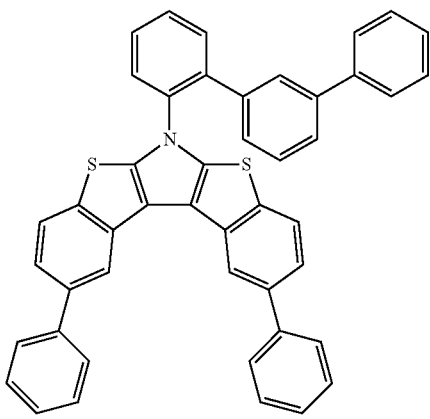
9
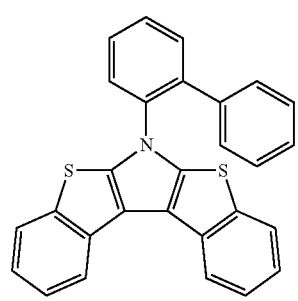
6
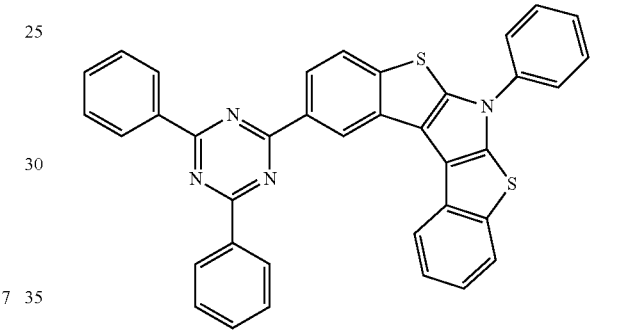
10
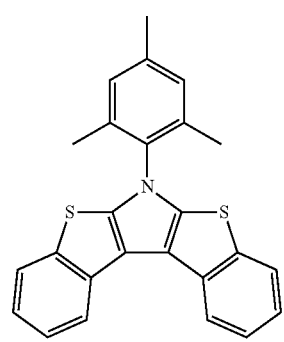
7
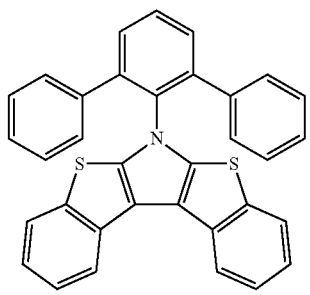
11
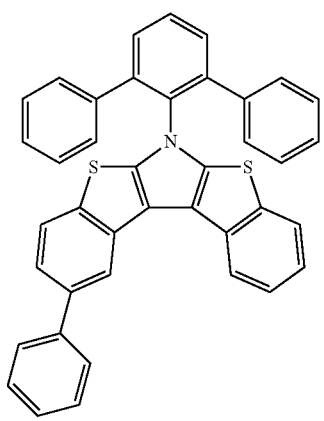
8
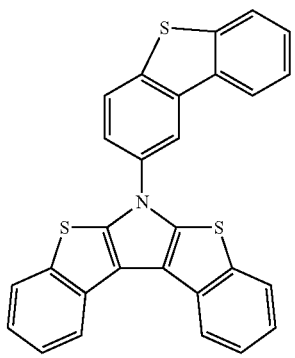
12

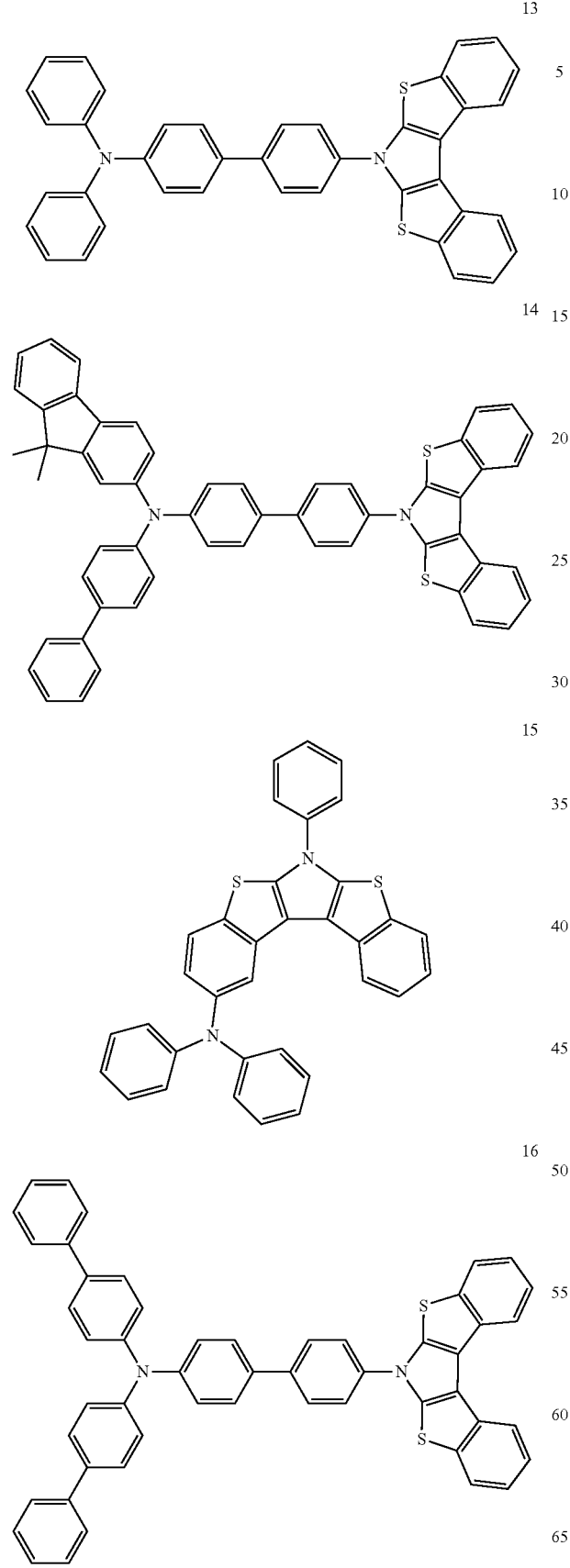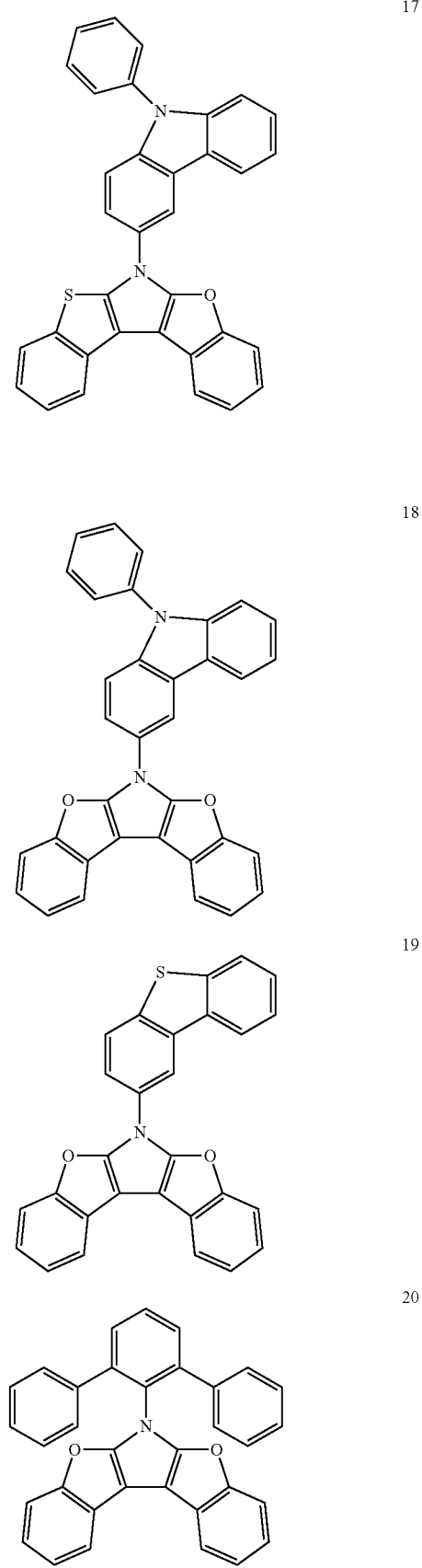

21
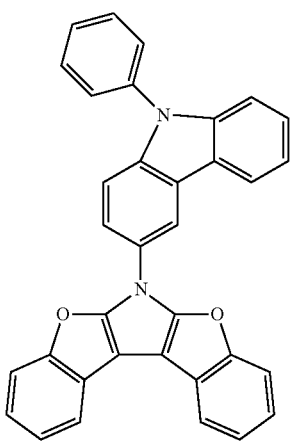
22
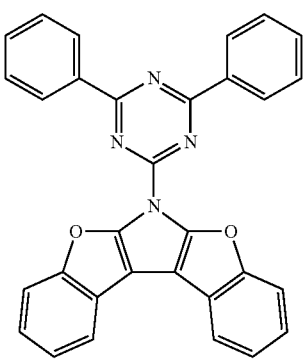
23
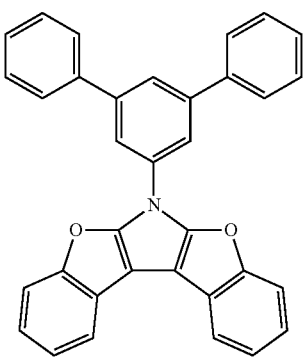
24
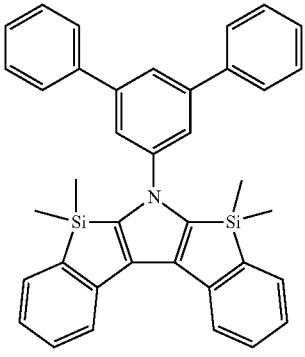
25
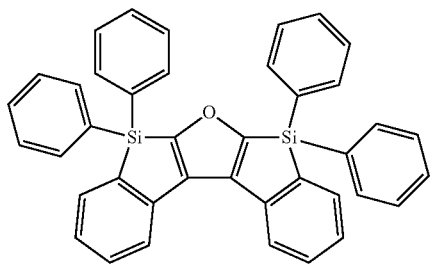
26
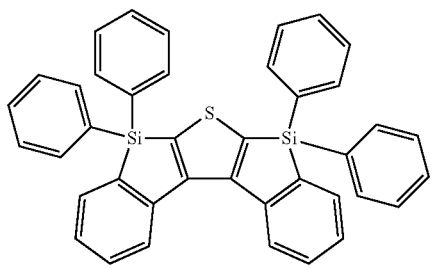
27
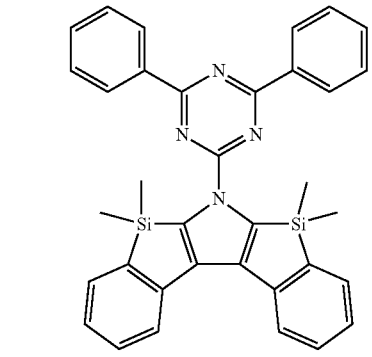
28
29
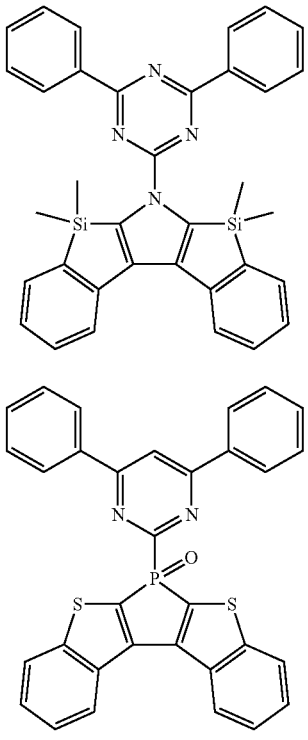

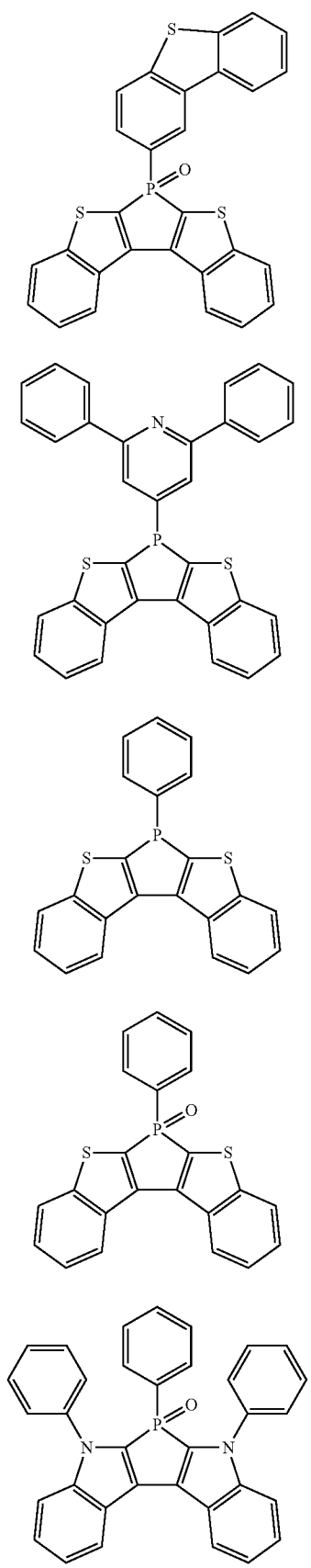
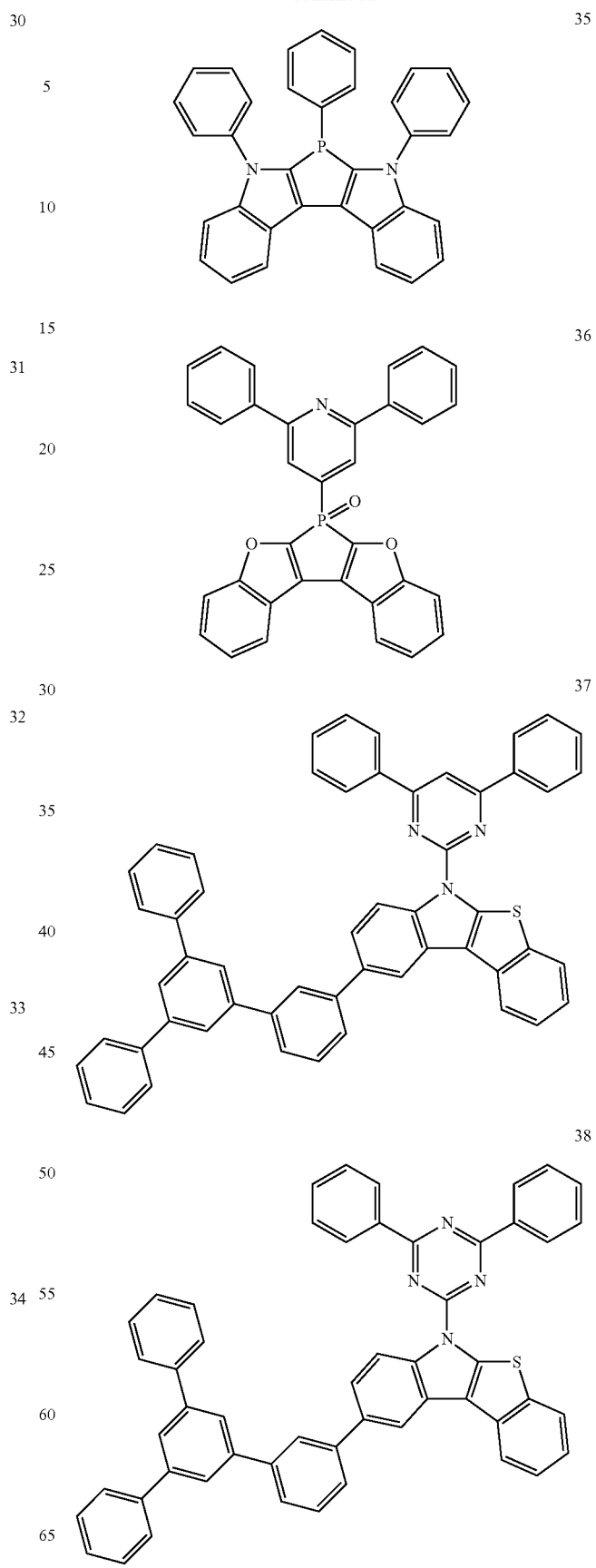

-continued
39
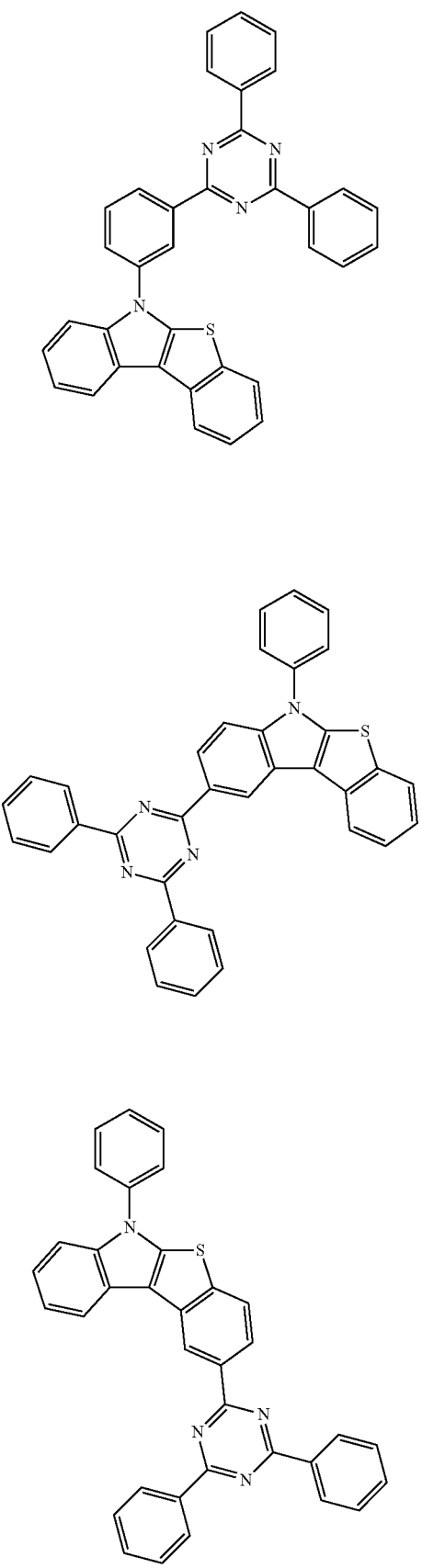
40
41
-continued
42
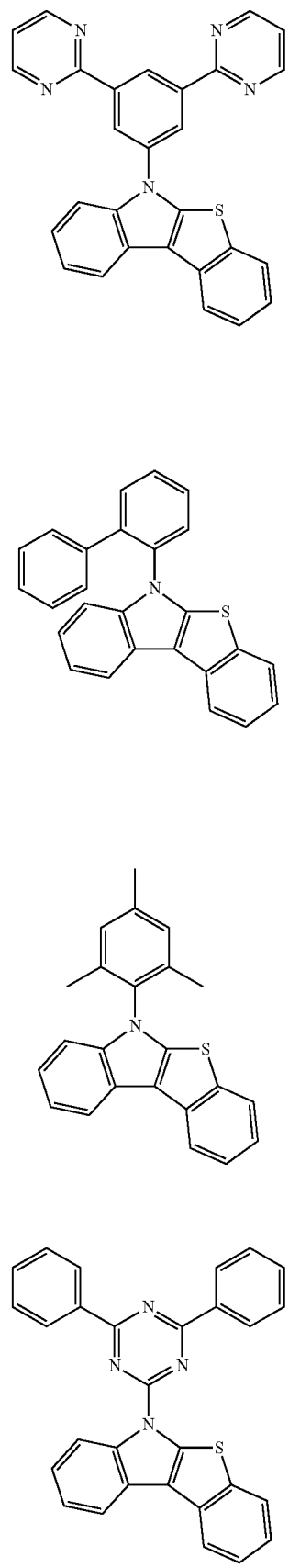
43
44
45

46
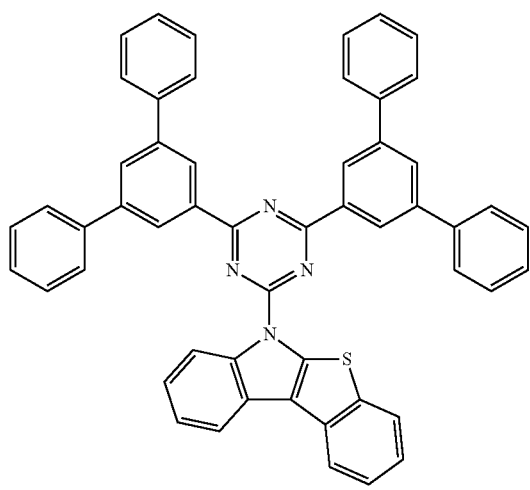
47
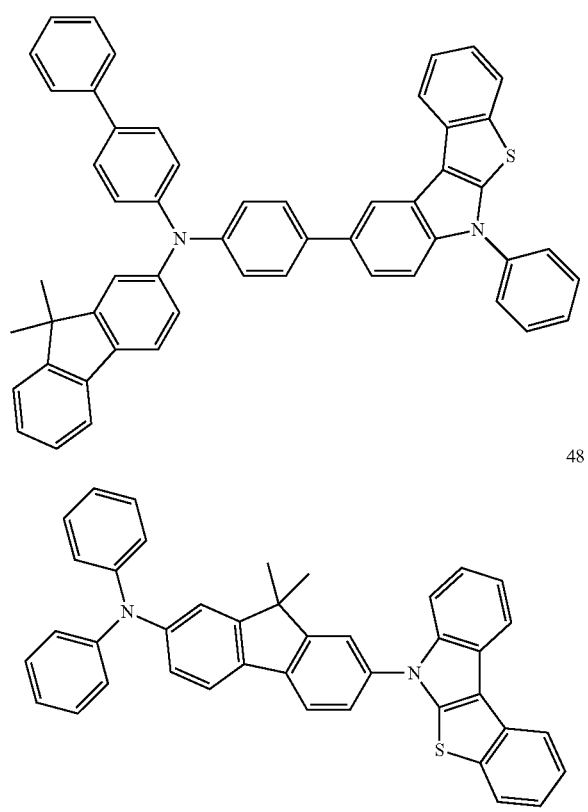
48
49
50
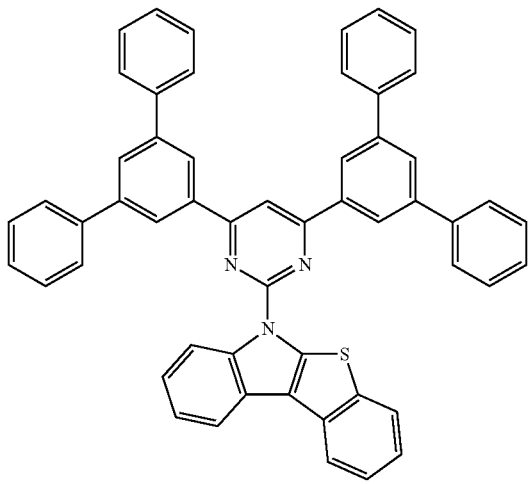
51
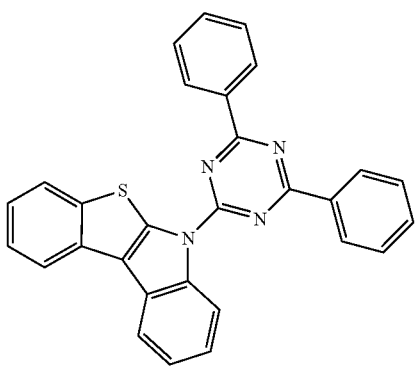
52
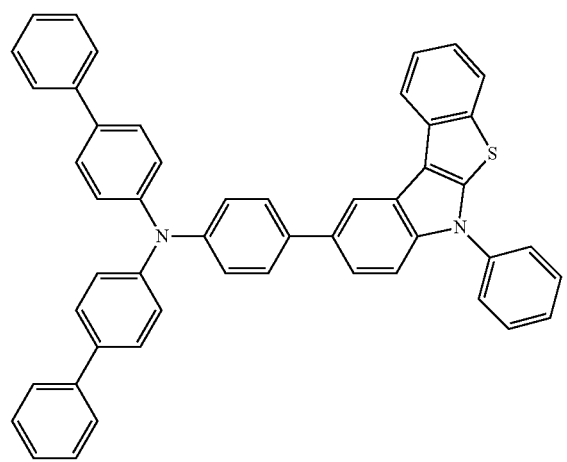

-continued
53
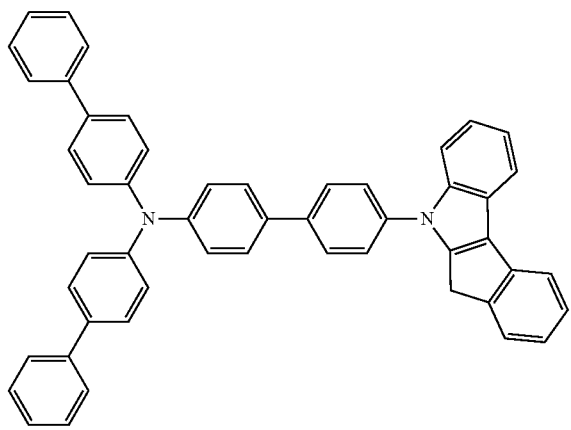
54
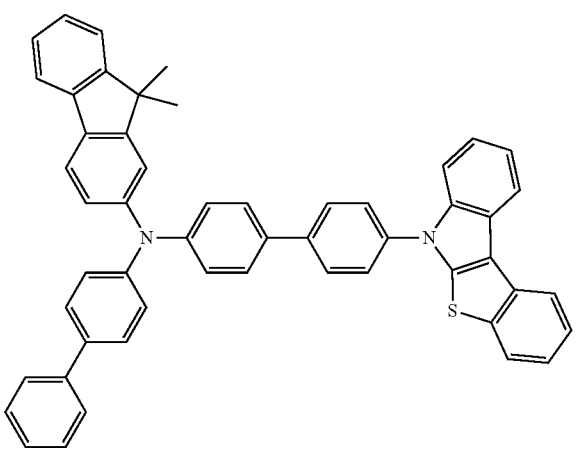
55
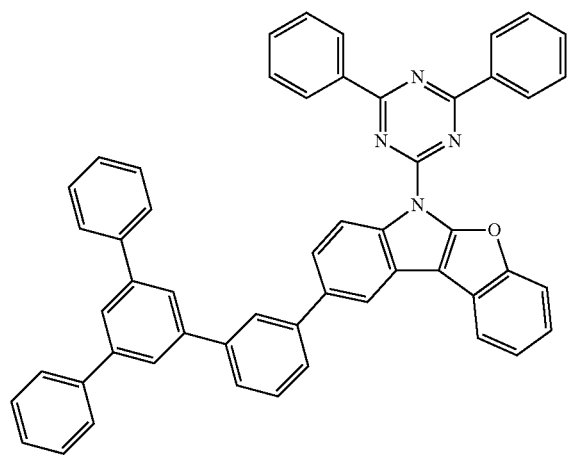
-continued
56
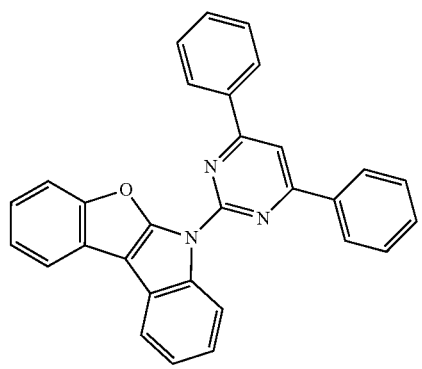
57
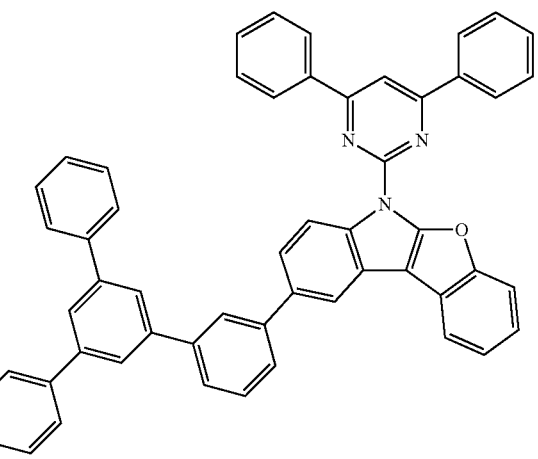
58
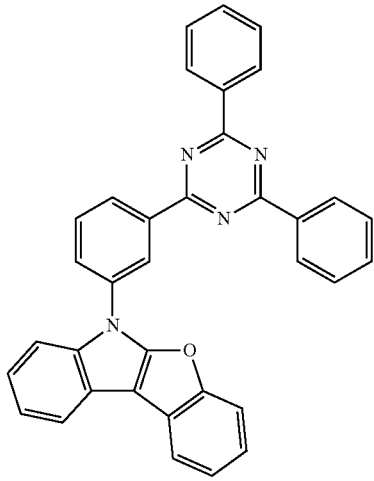

59
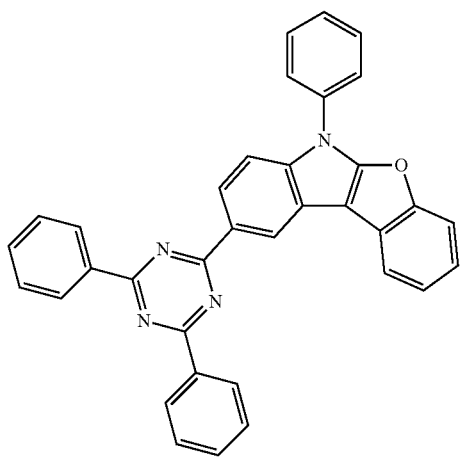
60
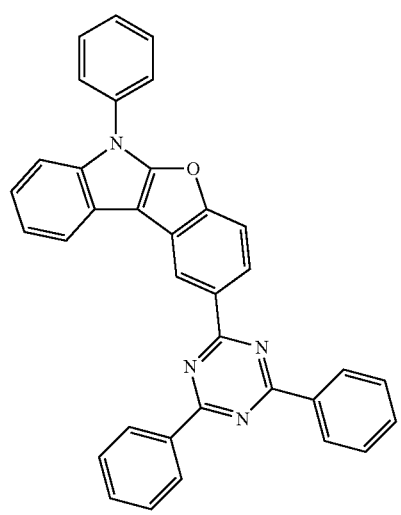
61
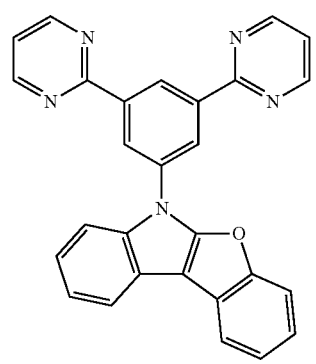
62
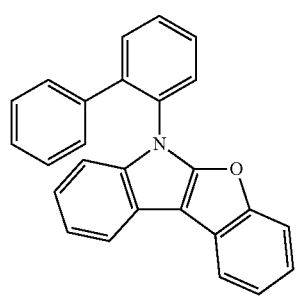
63
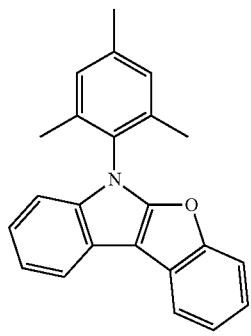
64
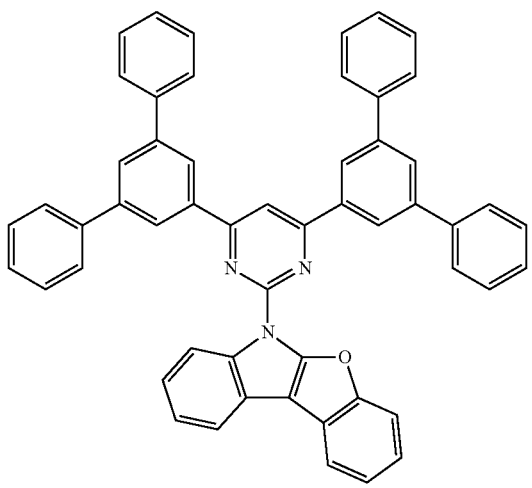
65
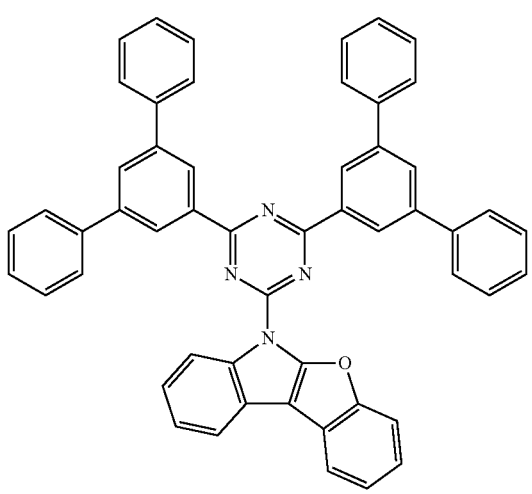

66

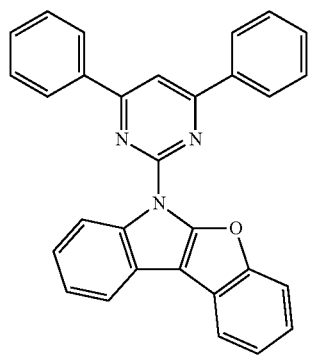

67

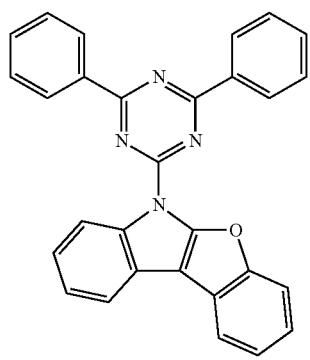

68

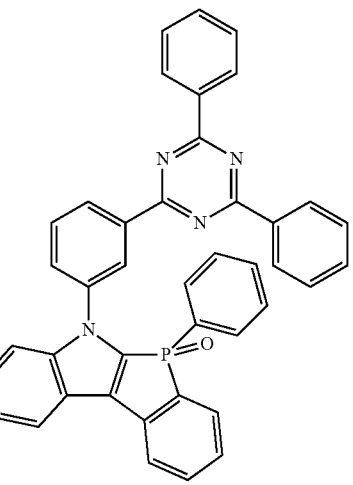

69

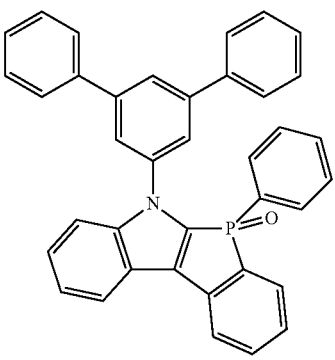

70

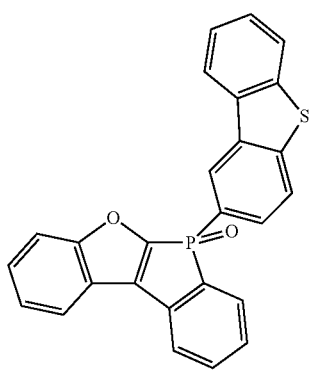

The compounds of the formula (I) according to the invention can be prepared by known organochemical synthetic processes. These include, for example, bromination, Suzuki coupling and Hartwig-Buchwald coupling, inter alia.

The person skilled in the art in the area of organic synthesis and in the area of functional materials for organic electroluminescent devices will be able to deviate from the illustrative synthetic routes shown below and/or modify individual steps in a suitable manner if such action is advantageous.

Compounds according to the invention which contain two five-membered heteroaromatic rings which are condensed with one another can be obtained, for example, by the synthetic route shown in Scheme 1.

Scheme 1

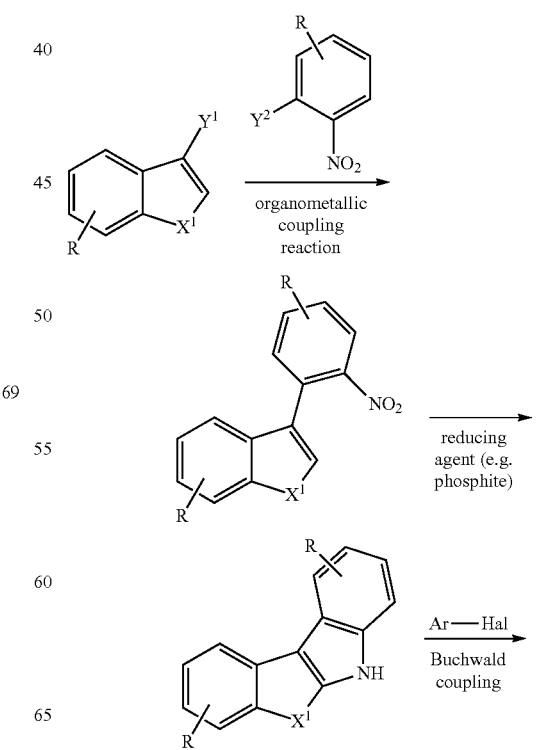

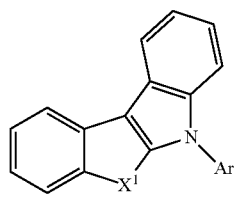

$Y^1$, $Y^2$ = leaving group for organomet. coupling, e.g. halide, boronic acid
R = organ. radical
Ar = aryl or heteroaryl group To this end, firstly an organometallic coupling reaction, preferably a Suzuki reaction, is carried out between a benzothiophene derivative or an analogous compound, such as, for example, a benzofuran derivative, and a nitrophenyl derivative. The nitro group is subsequently reduced, and a ring-closure reaction commences in which the second condensed-on five-membered heteroaromatic ring is formed as a pyrrole ring. The nitrogen atom of the pyrrole ring can finally be arylated in a Hartwig-Buchwald coupling.

Compounds according to the invention which contain three five-membered heteroaromatic rings which are condensed with one another can furthermore be obtained, for example, by the synthetic route shown in Scheme 2. This route likewise proceeds via a nitroaryl intermediate, which supplies the skeleton of the compounds according to the invention having three condensed five-membered aromatic rings via reduction and ring closure.

Scheme 2

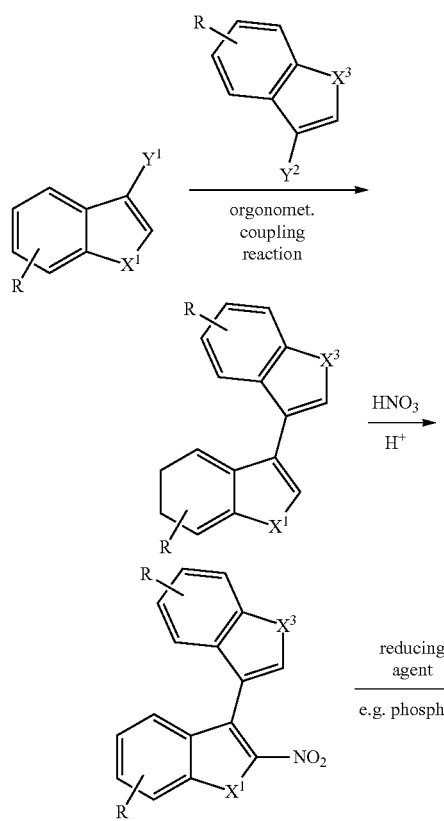

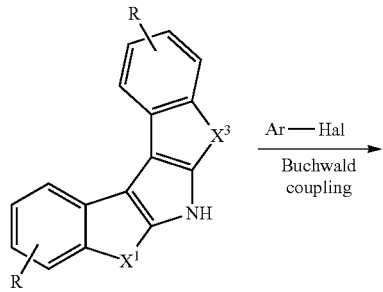

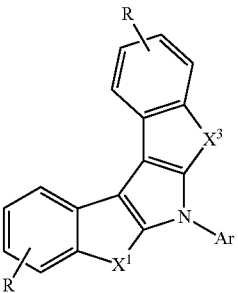

$Y^1$, $Y^2$ = leaving group for organomet. coupling, e.g. halide, boronic acid
R = organ. radical
Ar = aryl or heteroaryl group As an alternative to the route shown above, compounds according to the invention which contain three five-membered heteroaromatic rings which are condensed with one another can also be synthesised by the route shown in Scheme 3.

Scheme 3

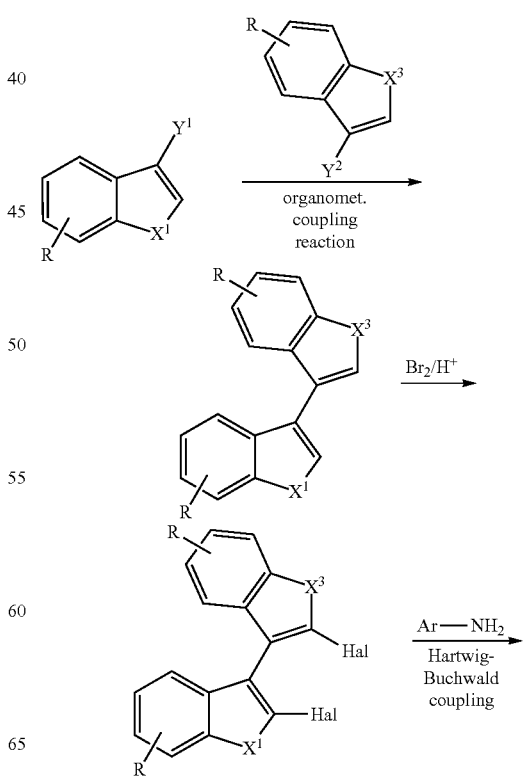

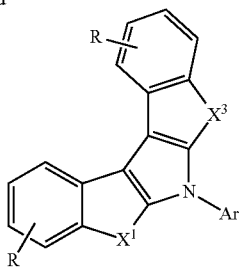

$Y^1$, $Y^2$ = leaving group for organomet. coupling, e.g. halide, boronic acid
R = organ. radical
Ar = aryl or heteroaryl group Starting from a benzothiophene derivative, a benzofuran derivative or an analogous compound, firstly an organometallic coupling reaction, preferably a Suzuki coupling, is carried out with a second corresponding heteroaryl compound. A double bromination, for example using elemental bromine, is subsequently carried out in the two positions in the α-position to the bond between the two heteroaryl groups. Finally, the third central heteroaromatic five-membered ring is closed by a Hartwig-Buchwald coupling to a primary arylamine or heteroarylamine.

The present invention thus furthermore relates to a process for the preparation of a compound of the formula (I), characterised in that one or more condensed heteroaromatic five-membered rings are formed by a ring-closure reaction.

The compounds according to the invention described above, in particular compounds which are substituted by reactive leaving groups, such as bromine, iodine, boronic acid or boronic acid ester, can be used as monomers for the preparation of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (I), where the bond(s) to the polymer, oligomer or dendrimer may be localised at any desired positions in formula (I) substituted by $R^1$ or $R^2$. Depending on the linking of the compound of the formula (I), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (I) may, for example, be linked via a trivalent or polyvalent group, for example via a trivalent or polyvalent aromatic or heteroaromatic group, to give a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006,383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The polymers, oligomers and dendrimers usually also contain further units, for example emitting (fluorescent or phosphorescent) units, such as, for example, vinyltriarylamines (for example in accordance with WO 07/068325) or phosphorescent metal complexes (for example in accordance with WO 06/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 02/067343 A1 and WO 2005/026144 A1.

The processing of the compounds according to the invention from the liquid phase, for example by spin coating or by printing processes, requires formulations of the compounds according to the invention. These formulations can be, for example, solutions, dispersions or mini-emulsions. It may be preferred to use mixtures of two or more solvents for this purpose. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The invention therefore furthermore relates to a formulation, in particular a solution, dispersion or mini-emulsion, comprising at least one compound of the formula (I) or at least one polymer, oligomer or dendrimer containing at least one unit of the formula (I) and at least one solvent, preferably an organic solvent. The way in which solutions of this type can be prepared is known to the person skilled in the art and is described, for example, in WO 2002/072714, WO 2003/019694 and the literature cited therein.

The compounds of the formula (I) according to the invention are suitable for use in electronic devices, in particular in organic electroluminescent devices (OLEDs). Depending on the substitution, the compounds are employed in various functions and layers.

For example, compounds of the formula (I) which contain electron-deficient groups, such as six-membered ring heteroaryl groups having one or more nitrogen atoms or five-membered ring heteroaryl groups having two or more nitrogen atoms, are particularly suitable for use as matrix material for phosphorescent dopants, as electron-transport material or as hole-blocking material.

Furthermore, compounds of the formula (I) which are substituted by aromatic ring systems, in particular by aromatic ring systems having 12 to 30 aromatic ring atoms, and/or by one or more arylamino groups are particularly suitable for use as hole-transport materials or for use as fluorescent dopants.

The compounds according to the invention are preferably employed as electron-transport material in an electron-transport layer, as matrix material in an emitting layer or as hole-transport material in a hole-transport layer. However, they can also be employed in other layers and/or functions, for example as fluorescent dopants in an emitting layer or as hole- or electron-blocking materials.

The invention therefore furthermore relates to the use of the compounds of the formula (I) according to the invention in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably selected from organic electroluminescent devices (OLEDs).

The invention again furthermore relates to electronic devices comprising at least one compound of the formula (I). The electronic devices here are preferably selected from the devices mentioned above. Particular preference is given to organic electroluminescent devices comprising an anode, a cathode and at least one emitting layer, characterised in that at least one organic layer, which may be an emitting layer, an electron-transport layer or another layer, comprises at least one compound of the formula (I).

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*), coupling-out layers and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where one or more of these layers may comprise at least one compound of the formula (I) and where the three layers exhibit blue, green and orange or red emission (for the basic structure see, for example, WO 05/011013). Likewise suitable in such systems for white emission are emitters which have broad-band emission bands and thus exhibit white emission. Alternatively and/or additionally, the compounds according to the invention may also be present in a hole-transport layer or electron-transport layer or in another layer in such systems.

It is preferred in accordance with the invention if the compound of the formula (I) is employed in an electronic device comprising one or more phosphorescent dopants. The compound here can be used in various layers, preferably in an electron-transport layer, a hole-transport layer, a hole-injection layer or in the emitting layer.

However, the compound of the formula (I) can also be employed in accordance with the invention in an electronic device comprising one or more fluorescent dopants and no phosphorescent dopants.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent diopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent dopants described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes without inventive step in combination with the compounds of the formula (I) according to the invention in organic electroluminescent devices.

Further examples of suitable phosphorescent dopants are revealed by the table in a later section.

In a preferred embodiment of the present invention, the compounds of the formula (I) are employed as matrix material in combination with one or more dopants, preferably phosphorescent dopants.

A dopant is taken to mean the component whose proportion in the mixture is the smaller in a system comprising a matrix material and a dopant. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a preferred embodiment of the invention, the compounds of the formula (I) are used as a component of mixed-matrix systems. The mixed-matrix systems preferably comprise two or three different matrix materials, particularly preferably two different matrix materials. Preferably, one of the two materials here is a material having hole-transporting properties and the other material is a material having electron-transporting properties. The two different matrix materials here may be present in a ratio of 1:50 to 1:1, preferably 1:20 to 1:1, particularly preferably 1:10 to 1:1 and very particularly preferably 1:4 to 1:1.

The mixed-matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Mixed-matrix systems are preferably employed in phosphorescent organic electroluminescent devices.

Particularly suitable matrix materials, which can be employed in combination with the compounds according to the invention as matrix components of a mixed-matrix system, are aromatic ketones, aromatic phosphine oxides or aromatic sulfoxides or sulfones, for example in accordance with WO 04/013080, WO 04/093207, WO 06/005627 or WO 10/006680, triarylamines, carbazole derivatives, for example CBP(N,N-biscarbazolylbiphenyl) or the carbazole derivatives disclosed in WO 05/039246, US 2005/0069729, JP 2004/288381, EP 1205527 or WO 08/086,851, indolocarbazole derivatives, for example in accordance with WO 07/063,754 or WO 08/056746, azacarbazole derivatives, for example in accordance with EP 1617710, EP 1617711, EP 1731584, JP 2005/347160, bipolar matrix materials, for example in accordance with WO 07/137,725, silanes, for example in accordance with WO 05/111172, azaboroles or boronic esters, for example in accordance with WO 06/117052, triazine derivatives, for example in accordance with WO 10/015,306, WO 07/063,754 or WO 08/056746, zinc complexes, for example in accordance with EP 652273 or WO 09/062,578, diazasilole or tetraazasilole derivatives, for example in accordance with WO 10/054,729, diazaphosphole derivatives, for example in accordance with WO 10/054,730, indenocarbazole derivatives, for example in accordance with WO 2010/136109 and WO 2011/000455, or bridged carbazoles, for example in accordance with the unpublished applications DE 102010005697.9 and DE 102010014933.0.

Preferred phosphorescent dopants for use in mixed-matrix systems comprising the compounds according to the invention are the phosphorescent dopants mentioned in the above table.

In a further preferred embodiment of the invention, the compounds of the formula (I) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. If the compounds of the formula (I) are used as hole-transport material, it may be preferred for them to be doped with electron-acceptor compounds, for example with $F_4$-TCNQ or with compounds as described in EP 1476881 or EP 1596445.

In a further preferred embodiment of the invention, a compound of the formula (I) is used as hole-transport material in combination with a hexaazatriphenylene derivative, as described in US 2007/0092755. The hexaazatriphenylene derivative is particularly preferably employed in its own layer here.

If the compound of the formula (I) is employed as hole-transport material in a hole-transport layer, the compound can be employed as pure material, i.e. in a proportion of 100%, in the hole-transport layer or it can be employed in combination with further compounds in the hole-transport layer.

In a further embodiment of the invention, the compounds of the formula (I) are employed as fluorescent dopants in an emitting layer. In particular, the compounds are suitable as fluorescent dopants if they are substituted by one or more aromatic systems, preferably aromatic systems containing 12 to 30 aromatic ring atoms. The compounds according to the invention are preferably used as green or blue emitters.

The proportion of the compound of the formula (I) as dopant in the mixture of the emitting layer is in this case between 0.1 and 50.0% by vol., preferably between 0.5 and 20.0% by vol., particularly preferably between 0.5 and 8.0% by vol. Correspondingly, the proportion of the matrix material is between 50.0 and 99.9% by vol., preferably between 80.0 and 99.5% by vol., particularly preferably between 92.0 and 99.5% by vol.

Preferred matrix materials for use in combination with the compounds according to the invention as fluorescent dopants are mentioned in one of the following sections. They correspond to the matrix materials for fluorescent dopants that are indicated as preferred.

In a further embodiment of the invention, the compounds are employed as electron-transport materials in an electron-transport layer of an organic electroluminescent device. In this case, it is preferred for the compounds according to the invention to have one or more electron-deficient groups, such as, for example, six-membered heteroaryl ring groups containing one or more, nitrogen atoms or five-membered heteroaryl ring groups containing two or more nitrogen atoms.

The electron-transport layer in the electroluminescent devices according to the invention may be doped. Suitable dopants are alkali metals or alkalimetal compounds, such as, for example, Liq (lithium quinolinate). In a preferred embodiment of the invention, the electron-transport layer is, in particular, doped if the electron-transport material is a benzimidazole derivative or a triazine derivative. The preferred dopant is then Liq.

It is furthermore a subject-matter of the present invention that the compounds according to the invention are employed as hole-blocking material. The compounds are then preferably employed in a hole-blocking layer, in particular in a phosphorescent OLED. A hole-blocking layer in the sense of this invention is a layer which is arranged between an emitting layer and an electron-transport layer.

The further functional materials preferably employed in the electronic devices comprising one or more compounds according to the invention are shown below.

Particularly suitable phosphorescent dopants are the compounds shown in the following table.

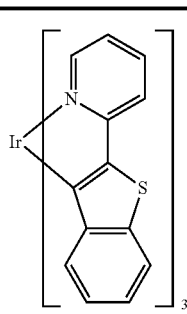

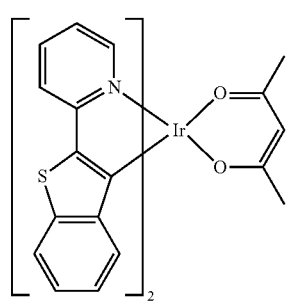

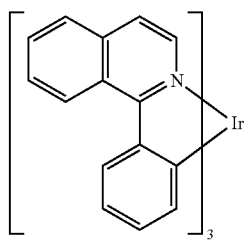

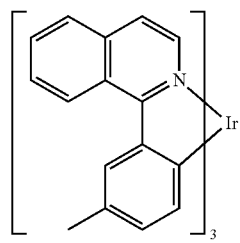

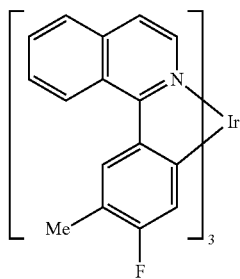

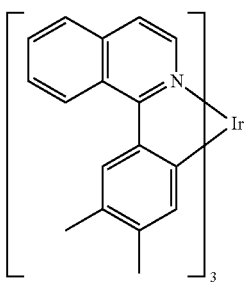

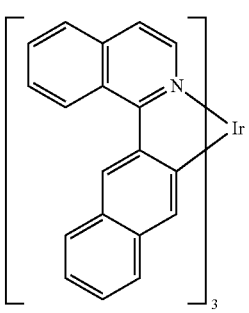

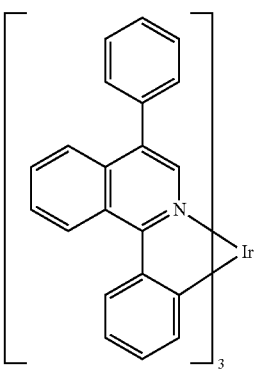

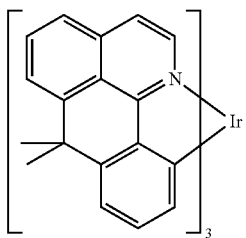
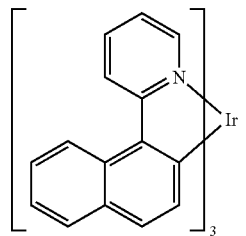
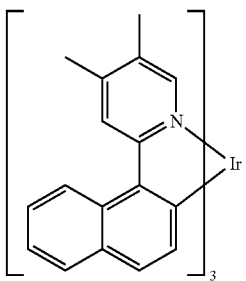
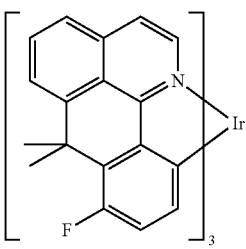
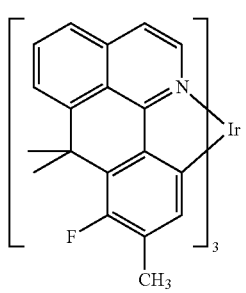
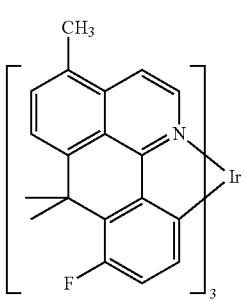
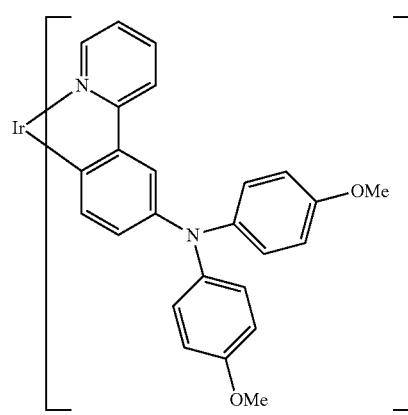
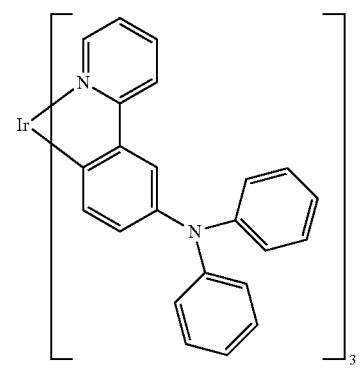
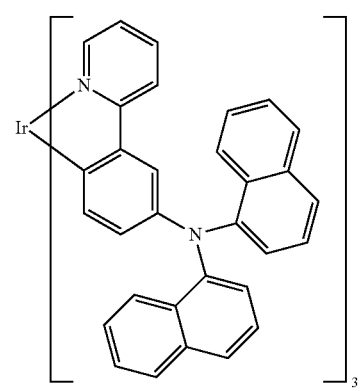
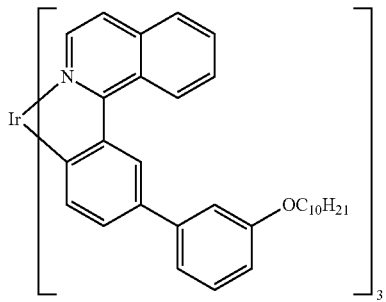

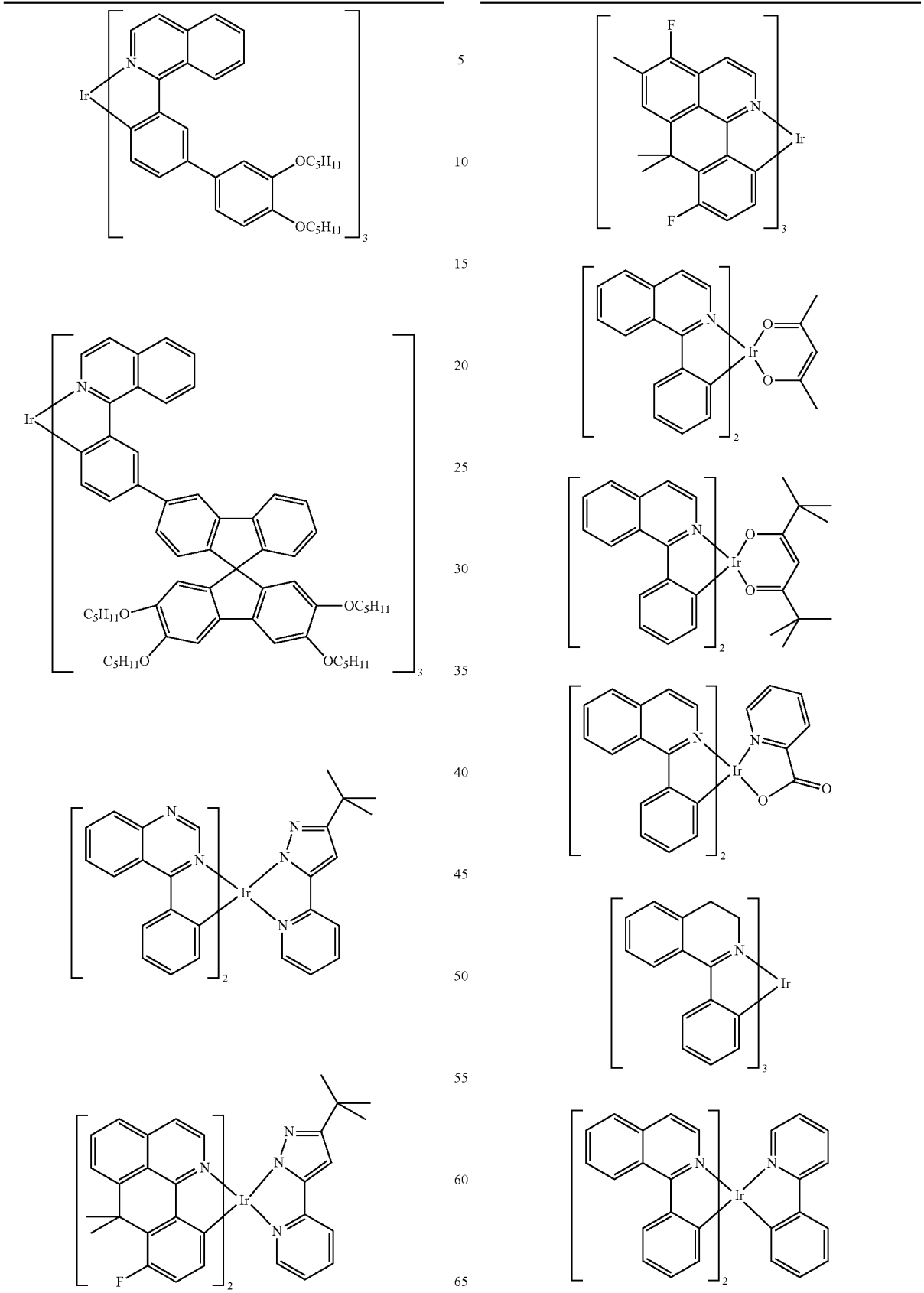

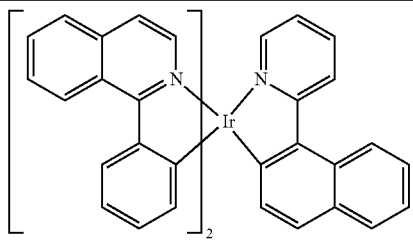
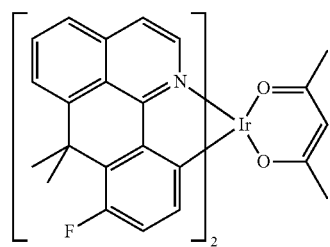
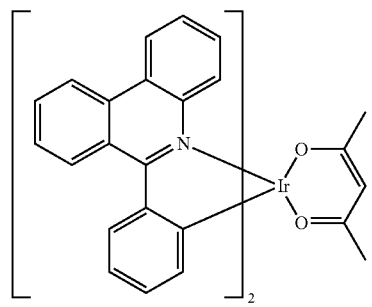
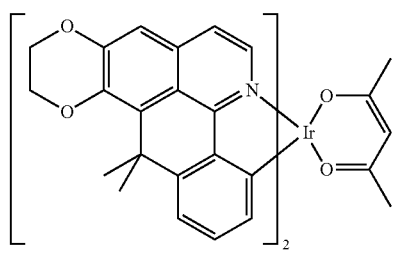
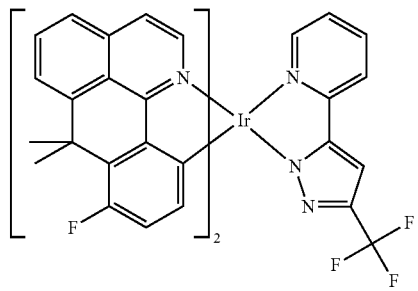
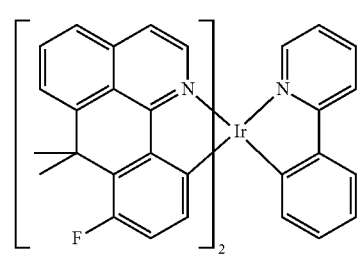
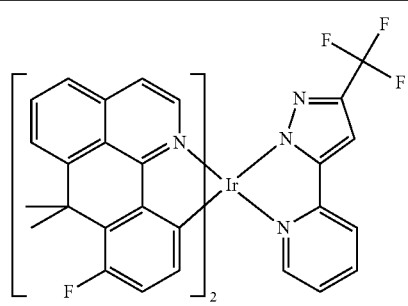
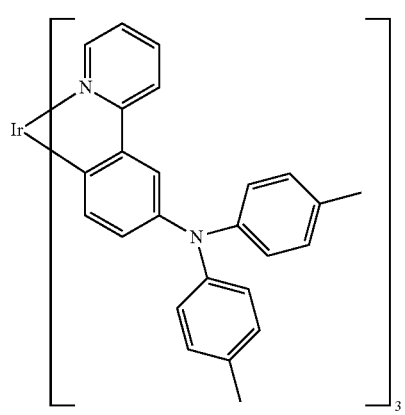
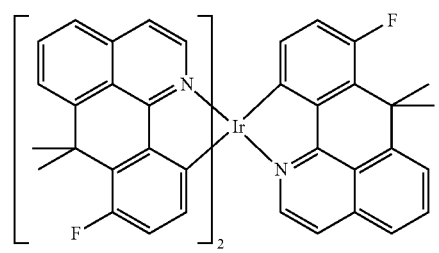
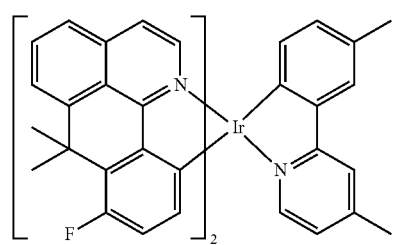
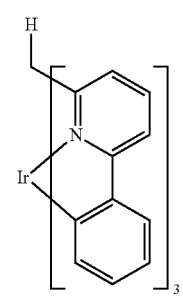

-continued
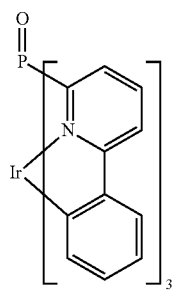
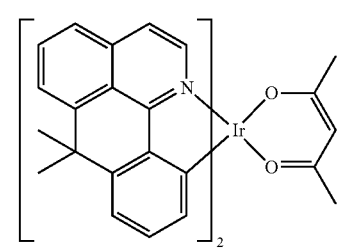
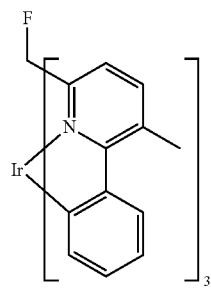
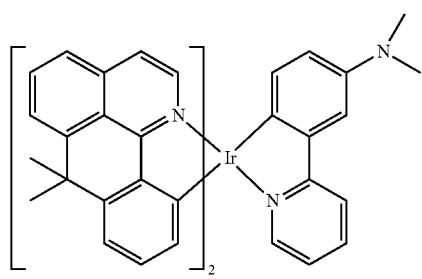
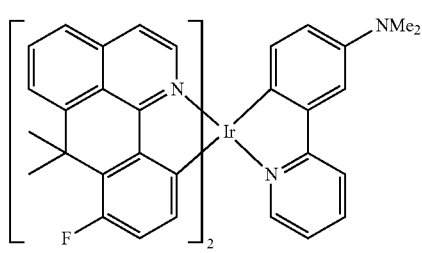
-continued
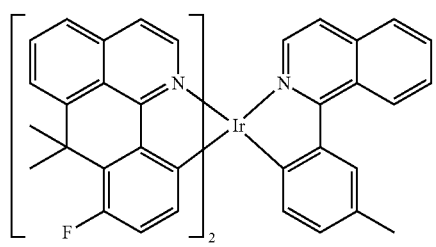
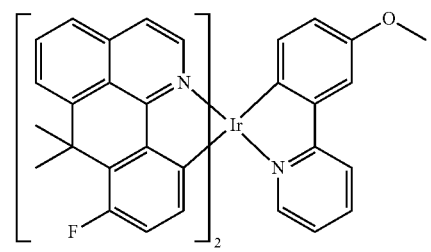
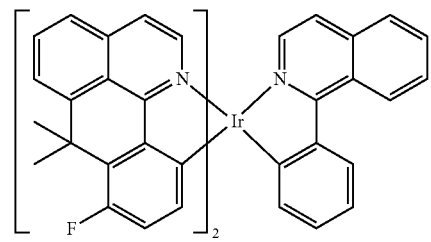
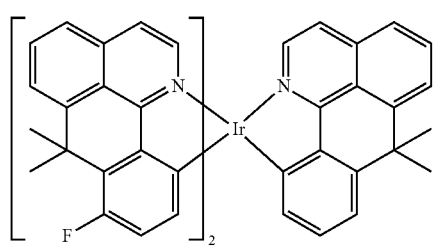
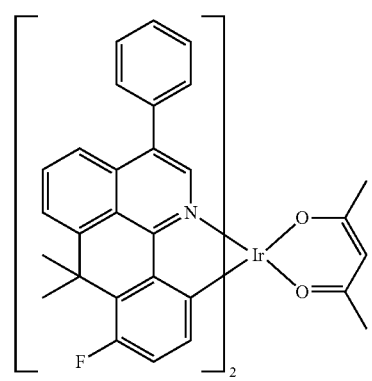

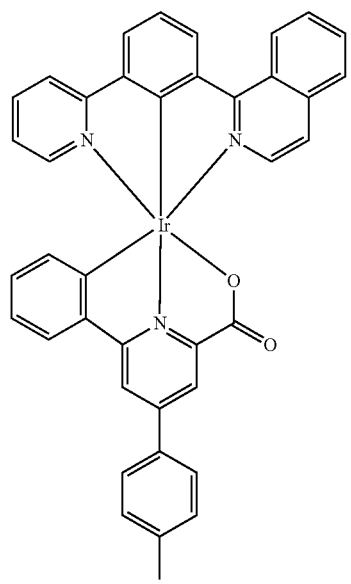
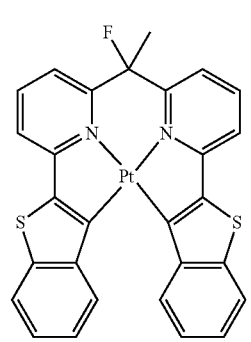
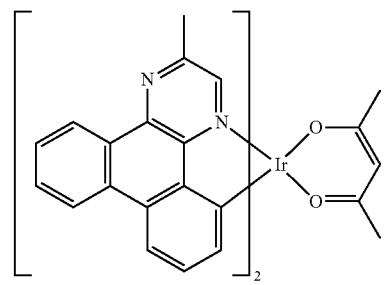
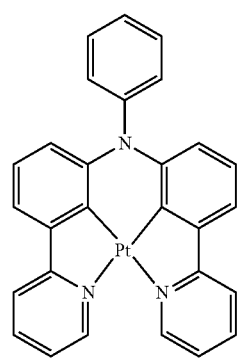
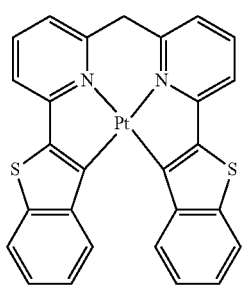
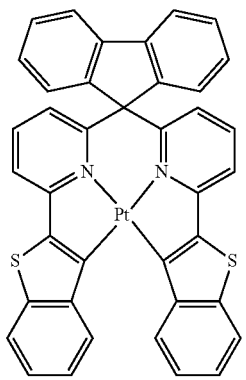
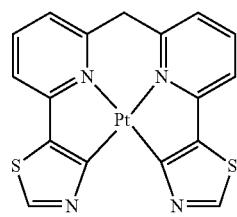

| 57 -continued | 58 -continued |
|---|---|
| 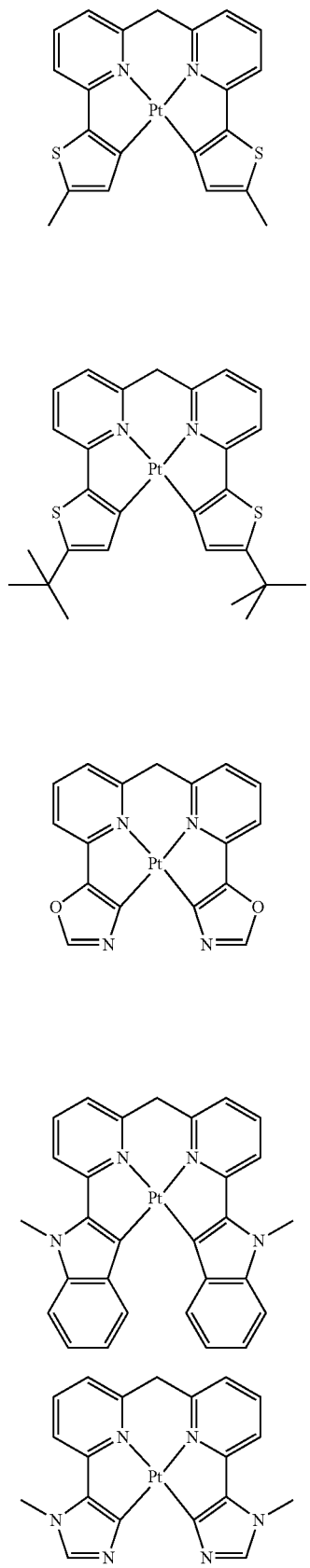 | 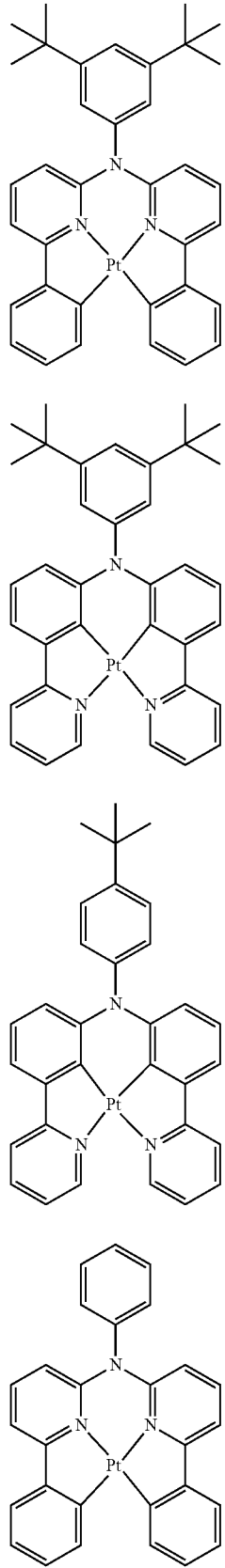 |

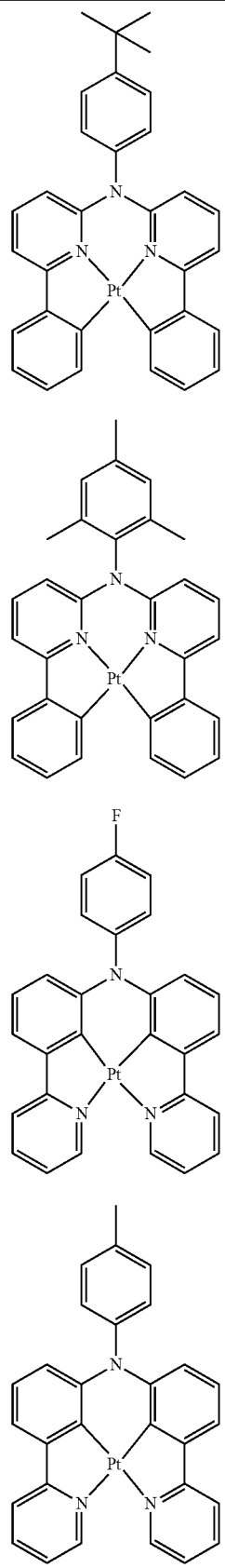
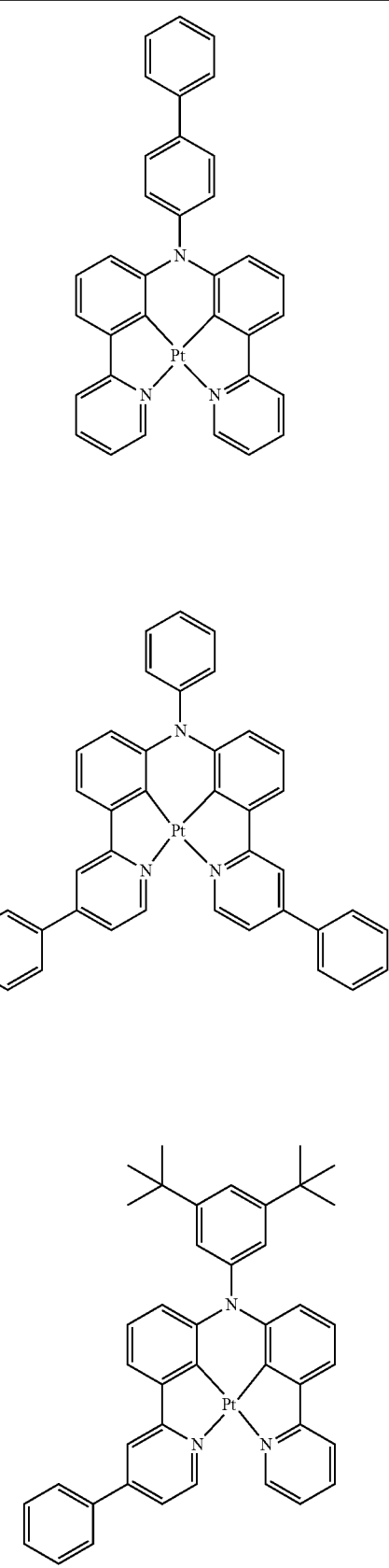

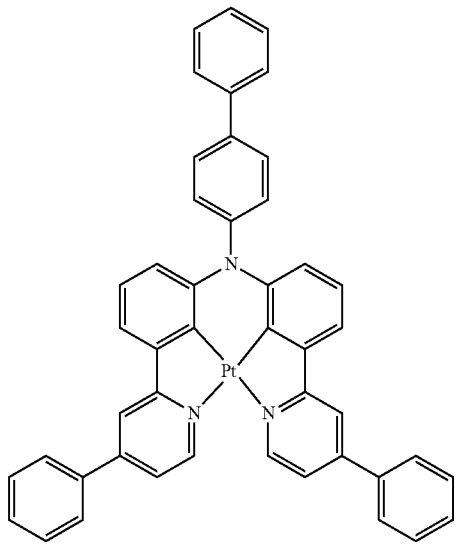
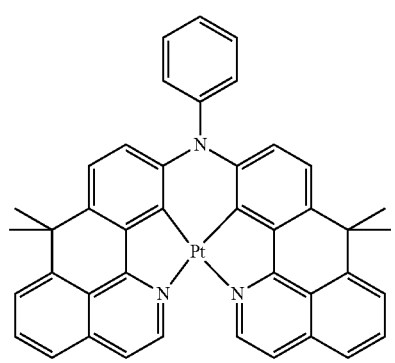
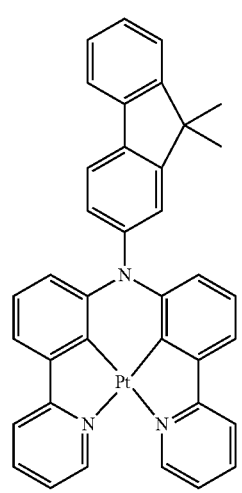
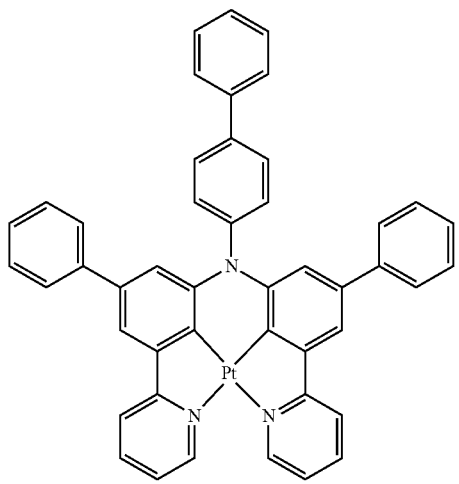
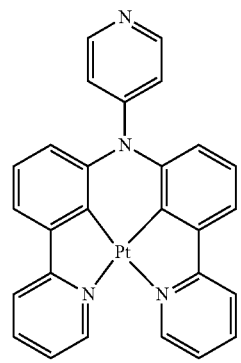
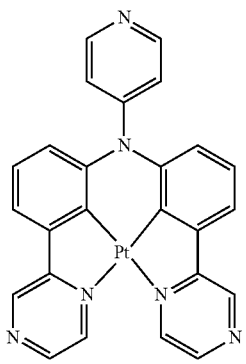
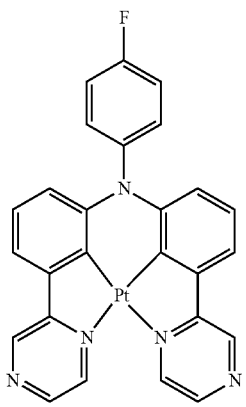

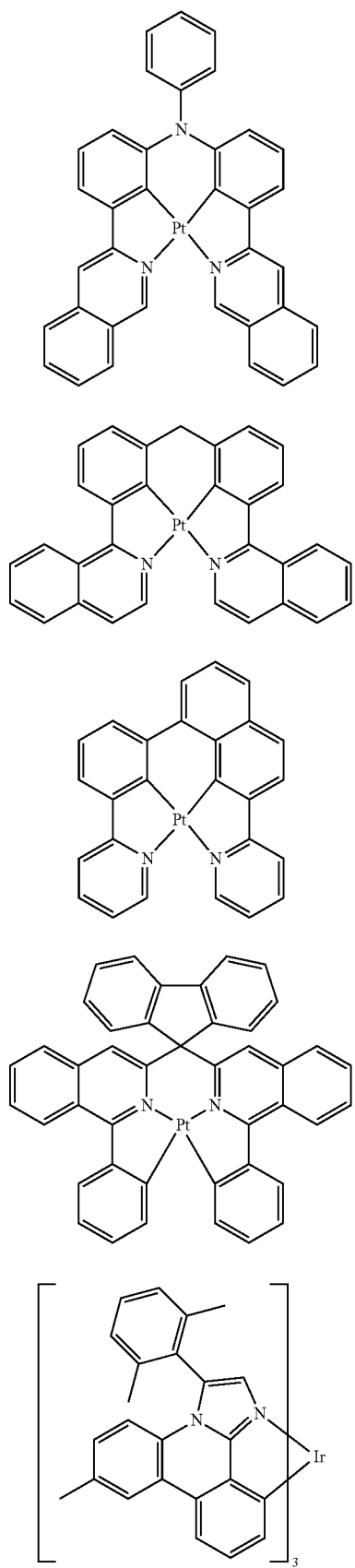

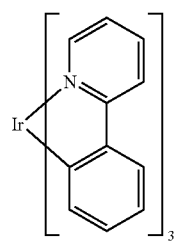
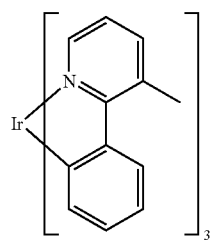
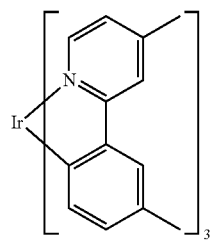
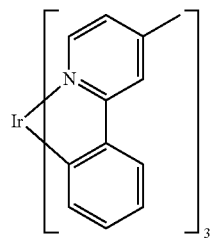
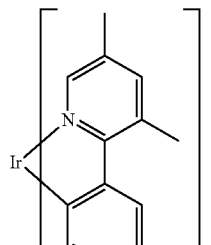
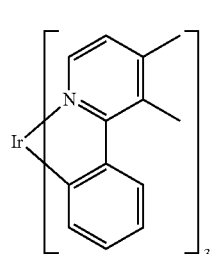
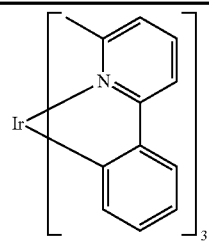
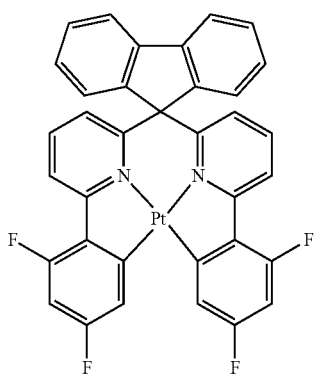
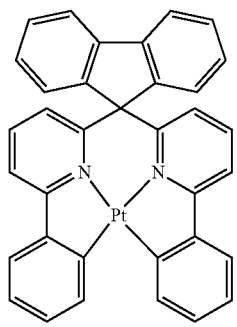
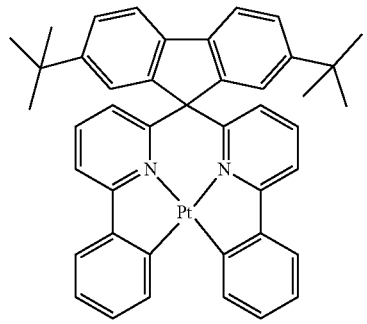
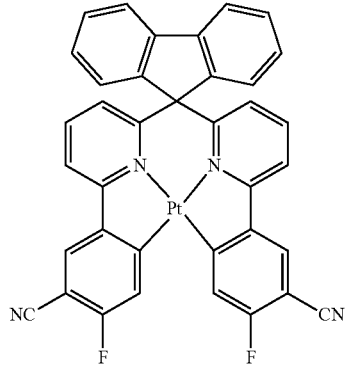

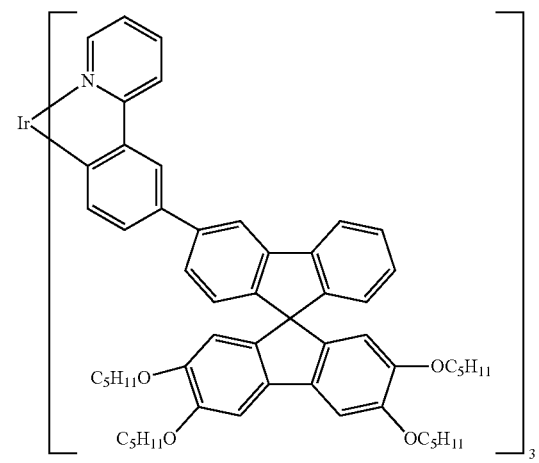
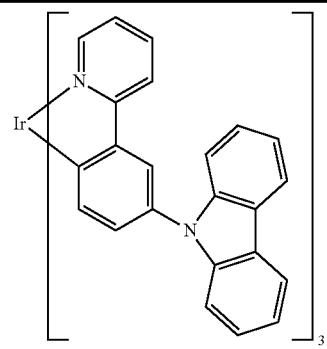
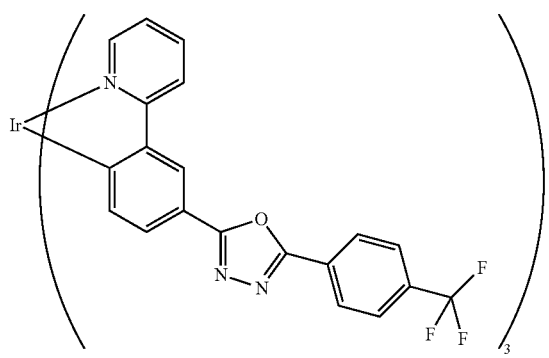
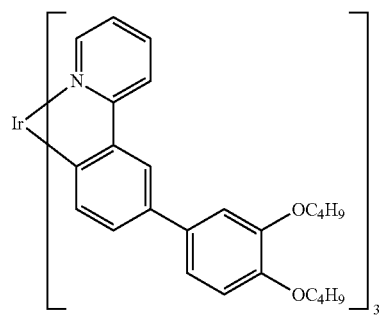
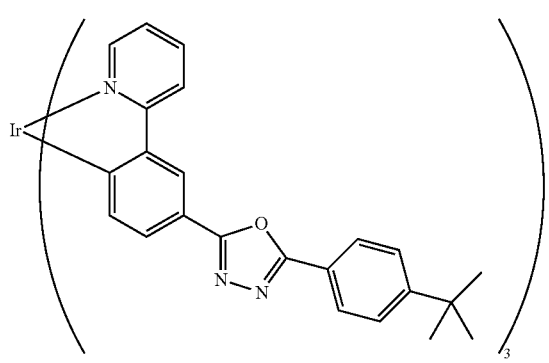
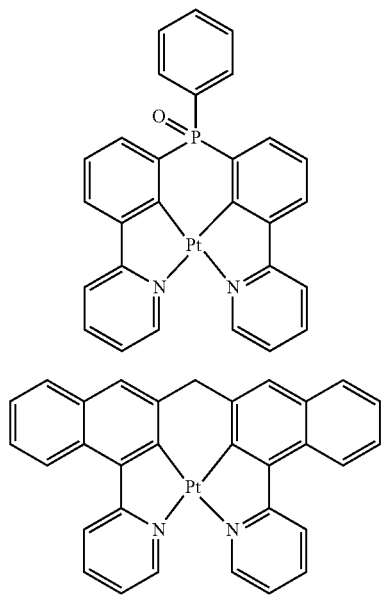
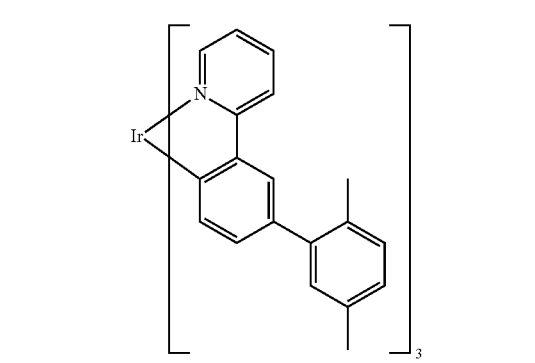
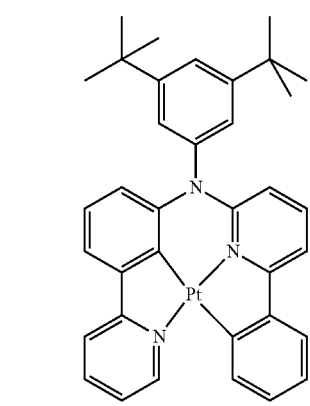

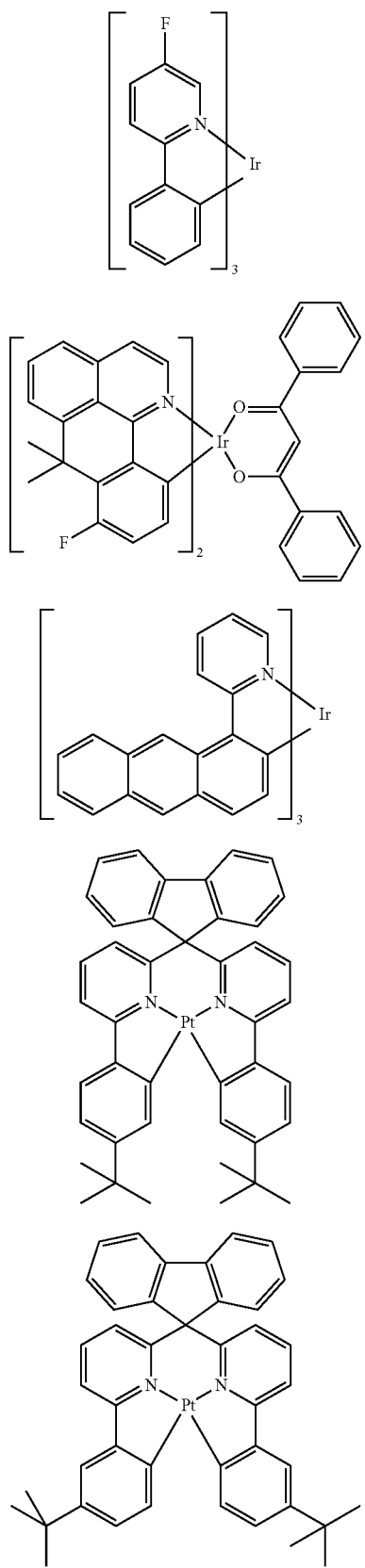
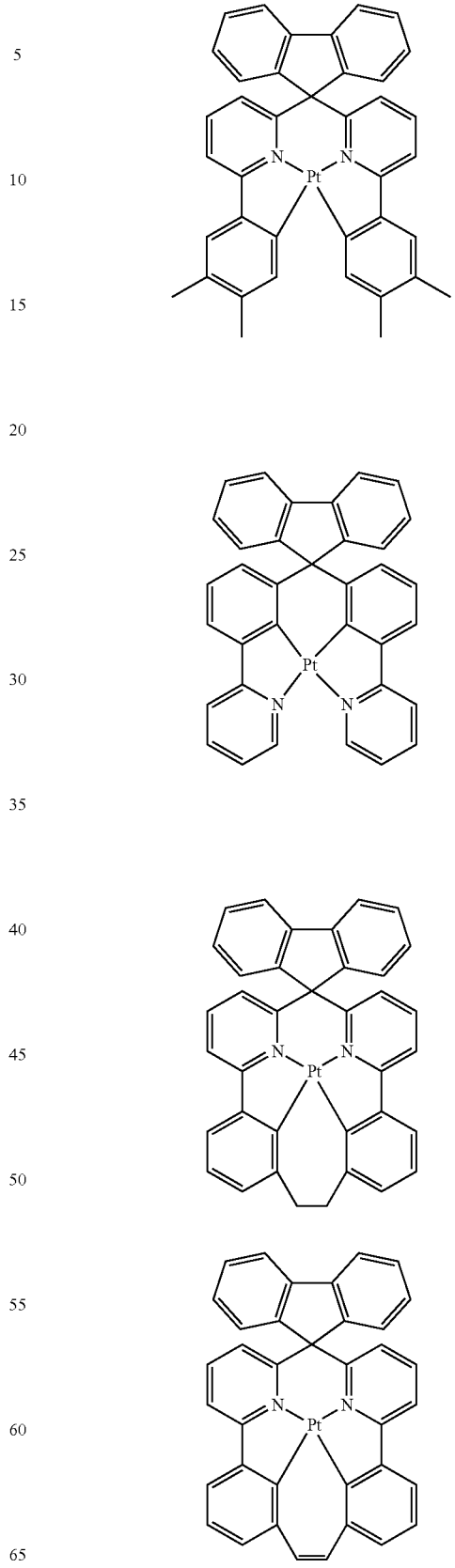

71
-continued
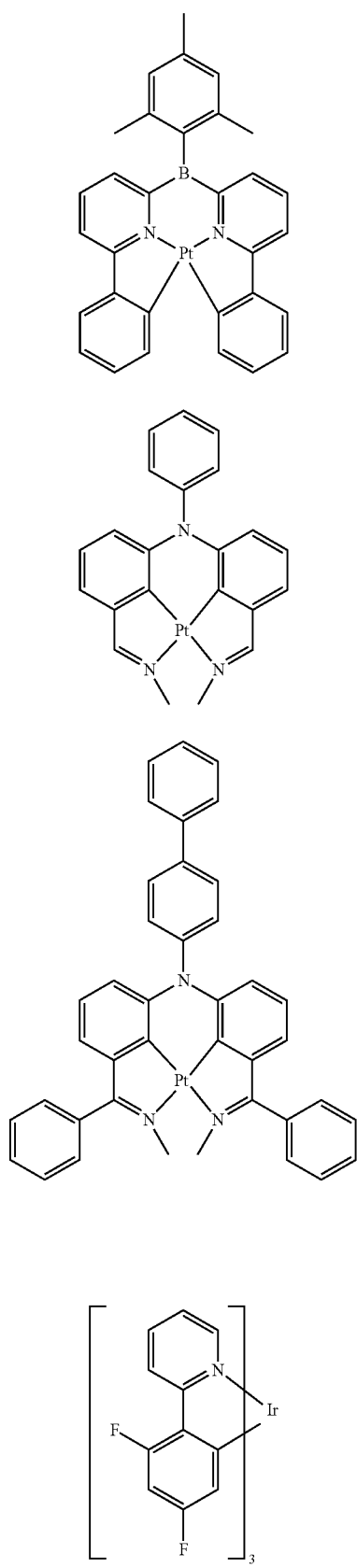
72
-continued
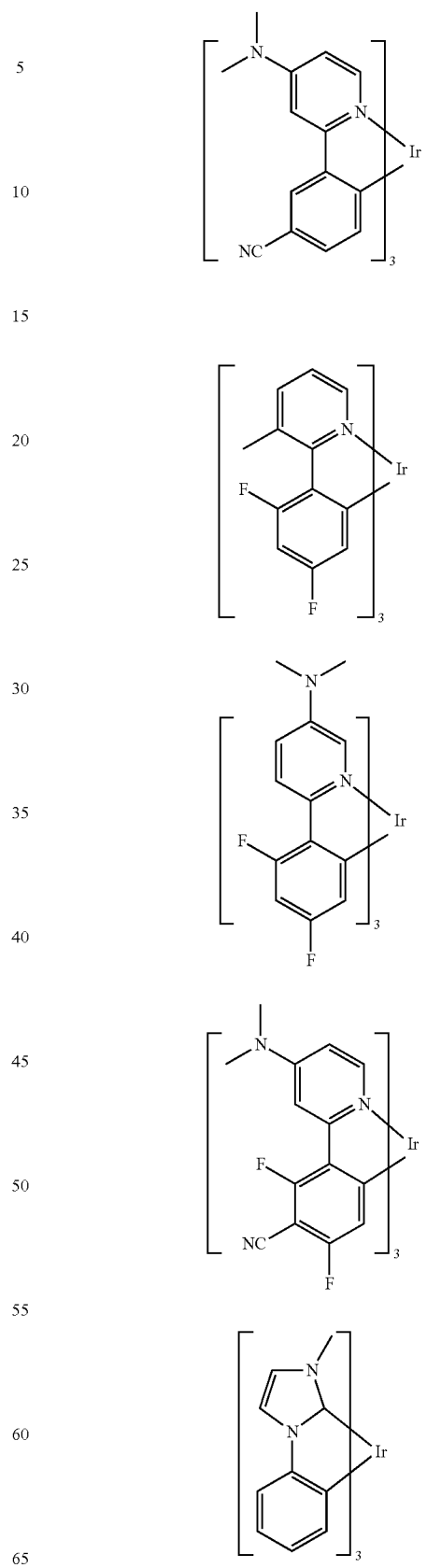

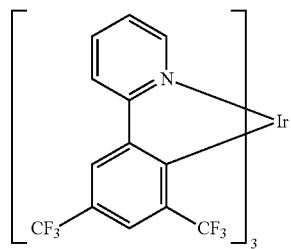
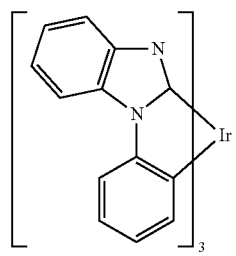
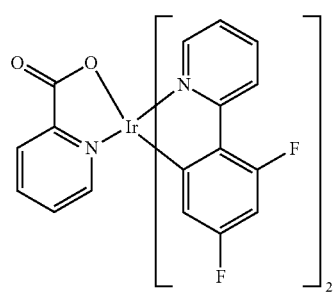
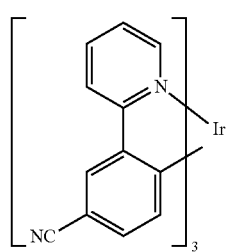
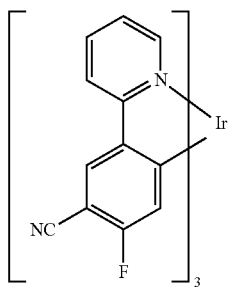
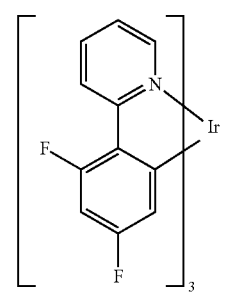
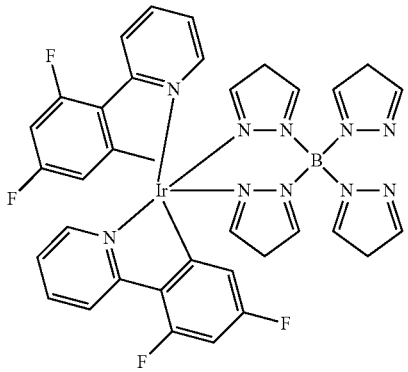
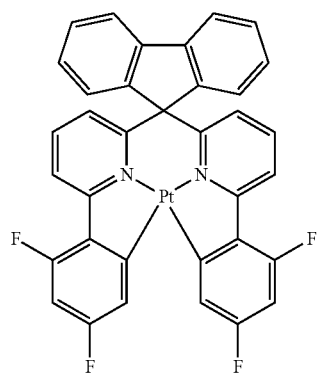
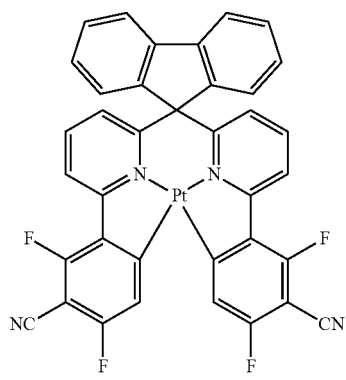
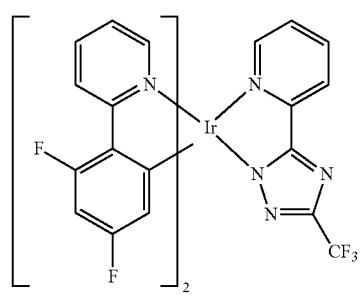

-continued

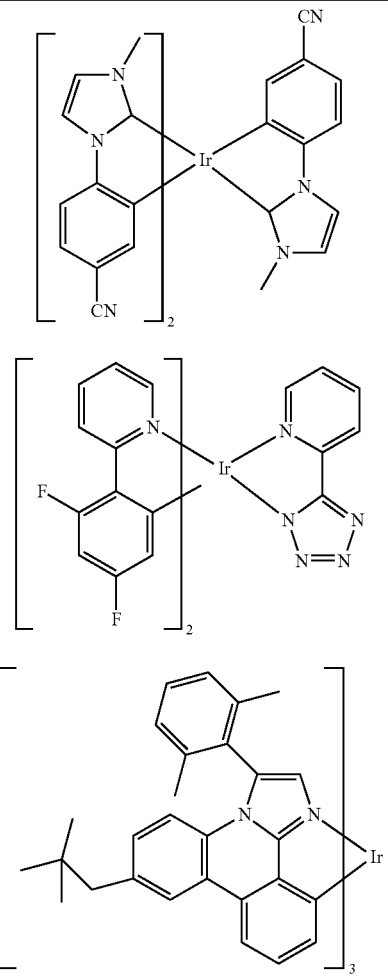

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred fluorescent dopants are selected from indenofluorenamines or indenofluorenediamines, for example in accordance with WO 06/122630, benzoindenofluorenamines or benzoindenofluorenediamines, for example in accordance with WO 08/006,449, and dibenzoindenofluorenamines or dibenzoindenofluorenediamines, for example in accordance with WO 07/140,847. Examples of fluorescent dopants from the class of the styrylamines are substituted or unsubstituted tristilbenamines or the fluorescent dopants described in WO 06/000388, WO 06/058737, WO 06/000389, WO 07/065, 549 and WO 07/115,610. Preference is furthermore given to the condensed hydrocarbons disclosed in DE 102008035413.

Furthermore, the compounds of the formula (I) are preferably used as fluorescent dopants.

Suitable fluorescent dopants are furthermore the structures depicted in the following table, and the derivatives of these structures disclosed in JP 06/001973, WO 04/047499, WO 06/098080, WO 07/065678, US 2005/0260442 and WO 04/092111.

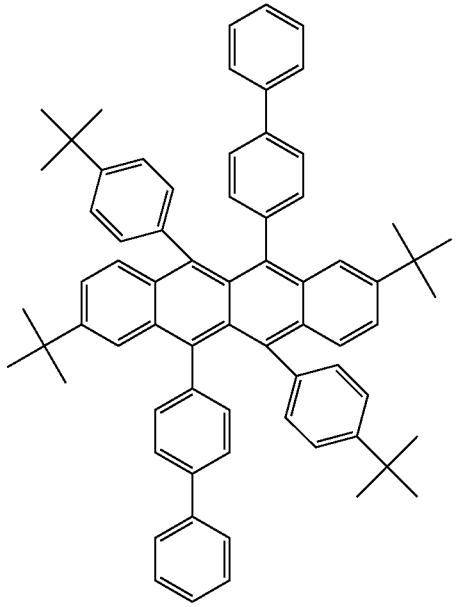 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]

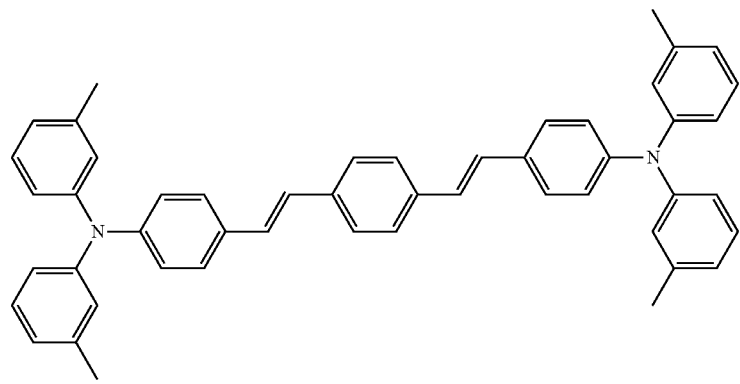 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]
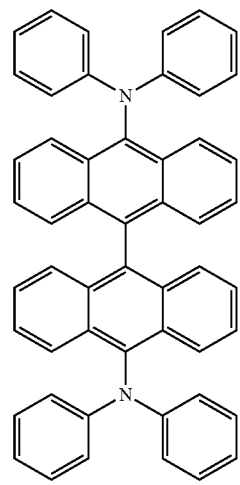 [SMILES: c1ccc(N(c2ccccc2)c2c3ccccc3c(-c3c4ccccc4c(N(c4ccccc4)c4ccccc4)c4ccccc34)c3ccccc23)cc1]
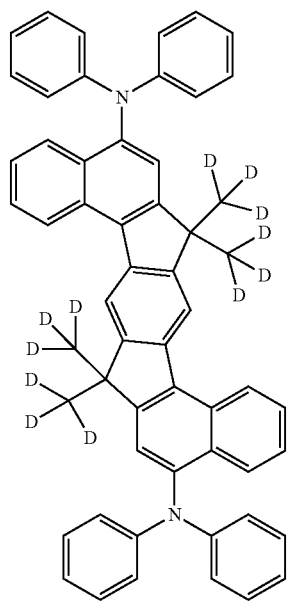 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]

-continued
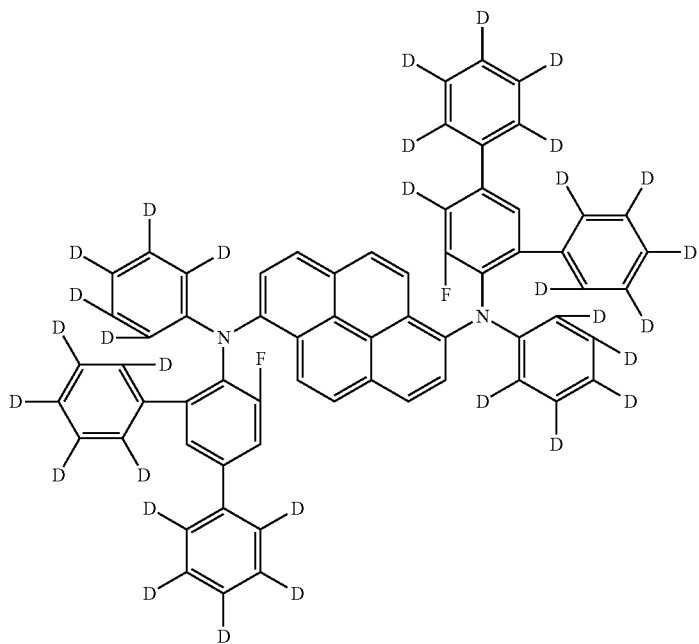 [SMILES: [2H]c1c([2H])c([2H])c(-c2cc(F)c(N(c3c([2H])c([2H])c([2H])c([2H])c3[2H])c3ccc4ccc5c(N(c6c([2H])c([2H])c([2H])c([2H])c6[2H])c6c(-c7c([2H])c([2H])c([2H])c([2H])c7[2H])cc(-c7c([2H])c([2H])c([2H])c([2H])c7[2H])c([2H])c6F)ccc6ccc3c4c65)c(-c3c([2H])c([2H])c([2H])c([2H])c3[2H])c2)c([2H])c1[2H]]
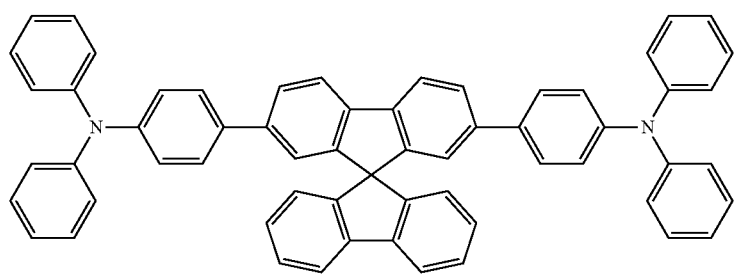 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]
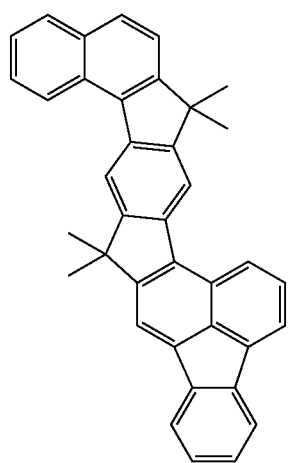 [SMILES: CC1(C)c2cc3c(cc2-c2c1ccc1ccccc21)C(C)(C)c1cc2c4c(cccc4c1-3)-c1ccccc1-2]

-continued
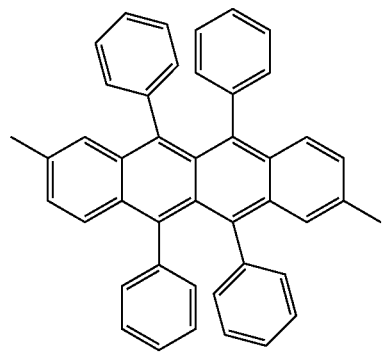

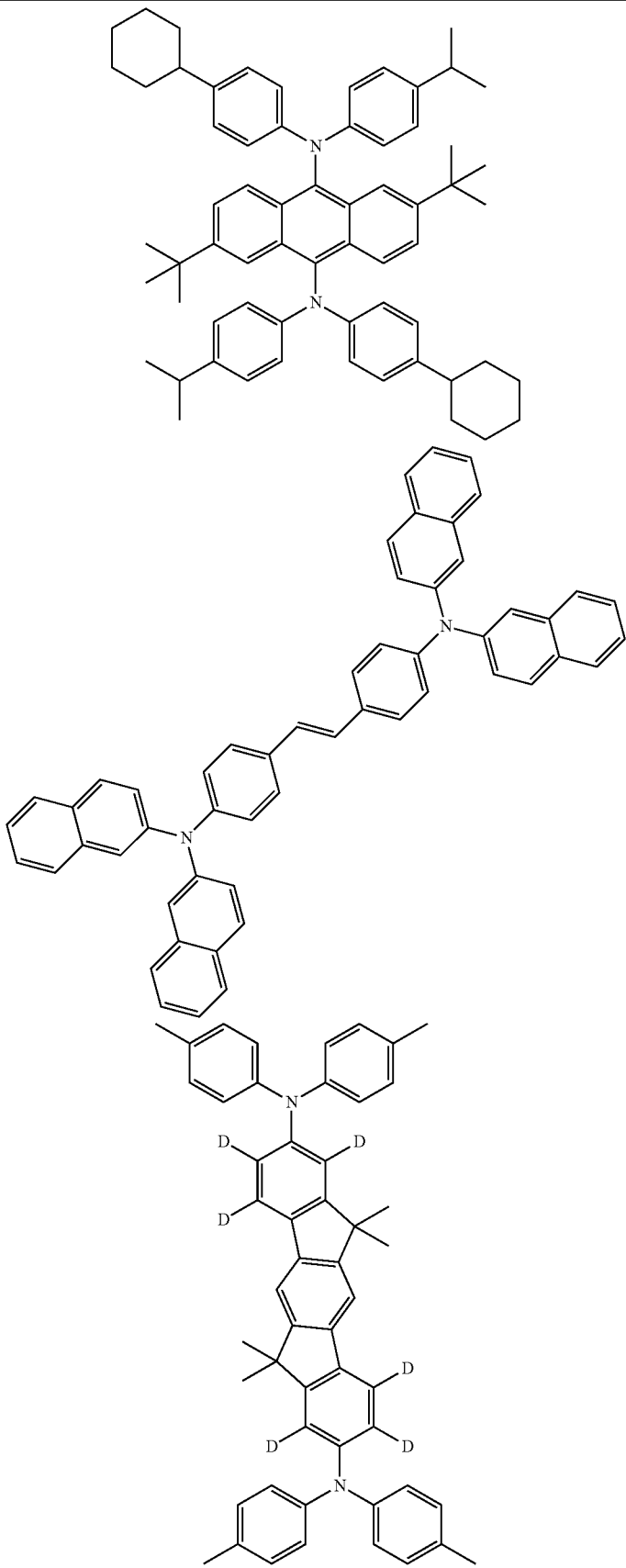

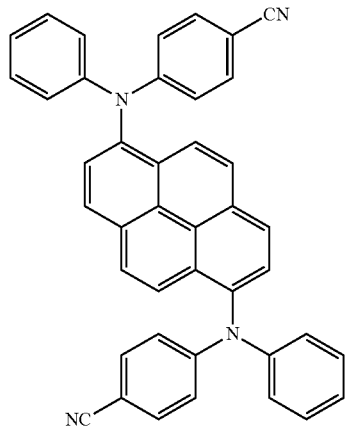 [SMILES: N#Cc1ccc(N(c2ccccc2)c2ccc3ccc4c(N(c5ccccc5)c5ccc(C#N)cc5)ccc5ccc2c3c54)cc1]
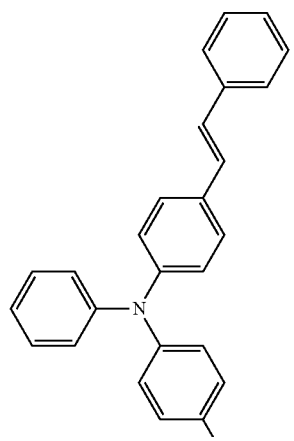
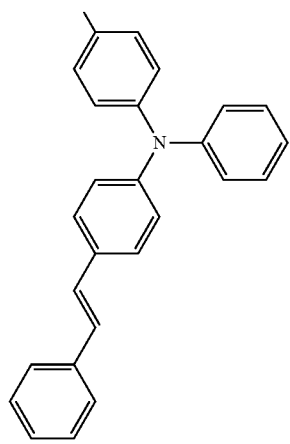

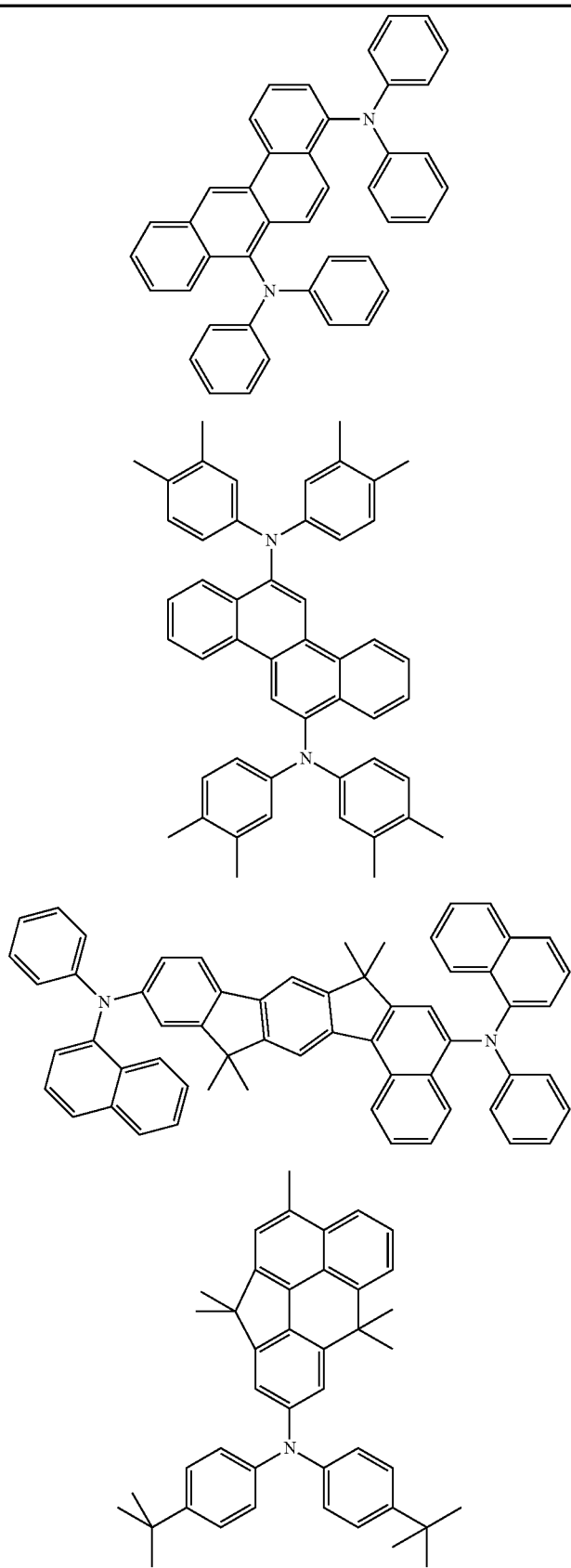

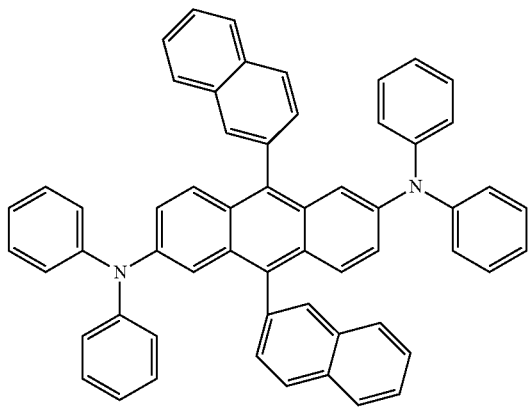 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
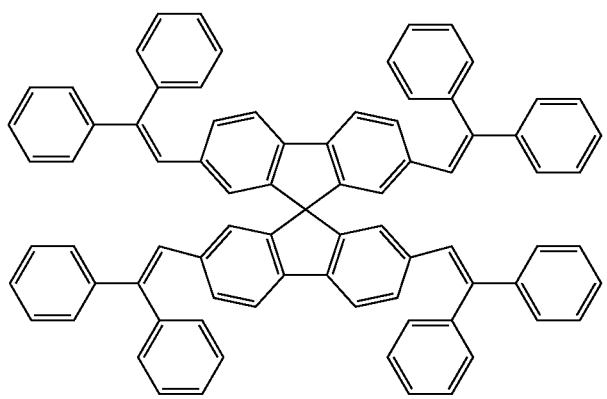 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]
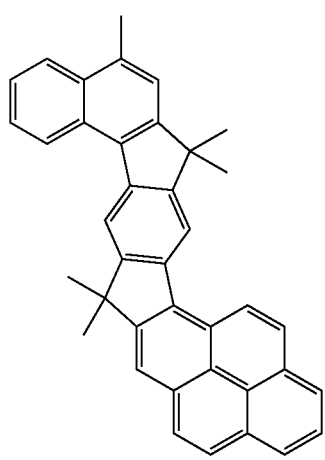 [SMILES: Cc1cc2c(c3ccccc13)-c1cc3c(cc1C2(C)C)-c1c(cc2ccc4cccc5ccc1c2c45)C3(C)C]

-continued
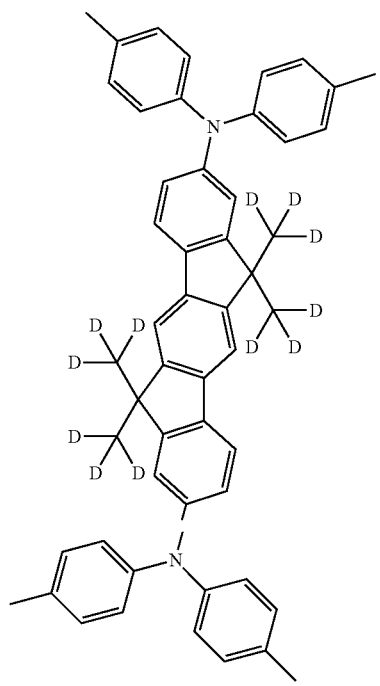
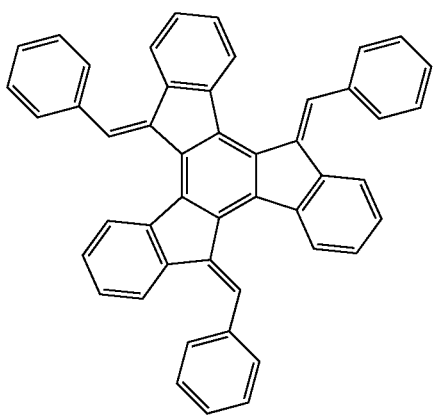 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]
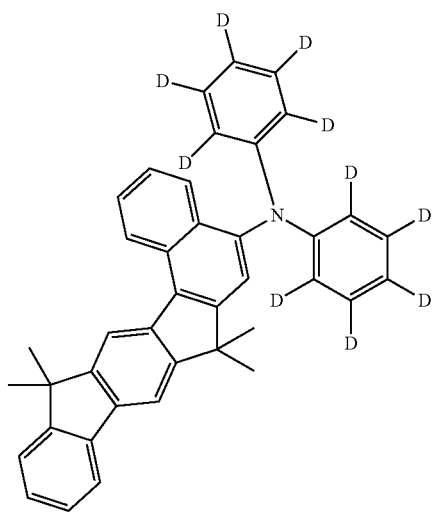 [SMILES: [2H]c1c([2H])c([2H])c(N(c2c([2H])c([2H])c([2H])c([2H])c2[2H])c2cc3c(c4ccccc24)-c2cc4c(cc2C3(C)C)-c2ccccc2C4(C)C)c([2H])c1[2H]]

-continued
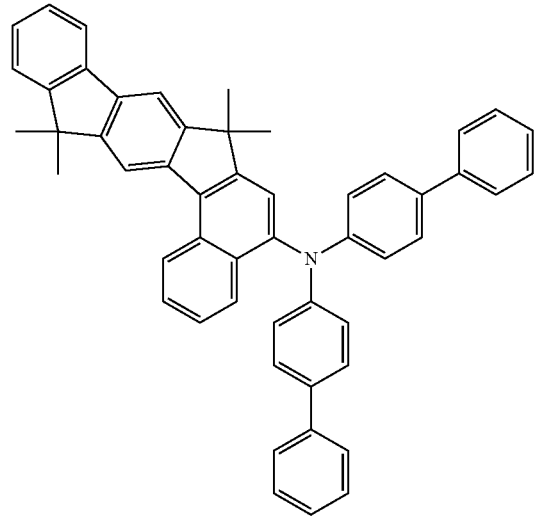 [SMILES: CC1(C)c2ccccc2-c2cc3c(cc21)-c1c(cc(N(c2ccc(-c4ccccc4)cc2)c2ccc(-c4ccccc4)cc2)c2ccccc12)C3(C)C]
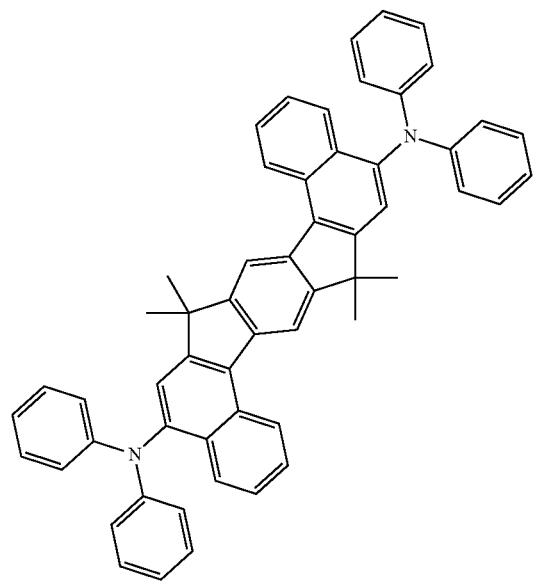 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]
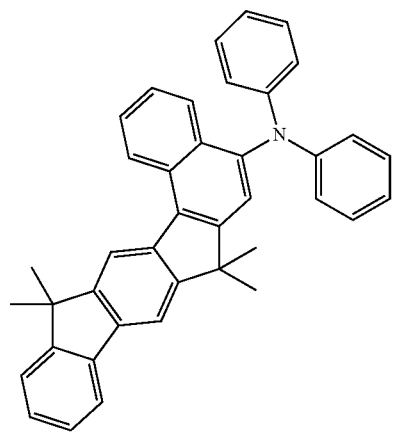 [SMILES: CC1(C)c2ccccc2-c2cc3c(cc21)-c1c(cc(N(c2ccccc2)c2ccccc2)c2ccccc12)C3(C)C]

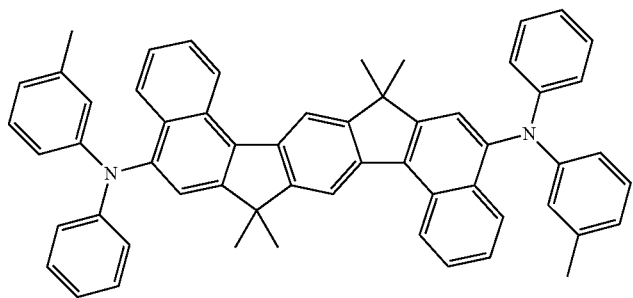 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]
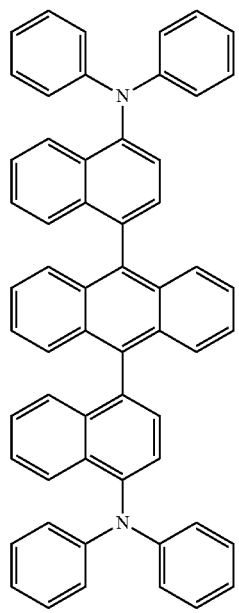 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]
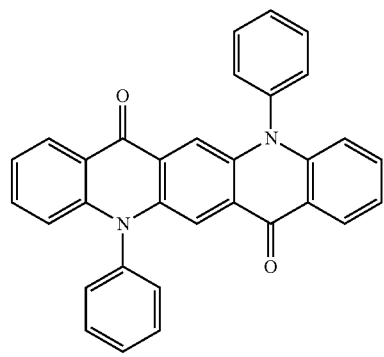 [SMILES: O=c1c2ccccc2n(-c2ccccc2)c2cc3c(=O)c4ccccc4n(-c4ccccc4)c3cc12]

-continued
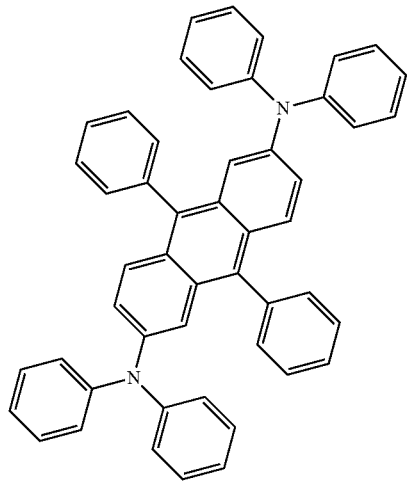 [SMILES: c1ccc(-c2c3ccc(N(c4ccccc4)c4ccccc4)cc3c(-c3ccccc3)c3ccc(N(c4ccccc4)c4ccccc4)cc23)cc1]
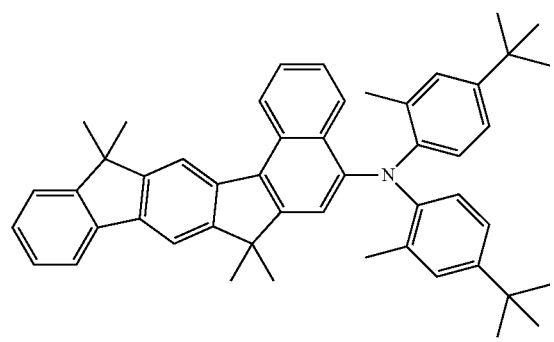 [SMILES: Cc1cc(C(C)(C)C)ccc1N(c1ccc(C(C)(C)C)cc1C)c1cc2c(c3ccccc13)-c1cc3c(cc1C2(C)C)-c1ccccc1C3(C)C]
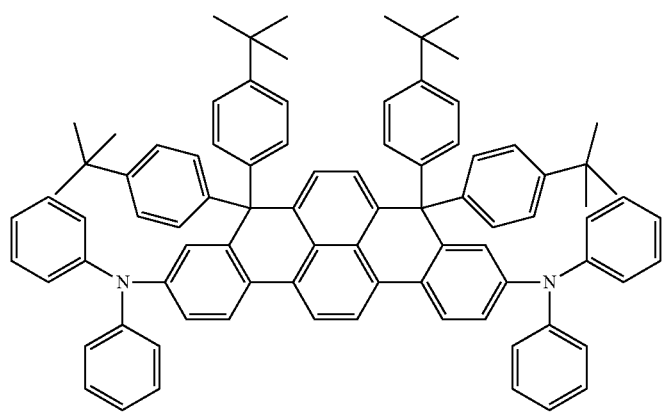 [SMILES: CC(C)(C)c1ccc(C2(c3ccc(C(C)(C)C)cc3)c3cc(N(c4ccccc4)c4ccccc4)ccc3-c3ccc4c5c(ccc2c35)C(c2ccc(C(C)(C)C)cc2)(c2ccc(C(C)(C)C)cc2)c2cc(N(c3ccccc3)c3ccccc3)ccc2-4)cc1]

-continued
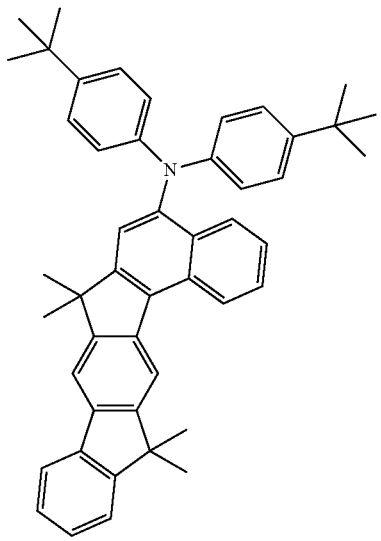 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
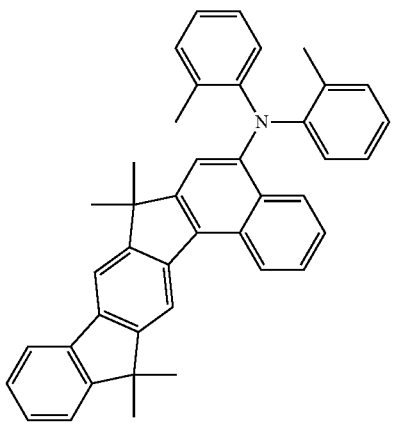 [SMILES: Cc1ccccc1N(c1ccccc1C)c1cc2c(c3ccccc13)-c1cc3c(cc1C2(C)C)-c1ccccc1C3(C)C]
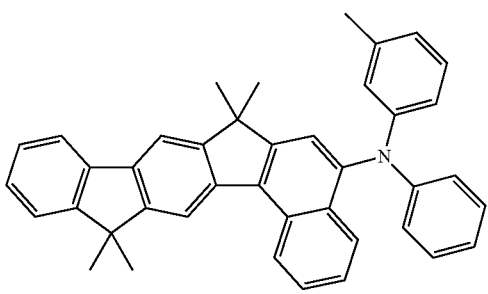 [SMILES: Cc1cccc(N(c2ccccc2)c2cc3c(c4ccccc24)-c2cc4c(cc2C3(C)C)-c2ccccc2C4(C)C)c1]
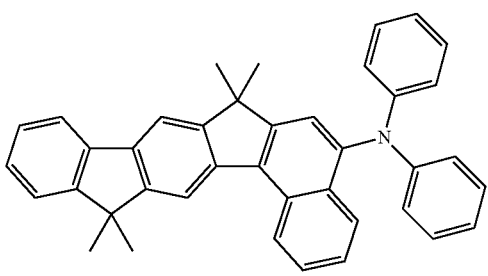 [SMILES: CC1(C)c2ccccc2-c2cc3c(cc21)-c1c(cc(N(c2ccccc2)c2ccccc2)c2ccccc12)C3(C)C]

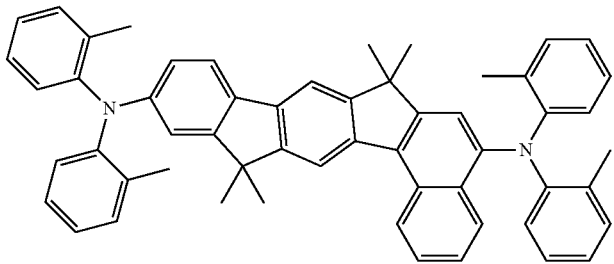 [SMILES: Cc1ccccc1N(c1ccc2c(c1)C(C)(C)c1cc3c(cc1-2)C(C)(C)c1cc(N(c2ccccc2C)c2ccccc2C)c2ccccc2c1-3)c1ccccc1C]
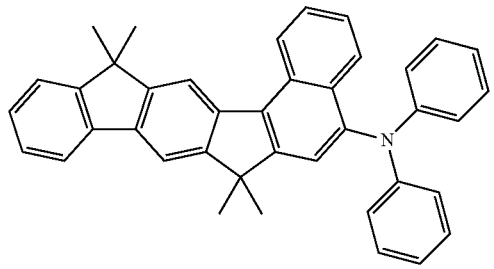 [SMILES: CC1(C)c2ccccc2-c2cc3c(cc21)-c1c(cc(N(c2ccccc2)c2ccccc2)c2ccccc12)C3(C)C]
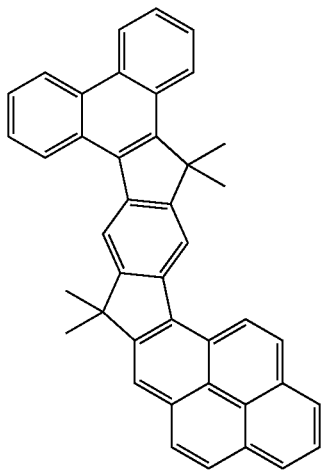 [SMILES: CC1(C)c2cc3c(cc2-c2c1cc1ccc4cccc5ccc2c1c45)C(C)(C)c1c-3c2ccccc2c2ccccc12]
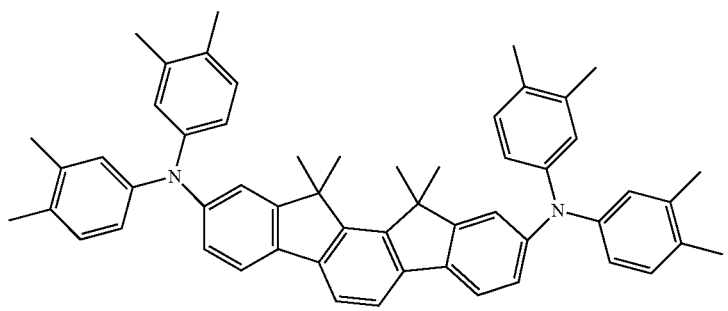
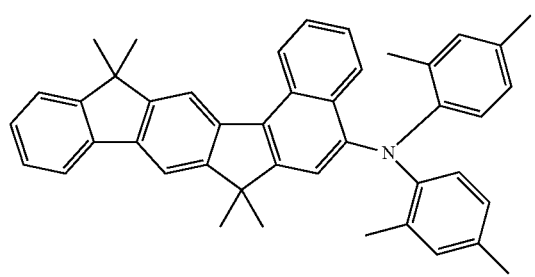 [SMILES: Cc1ccc(N(c2ccc(C)cc2C)c2cc3c(c4ccccc24)-c2cc4c(cc2C3(C)C)-c2ccccc2C4(C)C)c(C)c1]

-continued
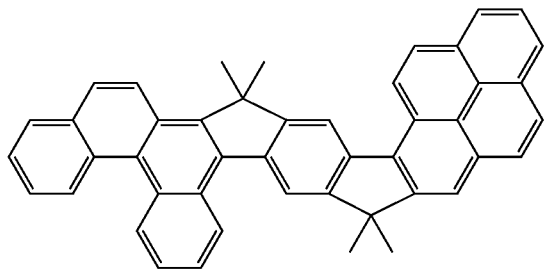 [SMILES: CC1(C)c2cc3c(cc2-c2c1cc1ccc4cccc5ccc2c1c45)C(C)(C)c1c-3c2ccccc2c2c1ccc1ccccc12]
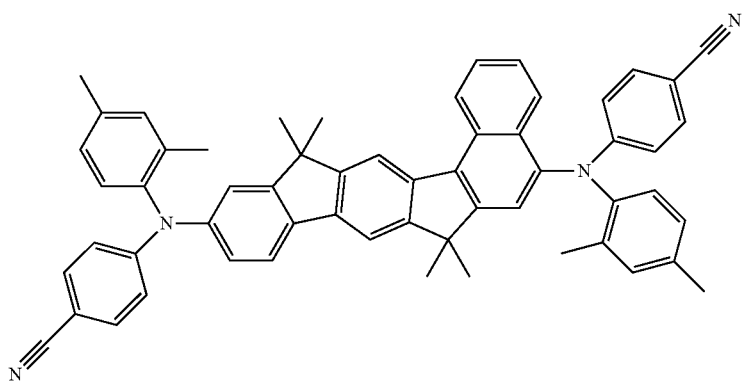 [SMILES: Cc1ccc(N(c2ccc(C#N)cc2)c2ccc3c(c2)C(C)(C)c2cc4c(cc2-3)C(C)(C)c2cc(N(c3ccc(C#N)cc3)c3ccc(C)cc3C)c3ccccc3c2-4)c(C)c1]
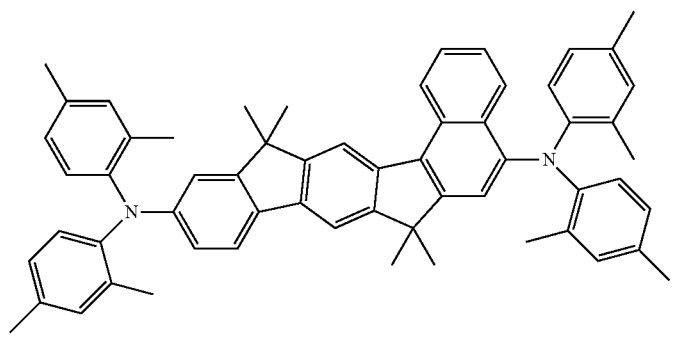
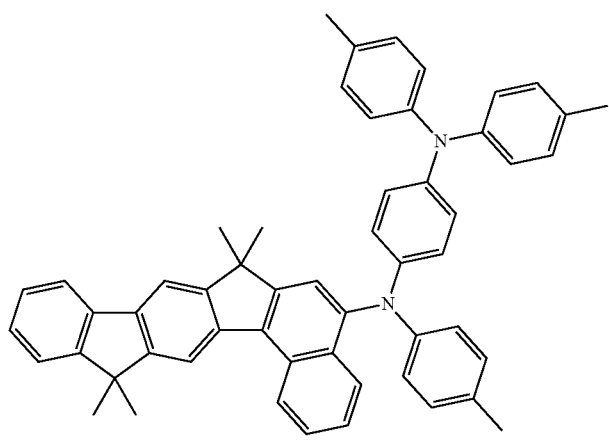 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]

-continued

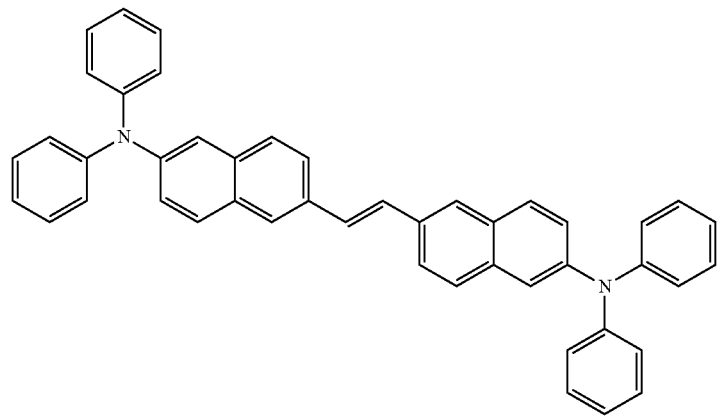 [SMILES: C(=C\c1ccc2cc(N(c3ccccc3)c3ccccc3)ccc2c1)/c1ccc2cc(N(c3ccccc3)c3ccccc3)ccc2c1]

Suitable matrix materials, preferably for fluorescent dopants, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145,239). Suitable matrix materials are furthermore preferably the compounds according to the invention. Particularly preferred matrix materials are selected from the classes of the oligoarylenes; comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials, preferably for fluorescent dopants, are, for example, the materials depicted in the following table, and derivatives of these materials, as disclosed in WO 04/018587, WO 08/006,449, U.S. Pat. No. 5,935,721, US 2005/0181232, JP 2000/273056, EP 681019, US 2004/0247937 and US 2005/0211958.

-continued

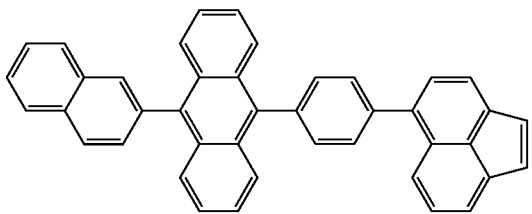 [SMILES: C1=Cc2ccc(-c3ccc(-c4c5ccccc5c(-c5ccc6ccccc6c5)c5ccccc45)cc3)c3cccc1c23]

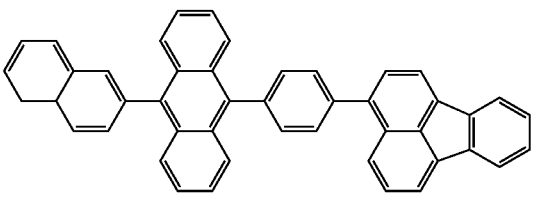 [SMILES: C1=CCC2C=CC(c3c4ccccc4c(-c4ccc(-c5ccc6c7c(cccc57)-c5ccccc5-6)cc4)c4ccccc34)=CC2=C1]

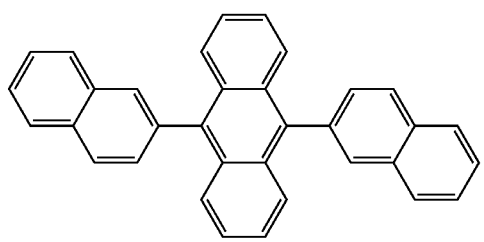 [SMILES: c1ccc2cc(-c3c4ccccc4c(-c4ccc5ccccc5c4)c4ccccc34)ccc2c1]

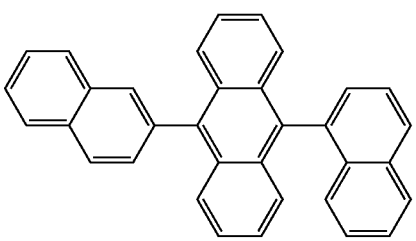 [SMILES: c1ccc2cc(-c3c4ccccc4c(-c4cccc5ccccc45)c4ccccc34)ccc2c1]

| 107 -continued | 108 -continued |
|---|---|
| 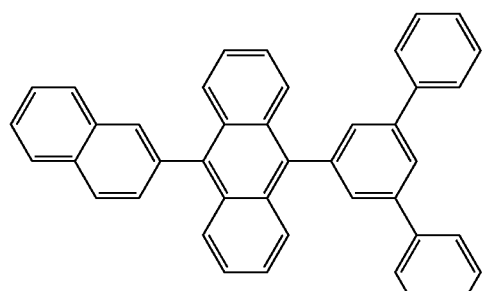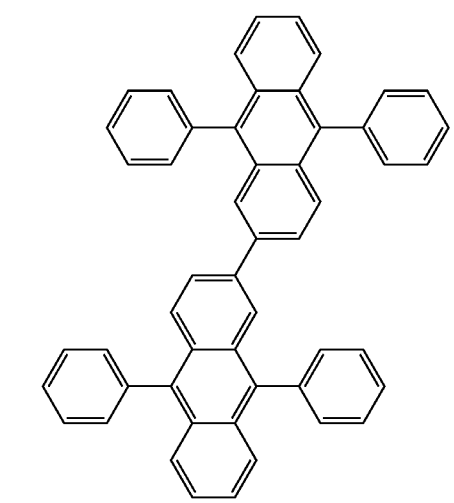 [SMILES: c1ccc(-c2c3ccccc3c(-c3ccccc3)c3cc(-c4ccc5c(-c6ccccc6)c6ccccc6c(-c6ccccc6)c5c4)ccc23)cc1]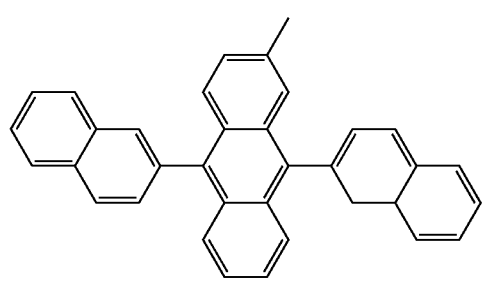 [SMILES: Cc1ccc2c(-c3ccc4ccccc4c3)c3ccccc3c(C3=CC=C4C=CC=CC4C3)c2c1]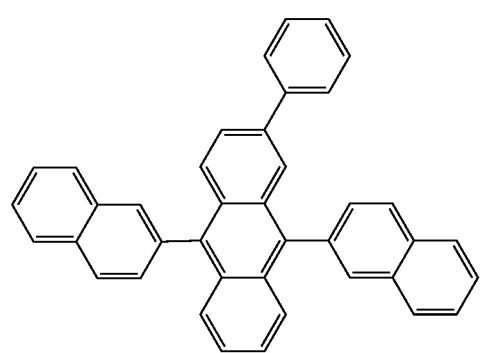 [SMILES: c1ccc(-c2ccc3c(-c4ccc5ccccc5c4)c4ccccc4c(-c4ccc5ccccc5c4)c3c2)cc1] | 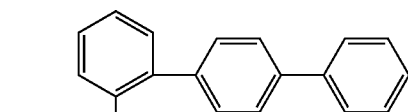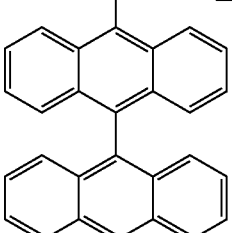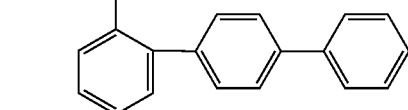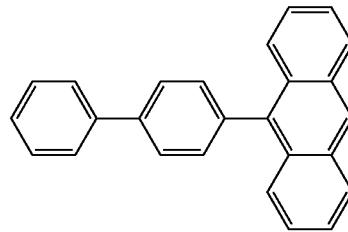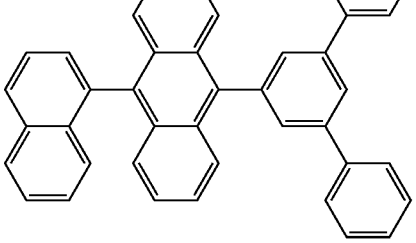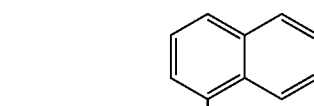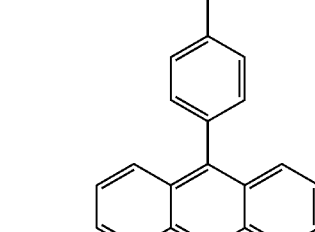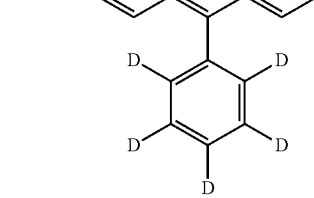 |

| 109 -continued | 110 -continued |
|---|---|
| 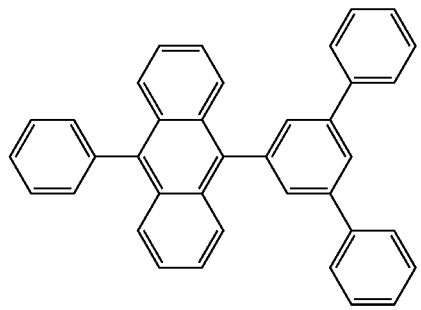 [SMILES: c1ccc(-c2cc(-c3ccccc3)cc(-c3c4ccccc4c(-c4ccccc4)c4ccccc34)c2)cc1]<br>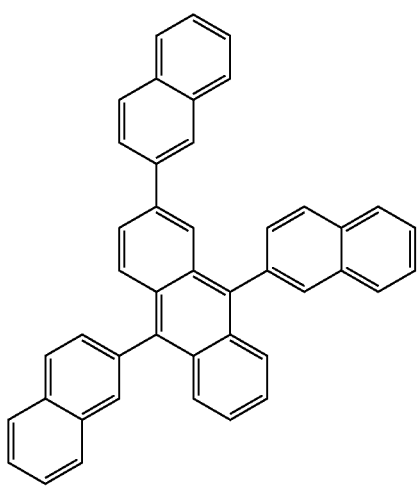 [SMILES: c1ccc2cc(-c3ccc4c(-c5ccc6ccccc6c5)c5ccccc5c(-c5ccc6ccccc6c5)c4c3)ccc2c1]<br>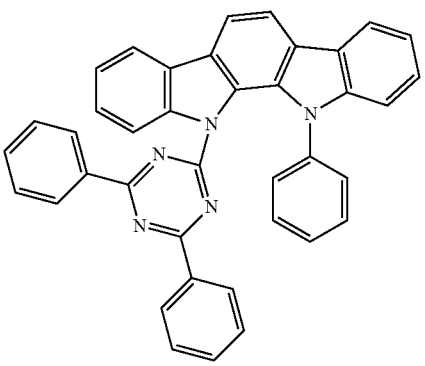 [SMILES: c1ccc(-c2nc(-c3ccccc3)nc(-n3c4ccccc4c4ccc5c6ccccc6n(-c6ccccc6)c5c43)n2)cc1]<br>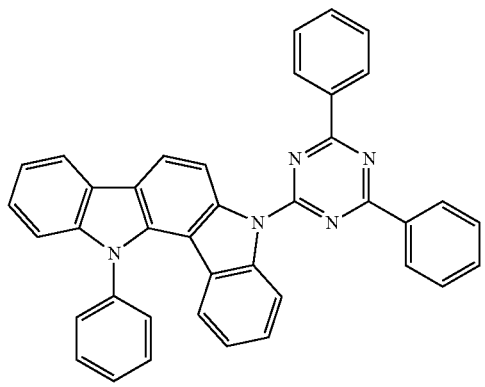 [SMILES: c1ccc(-c2nc(-c3ccccc3)nc(-n3c4ccccc4c4c3ccc3c5ccccc5n(-c5ccccc5)c34)n2)cc1] | 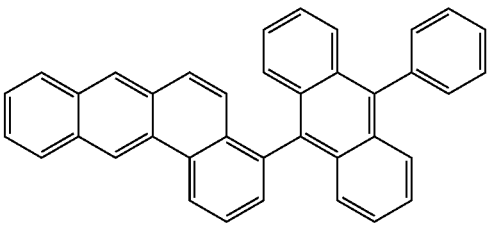 [SMILES: c1ccc(-c2c3ccccc3c(-c3cccc4c3ccc3cc5ccccc5cc34)c3ccccc23)cc1]<br>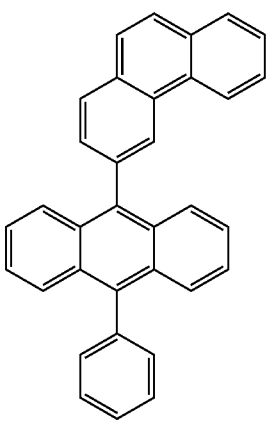 [SMILES: c1ccc(-c2c3ccccc3c(-c3ccc4ccc5ccccc5c4c3)c3ccccc23)cc1]<br>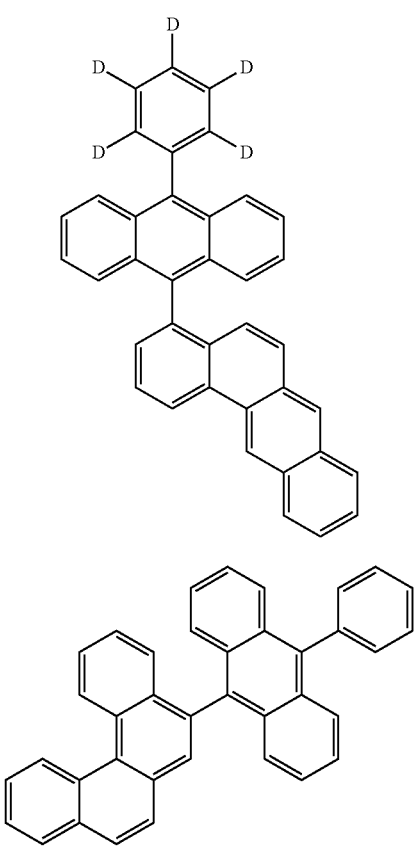<br>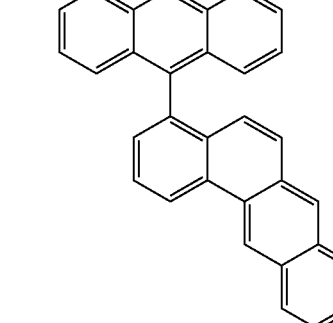 |

111
-continued
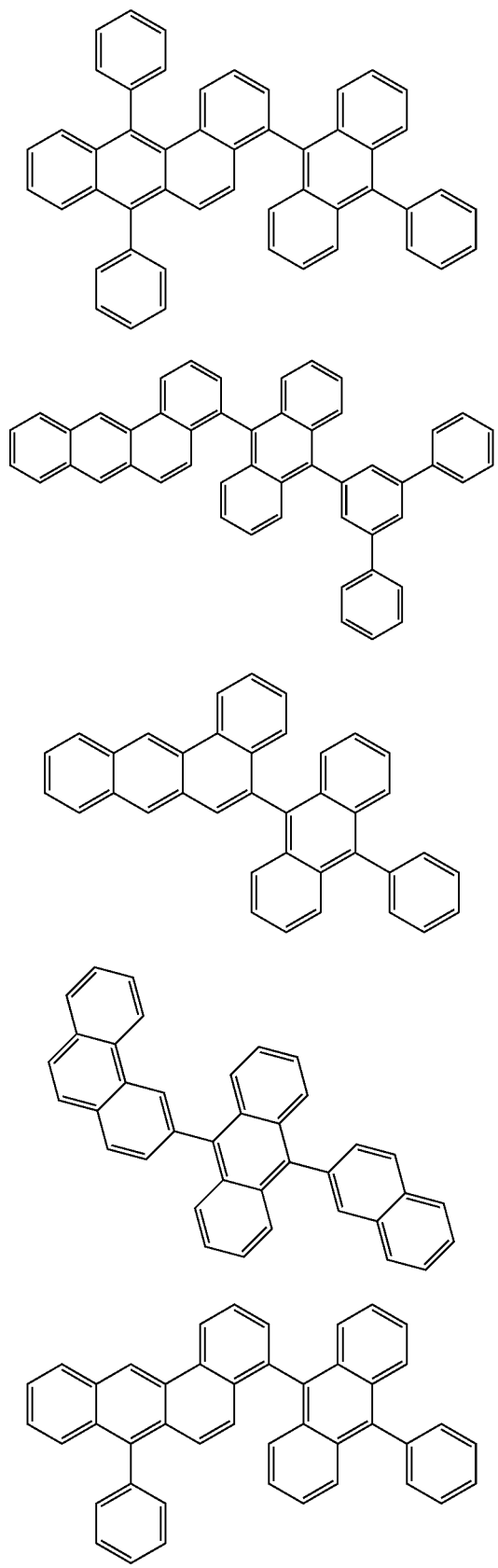
112
-continued
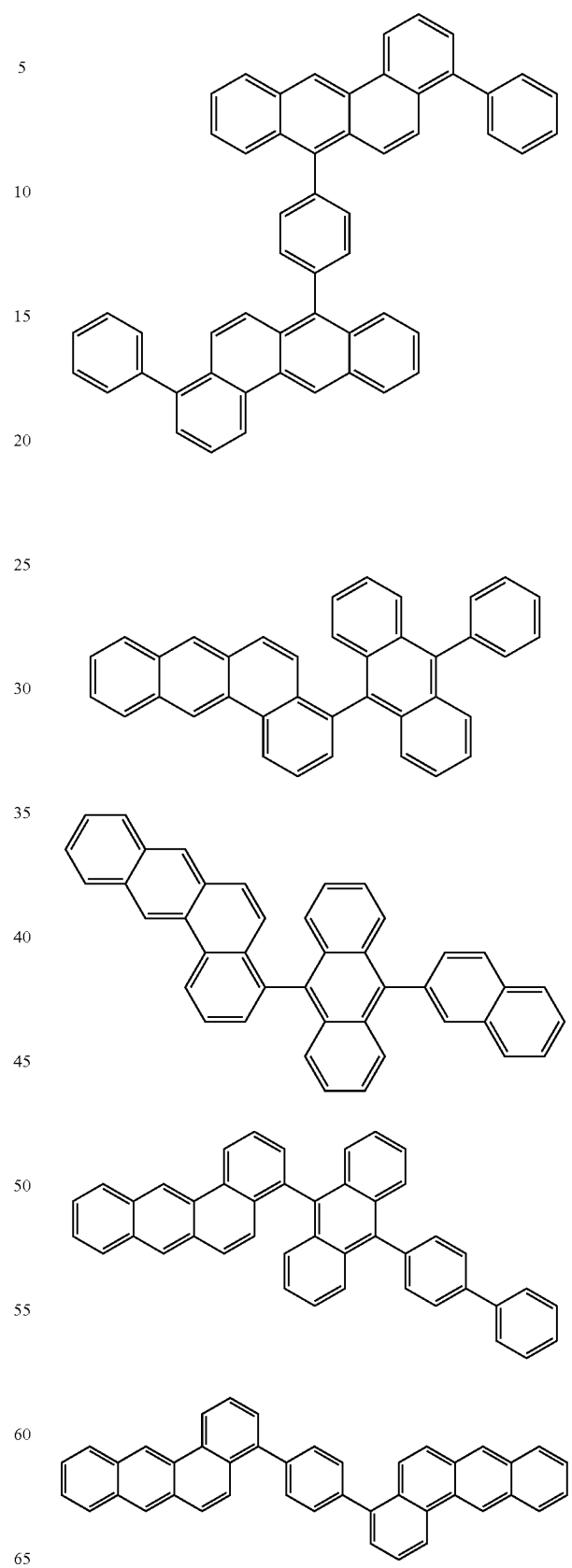

113
-continued
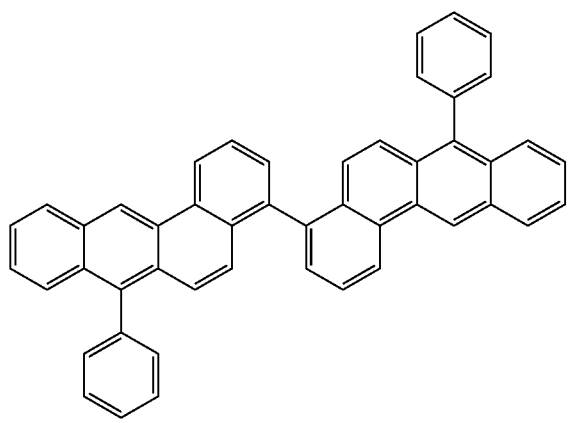 [SMILES: c1ccc(-c2c3ccccc3cc3c2ccc2c(-c4cccc5c4ccc4c(-c6ccccc6)c6ccccc6cc45)cccc23)cc1]
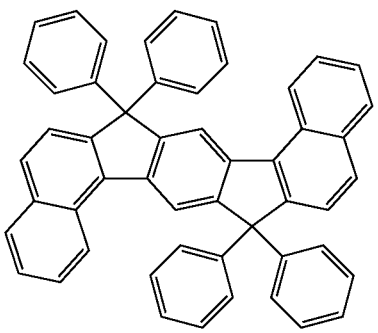 [SMILES: c1ccc(C2(c3ccccc3)c3cc4c(cc3-c3c2ccc2ccccc32)C(c2ccccc2)(c2ccccc2)c2ccc3ccccc3c2-4)cc1]
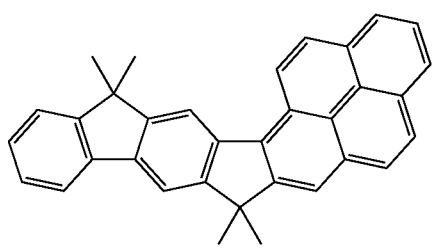 [SMILES: CC1(C)c2ccccc2-c2cc3c(cc21)-c1c(cc2ccc4cccc5ccc1c2c45)C3(C)C]
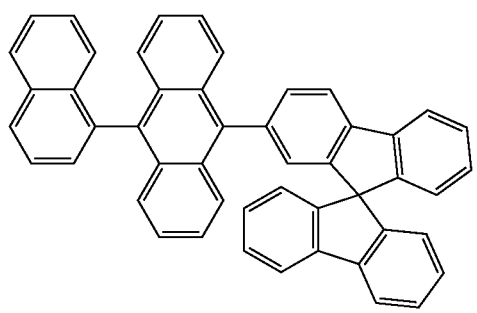 [SMILES: c1ccc2c(c1)-c1ccccc1C21c2ccccc2-c2ccc(-c3c4ccccc4c(-c4cccc5ccccc45)c4ccccc34)cc21]
114
-continued
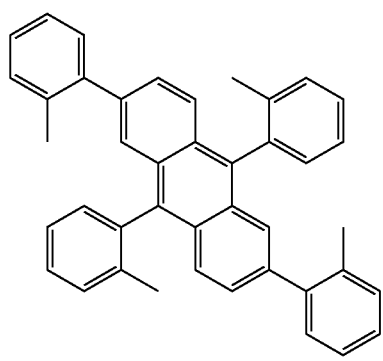 [SMILES: Cc1ccccc1-c1ccc2c(-c3ccccc3C)c3cc(-c4ccccc4C)ccc3c(-c3ccccc3C)c2c1]
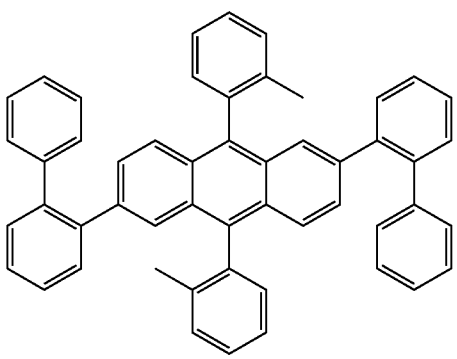 [SMILES: Cc1ccccc1-c1c2ccc(-c3ccccc3-c3ccccc3)cc2c(-c2ccccc2C)c2ccc(-c3ccccc3-c3ccccc3)cc12]
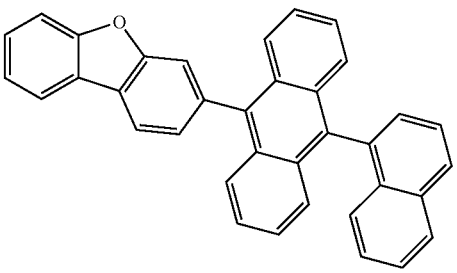 [SMILES: c1ccc2c(-c3c4ccccc4c(-c4ccc5c(c4)oc4ccccc45)c4ccccc34)cccc2c1]
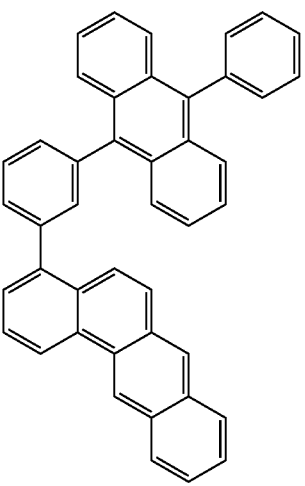 [SMILES: c1ccc(-c2c3ccccc3c(-c3cccc(-c4cccc5c4ccc4cc6ccccc6cc45)c3)c3ccccc23)cc1]

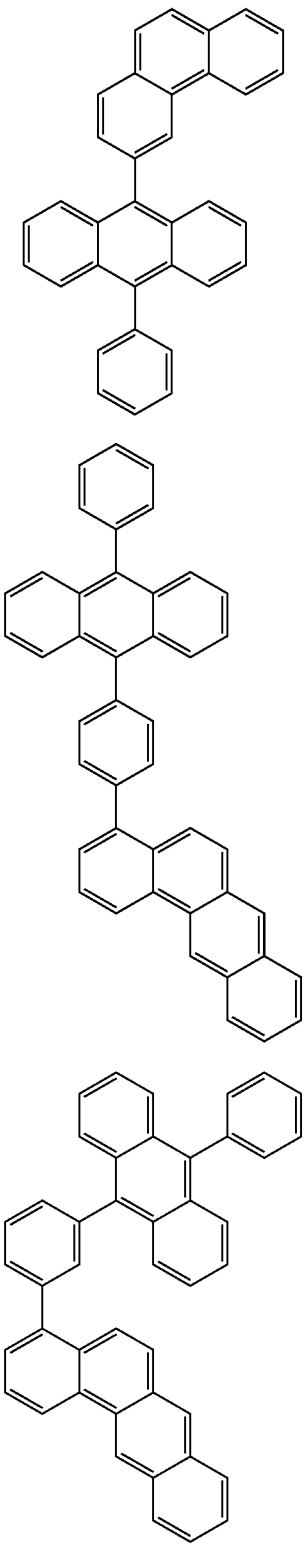

Besides the compounds of the formula (I), suitable charge-transport materials, as can be used in the hole-injection or hole-transport layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Ba/Ag or Mg/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carriergas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

The organic electroluminescent devices comprising one or more compounds of the formula (I) can be employed in accordance with the invention in displays, as light sources in lighting applications and as light sources in medical and/or cosmetic applications (for example light therapy).

On use of the compounds of the formula (I) in organic electroluminescent devices, one or more of the advantages indicated below can be achieved:

The compounds of the formula (I) are very highly suitable for use as matrix materials for phosphorescent dopants and also highly suitable for use as electron-transport materials. On use of the compounds according to the invention in these functions, good power efficiencies, low operating voltages and good lifetimes of the organic electroluminescent devices are obtained.

Furthermore, the compounds of the formula (I) are distinguished by high oxidation stability in solution, which has an advantageous effect during purification and handling of the compounds and on use thereof in electronic devices.

Furthermore, the compounds of the formula (I) are temperature-stable and can thus be sublimed substantially without decomposition. Purification of the compounds is thus simplified, and the compounds can be obtained in higher purity, which has a positive effect on the performance data of the electronic devices comprising the materials. In particular, devices having longer operating lifetimes can thus be produced.

The invention is explained in greater detail by the following working examples, without wishing it to be restricted thereby.

USE EXAMPLES

A) Synthesis Examples

The following syntheses are carried out, unless indicated otherwise, under a protective-gas atmosphere in dried solvents. Benzo[b]thiophene and solvents can be purchased commercially, for example from ALDRICH.

1) Synthesis of compound 1: 6-o-Biphenylbis[1]-benzothieno[2,3-b:3',2'-d]-pyrrole Scheme for the Synthesis of Compounds 1 and 2

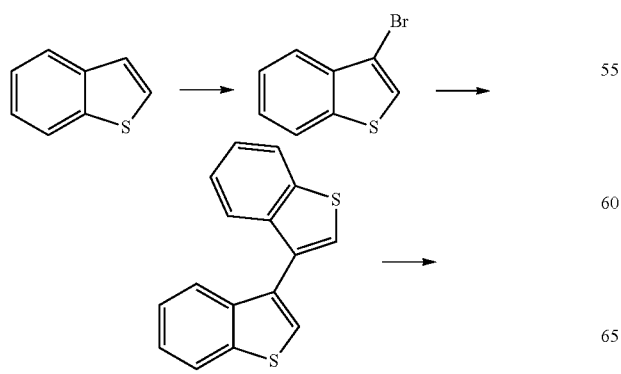

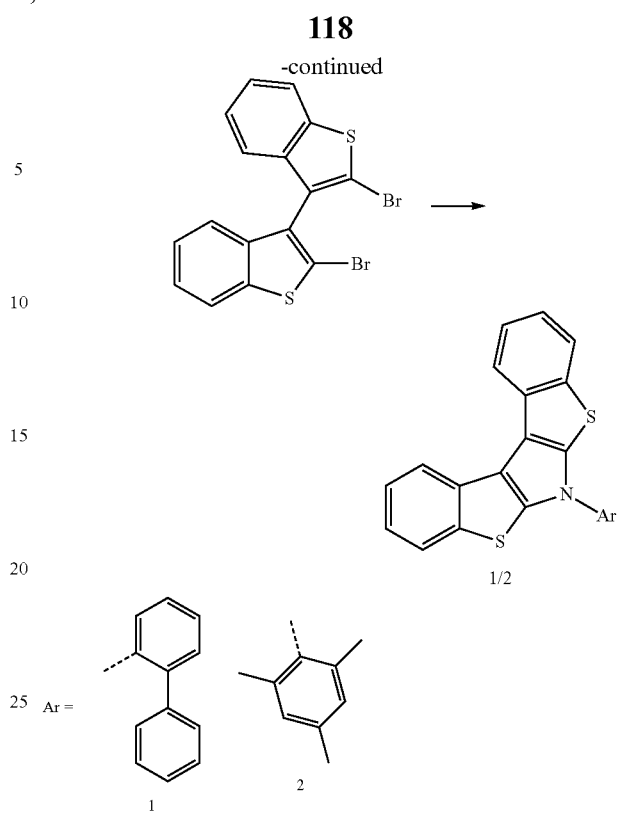

Step 1-a: 3-Bromobenzo[b]thiophene

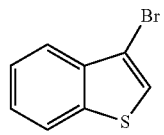

100 g (745 mmol) of benzo[b]thiophene are suspended in 1000 ml of chloroform and 1000 ml of glacial acetic acid with 145 g (815 mmol) of NBS and stirred at room temperature for 24 h. After a TLC check, the batch is evaporated under reduced pressure. The purification is carried out by distillation of the product and gives a red oil (111 g; 73%).

Step 1-b: [3,3]-Bisbenzo[b]thiophenyl

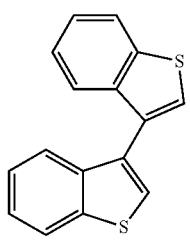 [SMILES: c1ccc2c(-c3csc4ccccc34)csc2c1]

3000 ml of THF, 40 g (61 mmol) of bis(triphenylphosphine)nickel(II) chloride, 34.3 g (524.6 mmol) of zinc and 101.6 g (275 mmol) of n-Bu$_4$NI are added to 50 g (235 mmol) of the compound from the preceding step. The batch is heated at 70° C. for 20 h, then cooled to room temperature, and 400 ml of water are added. The mixture is extracted with ethyl acetate, the combined organic phases are then dried over sodium sulfate and evaporated under reduced pressure. The purification is carried out by recrystallisation (heptane/MeOH) and gives a white solid (22 g, 71.7 mmol, 61%).

Step 1-c: 2,2'-Dibromo-[3,3']-bisbenzo[b]thiophenyl

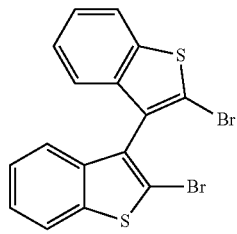 [SMILES: Brc1sc2ccccc2c1-c1c(Br)sc2ccccc12]

10 g (37.5 mmol) of the compound from the preceding step are initially introduced in 250 ml of acetic acid. With exclusion of light, a solution of 8 ml (24 g, 150 mmol) of Br$_2$ in 10 ml of acetic acid is added dropwise at −5° C. The mixture is subsequently allowed to come to room temperature and is stirred at this temperature for a further 24 h. 150 ml of water are then added to the mixture, which is then extracted with CH$_2$Cl$_2$. The organic phase is dried over MgSO$_4$, and the solvents are removed in vacuo. The product is washed by stirring with hot hexane and filtered off with suction. Yield: 14 g (33 mmol), 83.5%. Purity according to $^1$H-NMR about 98%.

Compound 1: 6-o-Biphenylbis-[1]benzothieno[2,3-b:3',2'-d]pyrrole

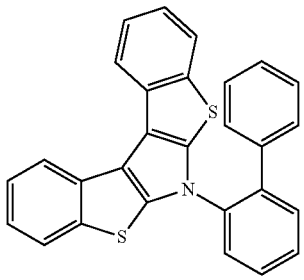

500 ml of toluene, 2.3 g (2.5 mmol) of tris(dibenzylideneacetone)dipalladium, 10 ml of 1M t-Bu$_3$P in toluene and 11.5 g (120 mmol) of sodium tert-butoxide are added to 21.2 g (50 mmol) of the compound from the preceding step. 6.8 g (40 mmol) of 2-aminobiphenyl are subsequently added. The batch is heated at 110° C. for 20 h, then cooled to room temperature, and 400 ml of water are added. The mixture is extracted with ethyl acetate, the combined organic phases are then dried over sodium sulfate and evaporated under reduced pressure. The residue is recrystallised from toluene and from dichloromethane/isopropanol and finally sublimed in a high vacuum. The purity is 99.9%. The yield is 10.6 g (24.5 mmol), corresponding to 49% of theory.

2) Synthesis of compound 2: 2,4,6-Trimethylphenylbis[1]benzothieno-[2,3-b:3',2'-d]pyrrole

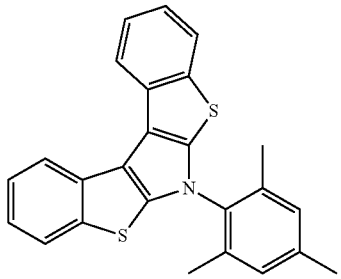

500 ml of toluene, 2.3 g (2.5 mmol) of tris(dibenzylideneacetone)dipalladium, 10 ml of 1M t-Bu$_3$P in toluene and 11.5 g (120 mmol) of sodium tert-butoxide are added to 21.2 g (50 mmol) of the compound from step 1-c. 5.4 g (40 mmol) of 2,4,6-trimethylaniline are subsequently added. The batch is heated at 110° C. for 20 h, then cooled to room temperature, and 400 ml of water are added. The mixture is extracted with ethyl acetate, the combined organic phases are then dried over sodium sulfate and evaporated under reduced pressure. The residue is recrystallised from toluene and from heptane/methanol and finally sublimed in a high vacuum. The purity is 99.9%. The yield is 11.5 g (29 mmol), corresponding to 58% of theory.

3) Synthesis of compound 3: 2,4,6-Triphenylpyrimidinylbis[1]-benzothieno-[2,3-b:3',2'-d]pyrrole Scheme for the Synthesis of Compound 3

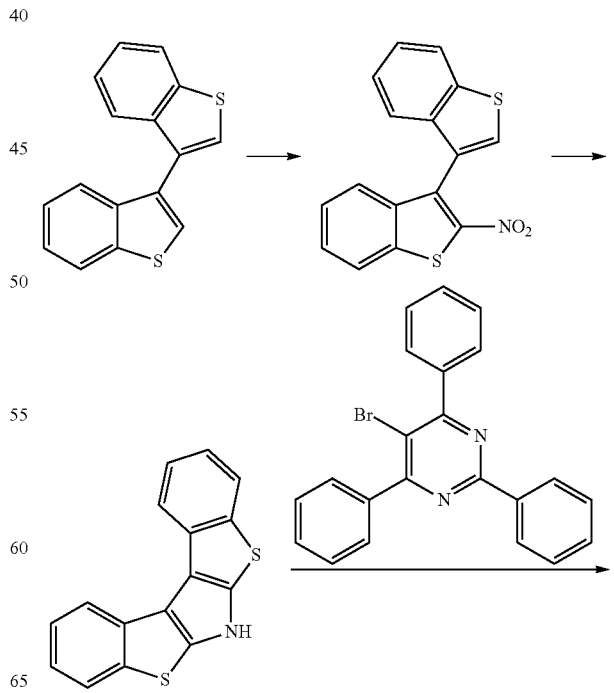

-continued

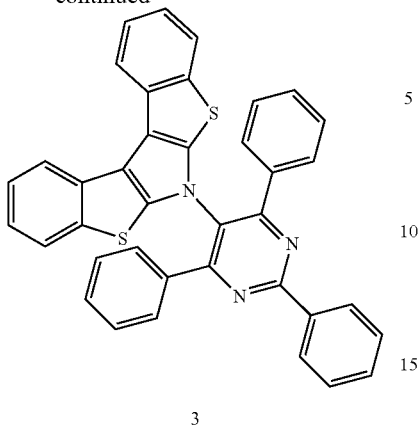

Step 3-a: 2-Nitro-3,3'-bisbenzo[b]thiophene

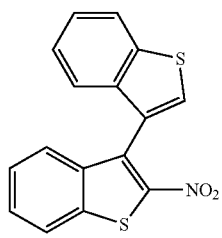 [SMILES: O=[N+]([O-])c1sc2ccccc2c1-c1csc2ccccc12]

12.6 g (47 mmol) of 3,3'-dibenzo[b]thiophene are initially introduced in 1000 ml of glacial acetic acid. The batch is warmed to a bath temperature of 60° C., and a mixture of 4 ml of conc. HNO₃ and 200 ml of glacial acetic acid is added. The mixture is subsequently stirred at 65° C. for 1 h and poured into ice-water. The yellow solid formed in the process is filtered off with suction. The product is washed by stirring with hot hexane and filtered off with suction. Yield: 13.5 g (43 mmol), 96% of theory, purity according to ¹H-NMR about 98%.

Step 3-b: 6H-Bis[1]benzothieno[2,3-b:3',2'-d]pyrrole

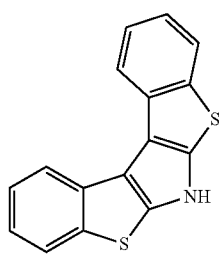 [SMILES: c1ccc2c(c1)sc1[nH]c3sc4ccccc4c3c12]

11.7 g (42 mmol) of the compound from the preceding step and 29 ml (165 mmol) of triethyl phosphite are dissolved in 350 ml of 1,2-dichlorobenzene and stirred at 150° C. for 24 h. After cooling, the solvent is distilled off. The purification is carried out by recrystallisation (heptane) and gives a colourless solid (3.5 g, 12.6 mmol, 30%). Purity according to ¹H-NMR about 90%.

Step 3-c: 5-Bromo-2,4,6-triphenylpyrimidine

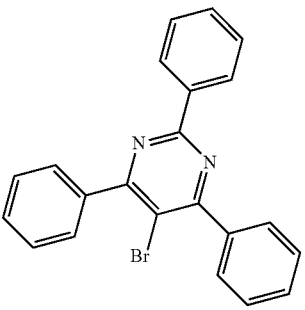 [SMILES: Brc1c(-c2ccccc2)nc(-c2ccccc2)nc1-c1ccccc1]

50 g (177 mmol) of trifluoromethanesulfonic anhydride and 36.5 g (354 mmol) of benzonitrile are dissolved in 300 ml of dichloromethane. A solution of dichloromethane and 35.2 g (177 mmol) of 2-bromoacetophenone is added dropwise to this solution at room temperature. The reaction mixture is left to stir at RT for 24 h. The batch is washed with aqueous NaHCO₃ solution, and the organic phase is dried using MgSO₄ and evaporated to dryness in a rotary evaporator. The product is washed by stirring with hot ethanol and filtered off with suction. Yield: 33.5 g (86.5 mmol), 49% of theory, purity according to ¹H-NMR about 98%.

Compound 3: 2,4,6-Triphenylpyrimidinylbis[1]benzothieno[2,3-b:3',2'-d]-pyrrole

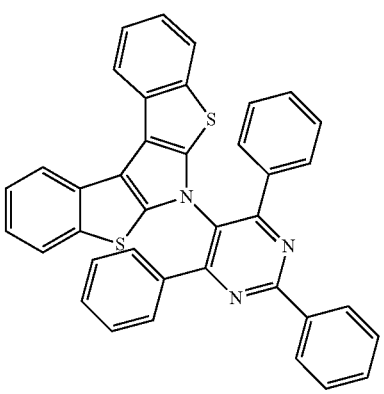

9.1 g (23.5 mmol) of the compound from the preceding step, 13.11 g (47 mmol) of 6H-bis[1]benzothieno[2,3-b:3', 2'-d]pyrrole and 29.2 g of Rb₂CO₃ are suspended in 250 ml of p-xylene. 0.95 g (4.2 mmol) of Pd(OAc)₂ and 12.6 ml of a 1M tri-tert-butylphosphine solution are added to this suspension. The reaction mixture is heated under reflux for 24 h. After cooling, the organic phase is separated off, washed three times with 200 ml of water and subsequently evaporated to dryness. The residue is extracted with hot toluene, recrystallised three times from toluene and finally sublimed in a high vacuum, giving 5.6 g (9.7 mmol) of the product, corresponding to 41% of theory. The purity is 99.9%.

4) Synthesis of compound 4: 3-((Z)-Buta-1,3-dienyl)-1-[3-(4,6-diphenyl-1,3,5-triazin-2-yl)phenyl]-2-methyl-1H-benzo[4,5]thieno[2,3-b]pyrrole Scheme for the Synthesis of Compound 4

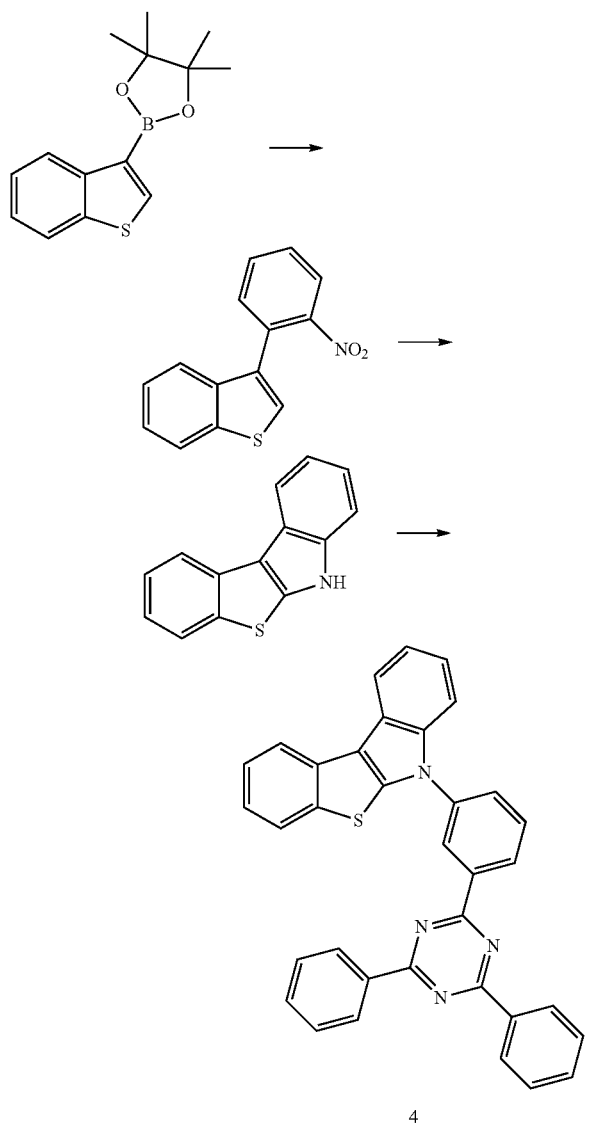

4

Step 4-a: 2-Benzo[b]thiophen-3-yl-4,4,5,5-tetramethyl-1,3,2-dioxaborolane

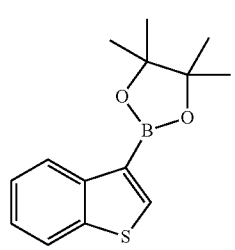 [SMILES: CC1(C)OB(c2csc3ccccc23)OC1(C)C]

1600 ml of THF, 145 g (568 mmol) of bis(pinacolato)diborane and 142 g (1.45 mol) of potassium acetate are added to 111 g (516 mmol) of 3-bromobenzo[b]thiophene. 10 g (12 mmol) of 1,1-bis(diphenylphosphino)ferrocenepalladium(II) chloride (complex with dichloromethane (1:1), Pd 13%) are subsequently added. The batch is heated at 70° C. for 16 h, then cooled to room temperature, and 400 ml of water are added. The mixture is extracted with ethyl acetate, the combined organic phases are then dried over sodium sulfate and evaporated under reduced pressure. The purification is carried out by recrystallisation (heptane/MeOH) and gives a brown solid (78 g, 58.3%).

Step 4-b: 2-Nitrophenylbenzo[b]thiophene

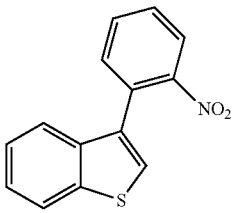 [SMILES: O=[N+]([O-])c1ccccc1-c1csc2ccccc12]

56 g (0.225 mol) of the compound from the preceding step, 70.2 g (1.2 molar equivalents, 0.270 mol) of 1-iodonitrobenzene and 286 g (1.345 mol) of tripotassium phosphate are suspended in 700 ml of toluene, 700 ml of dioxane and 700 ml of water. 0.684 g (2.25 mmol) of tri-o-tolylphosphine and then 2.53 g (11.2 mmol) of palladium(II) acetate are added to this suspension, and the reaction mixture is heated under reflux for 21 h. After cooling, the organic phase is separated off. The aqueous phase is extracted with dichloromethane, the combined organic phases are then dried over sodium sulfate, filtered and evaporated under reduced pressure. The residue is chromatographed over silica gel. The yield is 39 g (152 mmol), corresponding to 68% of theory.

Step 4-c: 6H-[1]Benzothieno[2,3-b]indole

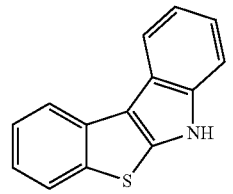 [SMILES: c1ccc2c(c1)[nH]c1sc3ccccc3c12]

32 g (0.124 mol) of the compound from the preceding step and 86 ml (0.495 mol) of triethyl phosphite are dissolved in 1000 ml of 1,2-dichlorobenzene and stirred at 150° C. for 72 h. After cooling, the solvent is distilled off. The purification is carried out by recrystallisation (heptane) and gives a colourless solid (12 g, 45.3%).

Compound 4: 3-((Z)-Buta-1,3-dienyl)-1-[3-(4,6-diphenyl-1,3,5-triazin-2-yl)phenyl]-2-methyl-1H-benzo[4,5]thieno[2,3-b]pyrrole

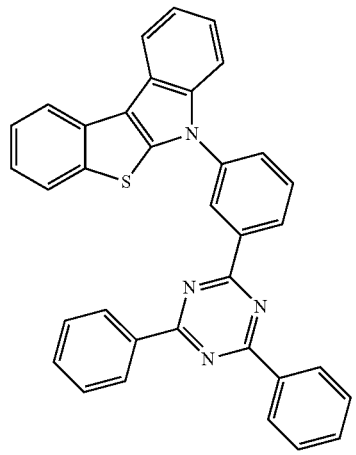

9.1 g (23.5 mmol) of 5-bromo-2,4,6-triphenylpyrimidine, 13.11 g (47 mmol) of 6H-[1]benzothieno[2,3-b]indole and 29.2 g of Rb$_2$CO$_3$ are suspended in 250 ml of p-xylene. 0.95 g (4.2 mmol) of Pd(OAc)$_2$ and 12.6 ml of a 1M tri-tert-butylphosphine solution are added to this suspension. The reaction mixture is heated under reflux for 24 h. After cooling, the organic phase is separated off, washed three times with 200 ml of water and subsequently evaporated to dryness. The residue is extracted with hot toluene and recrystallised three times from toluene and finally sublimed in a high vacuum, giving 5.6 g (9.7 mmol) corresponding to 41% of theory, the purity is 99.9%.

5) Synthesis of Compound 5

Scheme for the Synthesis of Compound 5

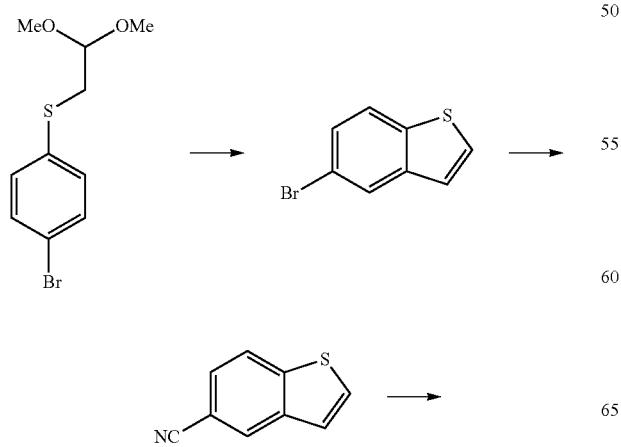

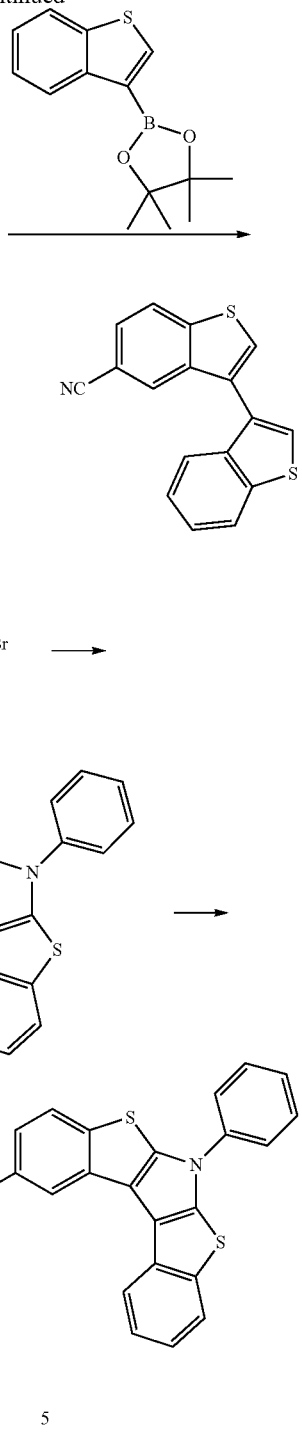

Step 5-a: 5-Bromobenzo[b]thiophene

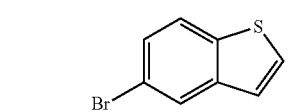

97.2 g (351 mmol) of 1-bromo-4-[(2,2-dimethoxyethyl)sulfanyl]benzene and 100 g of polyphosphoric acid are dissolved in 2000 ml of chlorobenzene and stirred at 135° C. for 4 h. After cooling, the solvent is distilled off. The residue is extracted with dichloromethane, and the organic phase is washed three times with 200 ml of water. The combined organic phases are then dried over sodium sulfate, filtered and evaporated under reduced pressure. The purification is carried out by recrystallisation (heptane) and gives a colourless solid (60.3 g, 283 mmol, 80.1%).

Step 5-b: Benzo[b]thiophene-5-carbonitrile

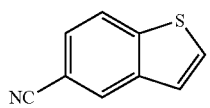 [SMILES: N#Cc1ccc2sccc2c1]

45 g (211 mmol) of the compound from the preceding step, 26.18 g (295 mmol) of copper(I) cyanide and 25 ml of pyridine are dissolved in 500 ml of N,N-dimethylformamide and stirred at 130° C. for 24 h. After cooling, the solvent is distilled off. The residue is extracted with dichloromethane, and the organic phase is washed three times with 200 ml of water. The combined organic phases are then dried over sodium sulfate, filtered and evaporated under reduced pressure. The residue is chromatographed over silica gel. The purification is carried out by recrystallisation (heptane) and gives a colourless solid (18.9 g, 118.2 mmol, 56%).

Step 5-c: 3-Bromo-1-benzothiophene-6-carbonitrile

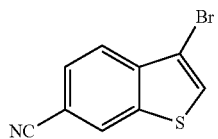 [SMILES: N#Cc1ccc2c(Br)csc2c1]

23.7 g (149 mmol) of the compound from the preceding step are suspended in 200 ml of chloroform and 200 ml of glacial acetic acid with 29 g (163 mmol) of NBS and stirred at RT for 24 hrs. After a TLC check, the batch is evaporated under reduced pressure. The purification is carried out by distillation of the product and gives a red oil (12.5 g, 52.15 mmol, 35% of theory).

Step 5-d

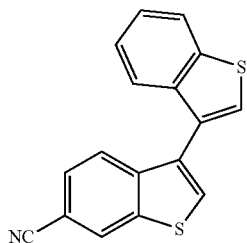 [SMILES: N#Cc1ccc2c(-c3csc4ccccc34)csc2c1]

16.4 g (56.25 mmol) of 3-bromo-1-benzothiophene-6-carbonitrile, 17.55 g (67.5 mmol) of 2-benzo[b]thiophen-3-yl-4,4,5,5-tetramethyl-1,3,2-dioxaborolane and 71.5 g (6.0 molar equivalents, 0.335 mol) of tripotassium phosphate are suspended in 500 ml of toluene, 500 ml of dioxane and 250 ml of water. 0.180 g (0.56 mmol) of tri-o-tolylphosphine and then 0.63 g (2.8 mmol) of palladium(II) acetate are added to this suspension, and the reaction mixture is heated under reflux for 24 h. After cooling, the organic phase is separated off. The aqueous phase is extracted with dichloromethane, the combined organic phases are then dried over sodium sulfate, filtered and evaporated under reduced pressure. The residue is chromatographed over silica gel. The yield is 7.4 g (25.3 mmol), corresponding to 45% of theory.

Step 5-e

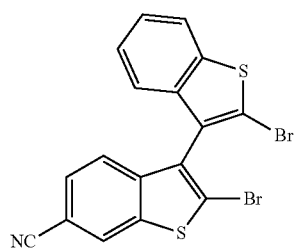 [SMILES: N#Cc1ccc2c(-c3c(Br)sc4ccccc34)c(Br)sc2c1]

11.06 g (37.5 mmol) of the compound from the preceding step is initially introduced in 250 ml of acetic acid. A solution of 8 ml (24 g, 150 mmol) of $Br_2$ in 10 ml of acetic acid is subsequently added dropwise with exclusion of light at −5° C., the mixture is allowed to come to RT and is stirred further at this temperature for 24 h. 150 ml of water are then added to the mixture, which is then extracted with $CH_2Cl_2$. The organic phase is dried over $MgSO_4$, and the solvents are removed in vacuo. The product is washed by stirring with hot hexane and filtered off with suction. Yield: 10.11 g (22.5 mmol), 60.5% of theory, purity according to $^1$H-NMR about 98%.

Step 5-f

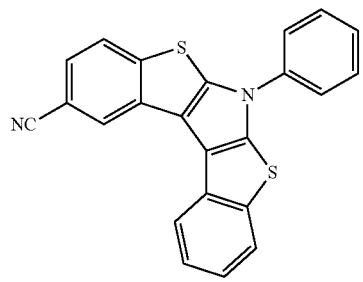 [SMILES: N#Cc1ccc2sc3c(c2c1)c1c2ccccc2sc1n3-c1ccccc1]

200 ml of toluene are added to 8.98 g (20 mmol) of the compound from the preceding step, 0.95 g (1 mmol) of tris(dibenzylideneacetone)dipalladium, 4 ml of 1M t-$Bu_3$P solution in toluene and 4.6 g (48 mmol) of sodium tert-butoxide. 1.8 g (16 mmol) of aniline are subsequently added. The batch is heated at 110° C. for 20 h, then cooled to room temperature, and 100 ml of water are added. The mixture is extracted with ethyl acetate, the combined organic phases are then dried over sodium sulfate and evaporated under reduced pressure. The residue is recrystallised from toluene and from heptane/methanol. The yield is 3.3 g (8.64 mmol), corresponding to 48% of theory. Purity according to $^1$H-NMR about 96%.

Compound 5

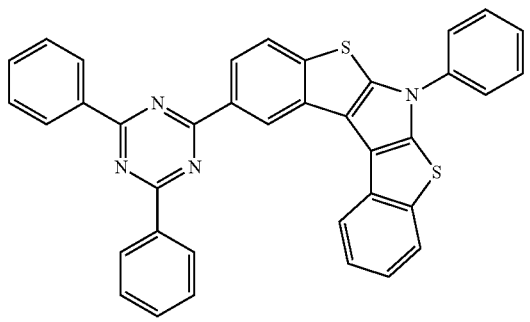

Ethanol (50 ml) and sodium hydroxide solution (20 ml) are added to 3.3 g (8.64 mmol) of the compound from the preceding step. The reaction mixture is stirred under reflux for 6 h. After cooling to 25° C., the solution is evaporated in vacuo. 50 ml of 5M HCl are subsequently added slowly. The precipitated solid is filtered off and washed with water. The yield is 3.1 g (7.8 mmol), corresponding to 91% of theory. Purity according to $^1$H-NMR about 95%.

Thionyl chloride (50 ml) is added to the carboxylic acid obtained (3.1 g, 7.8 mmol). The reaction mixture is warmed to 80° C. and heated under reflux for 2 h. The solvent is then removed in vacuo. The carboxylic acid chloride is obtained in a yield of 2.9 g (7.7 mmol, 98% of theory).

1.0 g (7.6 mmol) of aluminium trichloride, 2.9 g (7.7 mmol) of the carboxylicacid chloride, 0.18 ml (2.3 mmol) of thionyl chloride and 1.6 ml (15.8 mmol) of benzonitrile are dissolved in 80 ml of 1,2-dichlorobenzene. The batch is firstly warmed to 110° C., and 0.8 g (15.2 mmol) of ammonium chloride is then added. The batch is subsequently heated at 110° C. for 20 h, then cooled to room temperature, and 100 ml of methanol are added. The solid is filtered off with suction and washed with ethanol. The residue is chromatographed over silica gel, extracted with hot toluene, recrystallised three times from toluene and finally sublimed in a high vacuum, giving 2.2 g (3.9 mmol), corresponding to 29% of theory. The purity is 99.9%.

B) Device Examples

OLEDs according to the invention and OLEDs in accordance with the prior art are produced by a general process in accordance with WO 04/058911, which is adapted to the circumstances described here (layer-thickness variation, materials).

In Examples V1 to E8 below (see Tables 1 and 2), the data for various OLEDs are presented. Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs basically have the following layer structure: substrate/hole-transport layer (HTL)/interlayer (IL)/electron-blocking layer (EBL)/emission layer (EML)/optional hole-blocking layer (HBL)/electron-transport layer (ETL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), to which the matrix material or materials is (are) admixed by co-evaporation in a certain proportion by volume. An expression such as ST1:HTM4: TEG1 (30%:60%:10%) here means that the material ST1 is present in the layer in a proportion by volume of 30%, HTM4 is present in the layer in a proportion of 60% and TEG1 is present in the layer in a proportion of 10%. Analogously, the electron-transport layer may also consist of a mixture of two materials.

The OLEDs are characterised by standard methods. To this end, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), and the lifetime are determined. The electroluminescence spectra are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. CE1000 and PE1000 denote the current and power efficiency respectively which are achieved at 1000 cd/m$^2$. Finally, EQE1000 is the external quantum efficiency at an operating luminous density of 1000 cd/m$^2$. The lifetime LT is defined as the time after which the luminous density has dropped from the initial luminous density L0 to a certain proportion L1 on operation at constant current. The expression L0=4000 cd/m$^2$ and L1=80% in Table 2 means that the lifetime indicated in column LT corresponds to the time after which the initial luminous density of the corresponding OLED has dropped from 4000 cd/m$^2$ to 3200 cd/m$^2$. The values for the lifetime can be converted into a value for other initial luminous densities with the aid of conversion formulae known to the person skilled in the art. The lifetime for an initial luminous density of 1000 cd/m$^2$ is the usual figure quoted here.

The data for the various OLEDs are summarised in Table 2. Examples V1 and V2 are comparative examples in accordance with the prior art, while Examples E1 to E8 show data for OLEDs comprising materials according to the invention.

Some of the examples are explained in greater detail below in order to illustrate the advantages of the compounds according to the invention. However, it should be pointed out that this only represents a selection of the data shown in Table 2.

Use of Compounds According to the Invention as Hole-Transport or Electron-Blocking Materials On use of materials HTM1 and HTM2 in accordance with the prior art in green-phosphorescent OLEDs, good efficiency and also operating voltage are obtained. However, the lifetime on use of the compounds is very short (Ex. V1, V2). By contrast, with materials HTM3 and HTM4 according to the invention, good efficiency and voltage are likewise obtained, but a good lifetime is also obtained (Ex. E1, E2).

Use of Compounds According to the Invention as Matrix Materials in Phosphorescent OLEDs If materials HTM3 and HTM4 according to the invention are used as second component in a mixed matrix, good efficiency, lifetime and also voltage are obtained (Ex. E3, E4).

Furthermore, the triazine- or pyrimidine-substituted compounds M2-M4 according to the invention can also be employed as individual matrix materials, where good efficiencies, lifetimes and operating voltages are again obtained (Ex. E5 to E8).

TABLE 1

Structure of the OLEDs

| Ex. | HTL Thickness | IL Thickness | EBL Thickness | EML Thickness | HBL Thickness | ETL Thickness |
|---|---|---|---|---|---|---|
| V1 | SpA1 70 nm | HATCN 5 nm | HTM1 90 nm | IC1:TEG1 (90%:10%) 30 nm | ST1 10 nm | ST1:LiQ (50%:50%) 30 nm |
| V2 | SpA1 70 nm | HATCN 5 nm | HTM2 90 nm | IC1:TEG1 (90%:10%) 30 nm | ST1 10 nm | ST1:LiQ (50%:50%) 30 nm |
| E1 | SpA1 70 nm | HATCN 5 nm | HTM3 90 nm | IC1:TEG1 (90%:10%) 30 nm | ST1 10 nm | ST1:LiQ (50%:50%) 30 nm |
| E2 | SpA1 70 nm | HATCN 5 nm | HTM4 90 nm | IC1:TEG1 (90%:10%) 30 nm | ST1 10 nm | ST1:LiQ (50%:50%) 30 nm |
| E3 | SpA1 70 nm | HATCN 5 nm | BPA1 90 nm | ST1:HTM3:TEG1 (30%:60%:10%) 30 nm | — | ST1:LiQ (50%:50%) 30 nm |
| E4 | SpA1 70 nm | HATCN 5 nm | BPA1 90 nm | ST1:HTM4:TEG1 (30%:60%:10%) 30 nm | — | ST1:LiQ (50%:50%) 30 nm |
| E5 | SpA1 70 nm | HATCN 5 nm | BPA1 90 nm | M2:TEG1 (90%:10%) 30 nm | ST1 10 nm | ST1:LiQ (50%:50%) 30 nm |
| E6 | SpA1 70 nm | HATCN 5 nm | BPA1 90 nm | M3:TEG1 (90%:10%) 30 nm | ST1 10 nm | ST1:LiQ (50%:50%) 30 nm |
| E7 | SpA1 70 nm | HATCN 5 nm | BPA1 90 nm | M3:TEG1 (90%:10%) 30 nm | — | ST1:LiQ (50%:50%) 30 nm |
| E8 | SpA1 70 nm | HATCN 5 nm | BPA1 90 nm | M4:TEG1 (90%:10%) 30 nm | ST1 10 nm | ST1:LiQ (50%:50%) 30 nm |

TABLE 2

Data for the OLEDs

| Ex. | U1000 (V) | CE1000 (cd/A) | PE1000 (lm/W) | EQE 1000 | CIE x/y at 1000 cd/m$^2$ | L0 (cd/m$^2$) | L1 % | LT (h) |
|---|---|---|---|---|---|---|---|---|
| V1 | 3.7 | 54 | 46 | 14.9% | 0.36/0.60 | 4000 | 80 | 45 |
| V2 | 3.9 | 48 | 39 | 13.4% | 0.36/0.60 | 4000 | 80 | 30 |
| E1 | 3.6 | 49 | 43 | 13.6% | 0.36/0.60 | 4000 | 80 | 360 |
| E2 | 3.8 | 56 | 46 | 15.4% | 0.36/0.60 | 4000 | 80 | 385 |
| E3 | 3.9 | 52 | 42 | 14.4% | 0.37/0.61 | 4000 | 80 | 460 |
| E4 | 3.8 | 54 | 45 | 15.1% | 0.37/0.61 | 4000 | 80 | 480 |
| E5 | 3.7 | 47 | 40 | 13.0% | 0.36/0.60 | 4000 | 80 | 340 |
| E6 | 3.4 | 54 | 50 | 15.5% | 0.37/0.59 | 4000 | 80 | 305 |
| E7 | 3.5 | 56 | 51 | 15.7% | 0.38/0.59 | 4000 | 80 | 280 |
| E8 | 3.5 | 53 | 47 | 14.8% | 0.36/0.60 | 4000 | 80 | 260 |

TABLE 3

Structural formulae of the materials for the OLEDs

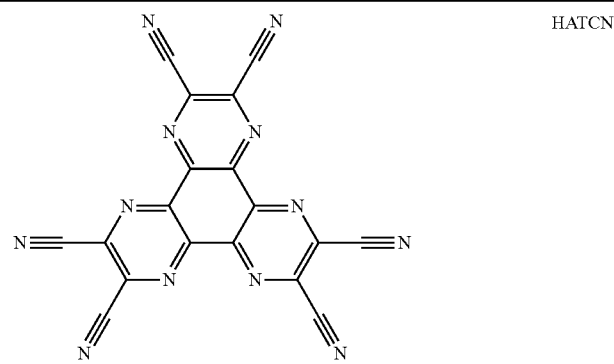

HATCN

TABLE 3-continued
Structural formulae of the materials for the OLEDs
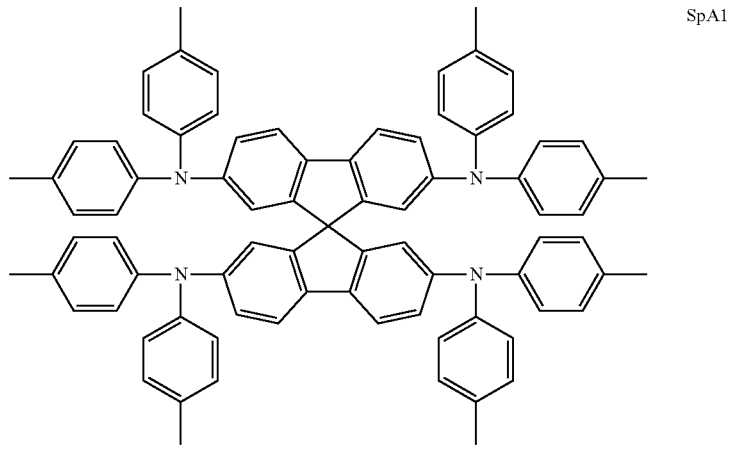
SpA1
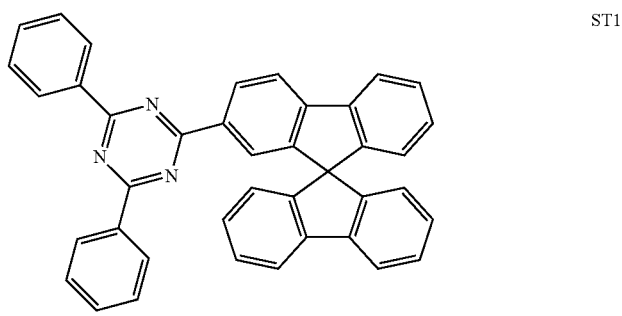
ST1
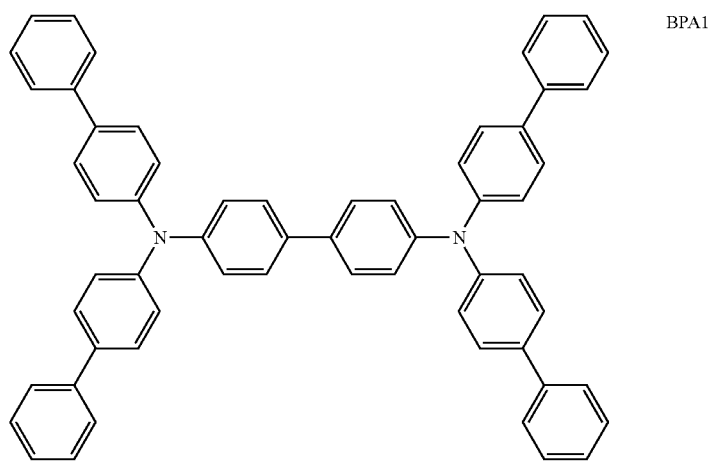
BPA1
LiQ TABLE 3-continued
Structural formulae of the materials for the OLEDs
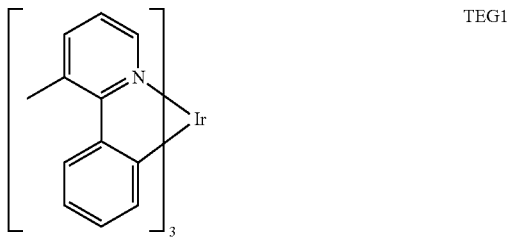
TEG1
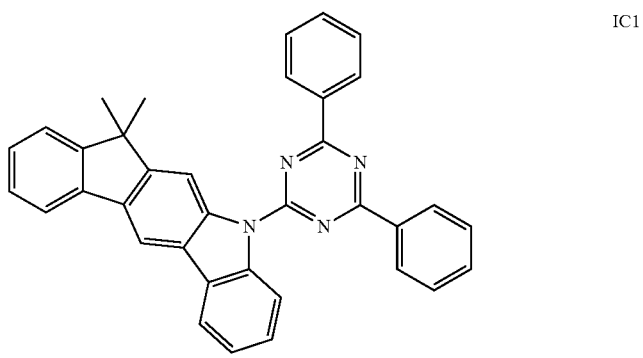
IC1
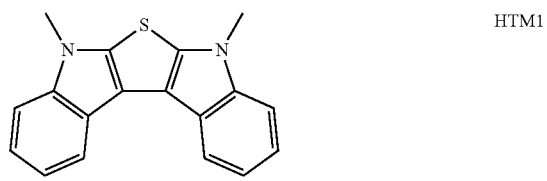
HTM1
(prior art)
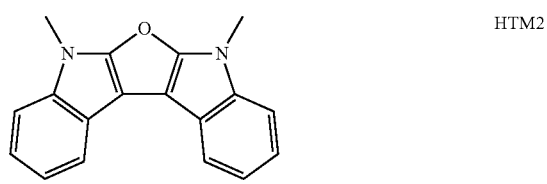
HTM2
(prior art)
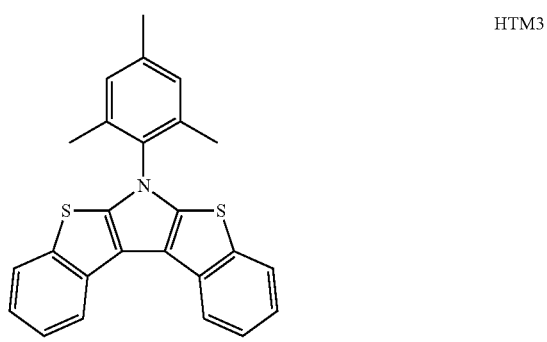
HTM3
(compound 2 of the synthesis examples)

TABLE 3-continued
Structural formulae of the materials for the OLEDs
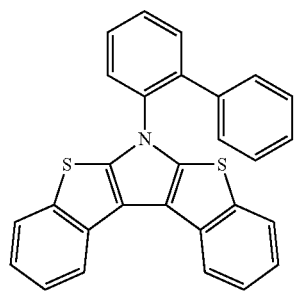
HTM4
(compound 1 of the synthesis examples)
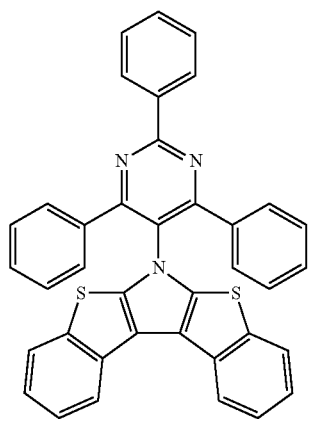
M2
(compound 3 of the synthesis examples)
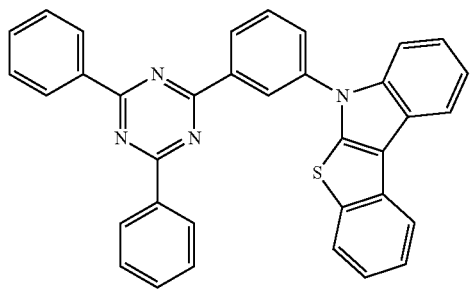
M3
(compound 4 of the synthesis examples)
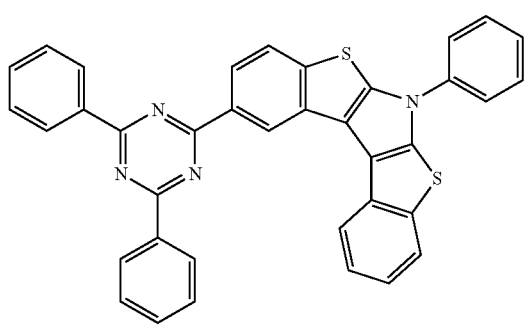
M4
(compound 5 of the synthesis examples)

The invention claimed is:

1. A compound of the formulae (Ia-1)-(Ia-10), (Ib-5)-(Ib-8), (Ib-11)-(Ib-19) or (Ib-20)

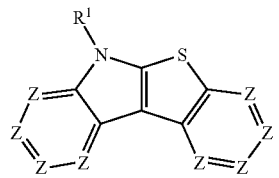
formula (Ia-1)

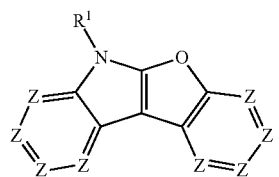
formula (Ia-2)

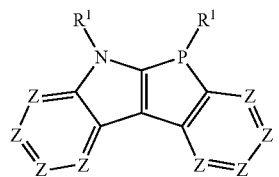
formula (Ia-3)

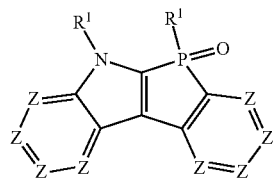
formula (Ia-4)

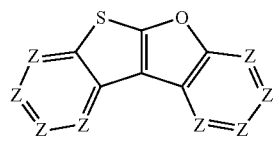
formula (Ia-5)

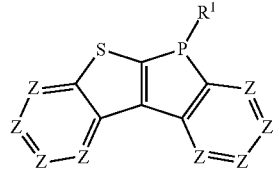
formula (Ia-6)

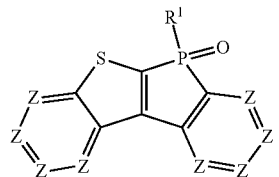
formula (Ia-7)

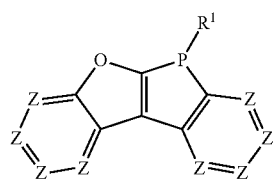
formula (Ia-8)

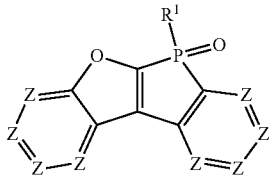
formula (Ia-9)

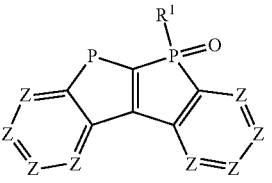
formula (Ia-10)

where the following applies to the symbols and indices occurring:

Z is on each occurrence, identically or differently, $CR^2$ or N, where not more than two adjacent groups Z may simultaneously be equal to N;

$R^1$ is on each occurrence, identically or differently, $C(=O)R^3$, $CR^3=C(R^3)_2$, $C(=O)OR^3$, $C(=O)NR^3_2$, $P(=O)(R^3)_2$, $OR^3$, $S(=O)R^3$, $S(=O)_2R^3$, or an aromatic or heteroaromatic ring system having 5 to 60 aromatic ring atoms, which optionally in each case be substituted by one or more radicals $R^3$, or a combination of these systems, where two or more radicals $R^1$ are optionally linked to one another and may form an aliphatic or aromatic ring;

$R^2$ is on each occurrence, identically or differently, H, D, F, Cl, Br, I, $B(OR^3)_2$, CHO, $C(=O)R^3$, $CR^3=C(R^3)_2$, CN, $C(=O)OR^3$, $C(=O)NR^3_2$, $Si(R^3)_3$, $N(R^3)_2$, $NO_2$, $P(=O)(R^3)_2$, $OS(=O)_2R^3$, OH, $S(=O)R^3$, $S(=O)_2R^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals $R^3$ and where one or more non-adjacent $CH_2$ groups is optionally replaced by $-R^3C=CR^3-$, $-C\equiv C-$, $Si(R^3)_2$, $Ge(R^3)_2$, $Sn(R^3)_2$, C=O, C=S, C=Se, $C=NR^3$, $-C(=O)O-$, $-C(=O)NR^3-$, $NR^3$, $P(=O)(R^3)$, $-O-$, $-S-$, S=O or $S(=O)_2$ and where one or more H atoms in the above-mentioned groups is optionally replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 60 aromatic ring atoms, which is optionally substituted by one or more radicals $R^3$, or a combination of these systems, where two or more radicals $R^2$ are optionally linked to one another and may form an aliphatic or a condensed aryl or heteroaryl group;

$R^3$ is on each occurrence, identically or differently, H, D, F, Cl, Br, I, $B(OR^4)_2$, CHO, $C(=O)R^4$, $CR^4=C(R^4)_2$, CN, $C(=O)OR^4$, $C(=O)NR^4_2$, $Si(R^4)_3$, $N(R^4)_2$, $NO_2$, $P(=O)(R^4)_2$, $OS(=O)_2R^4$, OH, $S(=O)R^4$, $S(=O)_2R^4$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals $R^4$ and where one or more non-adjacent $CH_2$ groups in the above-mentioned groups is optionally replaced by —$R^4C=CR^4$—, —C≡C—, $Si(R^4)_2$, $Ge(R^4)_2$, $Sn(R^4)_2$, C=O, C=S, C=Se, C=$NR^4$, —C(=O)O—, —C(=O)$NR^4$—, $NR^4$, P(=O)($R^4$), —O—, —S—, S=O or S(=O)$_2$ and where one or more H atoms in the above-mentioned groups is optionally replaced by D, F, Cl, Br, I, CN or $NO_2$, or an aromatic or heteroaromatic ring system having 5 to 60 aromatic ring atoms, which may in each case be substituted by one or more radicals $R^4$, or an aryloxy or heteroaryloxy group having 5 to 60 aromatic ring atoms, which is optionally substituted by one or more radicals $R^4$, or a combination of these systems, where two or more radicals $R^3$ are optionally linked to one another and may form an aliphatic or aromatic ring; and $R^4$ is, identically or differently on each occurrence, H, D, F or an aliphatic, aromatic and/or heteroaromatic organic radical having 1 to 20 C atoms, in which, in addition, one or more H atoms is optionally replaced by D or F; two or more substituents $R^4$ here may also be linked to one another and form an aliphatic or aromatic ring.

2. The compound according to claim 1, wherein 0, 1 or 2 groups Z per aromatic or heteroaromatic six-membered ring are equal to N.

3. The compound according to claim 1, wherein $R^1$ represents on each occurrence, identically or differently, an aromatic or heteroaromatic ring system having 5 to 30 aromatic ring atoms, which optionally in each case be substituted by one or more radicals $R^3$.

4. The compound according to claim 1, wherein at least one group is present as substituent $R^1$ or $R^2$ which is selected from electron-deficient heteroaryl groups, aromatic or heteroaromatic ring systems having 10 to 30 aromatic ring atoms and from arylamine groups, each of which is optionally substituted by one or more radicals as defined in claim 1.

5. A process for the preparation of the compound of the formulae (Ia-1)-(Ia-10), according to claim 1, which comprises ring-closure reacting one or more condensed heteroaromatic five-membered rings.

6. An oligomer, polymer or dendrimer comprising one or more compounds of the formulae (Ia-1)-(Ia-10), according to claim 1, where the bond(s) to the polymer, oligomer or dendrimer is optionally localised at any position in formulae (Ia-1)-(Ia-10), substituted by $R^1$ or $R^2$.

7. A formulation comprising at least one compound of the formulae (Ia-1)-(Ia-10), according to claim 1 and at least one solvent.

8. A formulation comprising at least one polymer, oligomer or dendrimer according to claim 6 and at least one solvent.

9. An electronic device comprising the compound according to claim 1.

10. An electronic device comprising the polymer, oligomer or dendrimer according to claim 6.

11. An organic electroluminescent device (OLED) comprising the compound according to claim 1.

12. The Electronic device according to claim 9, wherein in the device is an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell, an organic laser diode or an organic electroluminescent device.

13. An organic electroluminescent device which comprises the compound according to claim 1 is employed as hole-transport material in a hole-transport layer or hole-injection layer and/or is employed as matrix material in an emitting layer and/or as electron-transport material in an electron-transport layer.

14. An organic electroluminescent device which comprises the polymer, oligomer or dendrimer according to claim 6 is employed as hole-transport material in a hole-transport layer or hole-injection layer and/or is employed as matrix material in an emitting layer and/or as electron-transport material in an electron-transport layer.

15. The compound according to claim 1, wherein two or more radicals $R^2$ are linked to one another and form an aliphatic ring or a condensed aryl or heteroaryl group.

16. The compound according to claim 15, wherein two or more radicals $R^2$ are linked to one another and form a heteroaryl group which has 4 to 8 aromatic ring atoms.

* * * * *